US012410226B2

(12) United States Patent
Garcia et al.

(10) Patent No.: US 12,410,226 B2
(45) Date of Patent: Sep. 9, 2025

(54) INTERFERON-GAMMA BIASED AGONISTS

(71) Applicant: THE BOARD OF TRUSTEES OF THE LELAND STANFORD JUNIOR UNIVERSITY, Stanford, CA (US)

(72) Inventors: Kenan Christopher Garcia, Menlo Park, CA (US); Juan Luis Mendoza, Chicago, IL (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1051 days.

(21) Appl. No.: 17/264,140

(22) PCT Filed: Jul. 29, 2019

(86) PCT No.: PCT/US2019/043977
§ 371 (c)(1),
(2) Date: Jan. 28, 2021

(87) PCT Pub. No.: WO2020/028275
PCT Pub. Date: Feb. 6, 2020

(65) Prior Publication Data
US 2021/0309707 A1 Oct. 7, 2021

Related U.S. Application Data

(60) Provisional application No. 62/712,128, filed on Jul. 30, 2018.

(51) Int. Cl.
*C07K 14/57* (2006.01)
*A61K 38/21* (2006.01)
*A61P 35/00* (2006.01)

(52) U.S. Cl.
CPC ............ *C07K 14/57* (2013.01); *A61K 38/217* (2013.01); *A61P 35/00* (2018.01)

(58) Field of Classification Search
CPC .......... C07K 14/57; A61K 38/17; A61P 35/00
See application file for complete search history.

(56) References Cited

U.S. PATENT DOCUMENTS

| | | | |
|---|---|---|---|
| 4,522,811 A | 6/1985 | Eppstein et al. | |
| 4,845,196 A | 7/1989 | Cowling | |
| 6,046,034 A | 4/2000 | Waschuetza et al. | |
| 6,468,798 B1 | 10/2002 | Debs et al. | |
| 7,504,237 B2 | 3/2009 | Jensen et al. | |
| 2002/0192183 A1* | 12/2002 | Jensen ................... | C07K 14/57 435/69.51 |
| 2006/0251619 A1 | 11/2006 | Borrelly et al. | |
| 2008/0260820 A1 | 10/2008 | Borrelly et al. | |
| 2015/0023918 A1 | 1/2015 | Cox et al. | |

FOREIGN PATENT DOCUMENTS

| | | | | |
|---|---|---|---|---|
| EP | 0170917 A1 | 2/1986 | | |
| EP | 0353910 A2 | 2/1990 | | |
| JP | 2004522803 A | 7/2004 | | |
| WO | WO-2004005341 A2 * | 1/2004 | ......... | C07K 14/4723 |
| WO | 2012028961 A2 | 3/2012 | | |
| WO | 2014106843 A2 | 7/2014 | | |
| WO | 2018077893 A1 | 5/2018 | | |
| WO | 2020028275 A1 | 2/2020 | | |
| WO | 2020106843 A1 | 5/2020 | | |

OTHER PUBLICATIONS

Yphantis et al. (Aug. 27, 1987) "Sedimentation Equilibrium Measurements of Recombinant DNA Derived Human Interferon Gamma", Biochemistry, 26(17):5422-5427.
Partial European Search Report for Application No. EP 19845344.1, mailed on Apr. 11, 2024, 7 pages.
Uze et al. (Apr. 2015) "High Efficiency Targeting of IFN-α Activity: Possible Applications in Fighting Tumours and Infections", Cytokine & Growth Factor Reviews, 26(2):179-182.
Vogt et al. (2005) "Gains of Glycosylation Comprise an Unexpectedly Large Group of Pathogenic Mutations", Nature Genetics, 37(7):692-700.
Walter et al. (Jul. 20, 1995) "Crystal Structure of a Complex Between Interferon-γ and Its Soluble High-Affinity Receptor", Nature, 376:230-235.
Wilmes et al. (May 25, 2015) "Receptor Dimerization Dynamics as a Regulatory Valve for Plasticity of Type I Interferon Signaling", Journal of Cell Biology, 209(4):579-593.
Wong et al. (Jun. 15, 1993) "A Double-Filter Method for Nitrocellulose-Filter Binding: Application to Protein-nucleic Acid Interactions", Proceedings of the National Academy of Sciences of the United States of America, 90(12):5428-5432.
Xia et al. (Oct. 2002) "siRNA-Mediated Gene Silencing in Vitro and in Vivo", Nature Biotechnology, 20(10):1006-1010.
International Search Report and Written Opinion for Application No. PCT/US2019/043977, mailed on Dec. 6, 2019, 12 pages.
(2003) RN 487503-47-9, Protein Sequence, GenBank CAA01147.
(2003) RN 487549-54-2, Protein Sequence GenBank CAA01207.
Adams et al. (Feb. 2010) "Phenix: A Comprehensive Python-based System for Macromolecular Structure Solution", Acta Crystallographica. Section D, Biological Crystallography, 66(2):213-221.
Afonine et al. (Apr. 2012) "Towards Automated Crystallographic Structure Refinement with Phenix.Refine", Acta Crystallographica. Section D, Biological Crystallography, 68(4):352-367.
Altschul et al. (1990) "Basic Local Alignment Search Tool", Journal of Molecular Biology, 215(3):403-410.

(Continued)

*Primary Examiner* — Kimberly Ballard
(74) *Attorney, Agent, or Firm* — Mintz Levin Cohn Ferris Glovsky and Popeo, P.C.

(57) ABSTRACT

Disclosed herein are compositions and methods for modulating IFN-γ-mediated signaling by completely or partially agonizing the downstream signal transduction mediated through at least one of the IFN-γ receptors. More particularly, the disclosure provides novel IFN-γ polypeptide variants with reduced binding affinity to at least one of its receptors. The disclosure also provides compositions and methods useful for producing such molecules, as well as methods for the treatment of health diseases associated with the perturbation of signal transduction mediated by IFN-γ.

21 Claims, 16 Drawing Sheets

Specification includes a Sequence Listing.

(56) References Cited

OTHER PUBLICATIONS

Bach et al. (1995) "Ligand-induced Autoregulation of IFN-gamma Receptor Beta Chain Expression in T Helper Cell Subsets", Science, 270(5239):1215-1218.
Bandaranayake et al. (Nov. 2011) "Daedalus: a Robust, Turnkey Platform for Rapid Production of Decigram Quantities of Active Recombinant Proteins in Human Cell Lines Using Novel Lentiviral Vectors", Nucleic Acids Research, 39(21):e143 (11 pages).
Bern (Dec. 2012) "Byonic: Advanced Peptide and Protein Identification Software", Current Protocols in Bioinformatics, 13:13.20.1-13.20.14.
Blouin et al. (Aug. 11, 2016) "Glycosylation-Dependent IFN-γR Partitioning in Lipid and Actin Nanodomains Is Critical for JAK Activation", Cell, 166(4):920-934.
Brideau-Andersen et al. (May 15, 2007) "Directed Evolution of Gene-shuffled IFN-α Molecules With Activity Profiles Tailored for Treatment of Chronic Viral Diseases", Proceedings of the National Academy of Sciences, 104(20):8269-8274.
Caceci Marco (1984) "Fitting Curves to Data : The Simplex Algorithm is the Answer", Byte, 9:340-348.
Chen et al. (Jan. 2010) "Molprobity: All-atom Structure Validation for Macromolecular Crystallography", Acta Crystallographica. Section D, Biological Crystallography, 66(1):12-21.
Devereux et al. (Jan. 11, 1984) "A Comprehensive Set of Sequence Analysis Programs for the VAX", Nucleic Acids Research, 12(1 Pt 1):387-395.
Ealick et al. (May 3, 1991) "Three-Dimensional Structure of Recombinant Human Interferon-Gamma", Science, 252 (5006):698-702.
Emsley et al. (Apr. 2010) "Features and Development of Coot", Acta Crystallographica. Section D, Biological Crystallography, 66(4):486-501.
Erratum et al. (Feb. 1, 1996) "ASHP's Drug Information Series", American Journal of Health-System Pharmacy, 53(3):325 page.
Farrar et al. (Apr. 1993) "The Molecular Cell Biology of Interferon-gamma and its Receptor", Annual Review of Immunology, 11:571-611.
Gray et al. (Aug. 26, 1982) "Structure of the Human Immune Interferon Gene", Nature, 298:859-863.
Gray et al. (Feb. 11, 1982) "Expression of Human Immune Interferon cDNA in E. coli and Monkey Cells", Nature, 295:503-508.
Ho et al. (Mar. 9, 2017) "Decoupling the Functional Pleiotropy of Stem Cell Factor by Tuning C-Kit Signaling", Cell, 168(6):1041-1052.
Kabsch W. (Feb. 1, 2010) "XDS", Acta Crystallogr D Biol Crystallogr. 66(2):125-132.
Karplus (Oct. 2015) "Assessing and Maximizing Data Quality in Macromolecular Crystallography", Current Opinion in Structural Biology, 34:60-68.
Kotenko et al. (Sep. 8, 1995) "Interaction Between the Components of the Interferon Gamma Receptor Complex", Journal of Biological Chemistry, 270(36):20915-20921.
Krause et al. (2002) "Seeing the Light: Preassembly and Ligand-induced Changes of the Interferon Gamma Receptor Complex in Cells", Molecular & Cellular Proteomics, 1(10):805-815.
Levin et al. (Mar. 25, 2012) "Exploiting a Natural Conformational Switch to Engineer an Interleukin-2 'superkine'", Nature, 484:529-533.
Lundell et al. (Jun. 10, 1994) "Importance of the Loop Connecting A and B Helices of Human Interferon-gamma in Recognition by Interferon-gamma Receptor", Journal of Biological Chemistry, 269(23):16159-16162.
Lunn et al. (Apr. 1992) "A Point Mutation of Human Interferon Gamma Abolishes Receptor Recognition", Protein Engineering, 5(3):253-257.
Mandai et al. (May 15, 2016) "Dual Faces of IFNγ in Cancer Progression: A Role of PD-L1 Induction in the Determination of Pro- and Antitumor Immunity", Clinical Cancer Research, 22(10):2329-2334.
Matrosovich et al. (Feb. 2012) "Solid-Phase Assays of Receptor-Binding Specificity", Methods in molecular biology, 865:71-94.
McCaffrey et al. (Jul. 4, 2002) "RNA Interference in Adult Mice", Nature, 418(6893):38-39.
McCoy (Aug. 2007) "Phaser Crystallographic Software", Journal of Applied Crystallography, 40(4):658-674.
Mendoza et al. (Mar. 21, 2017) "The IFN-λ-IFN-λR1-IL-10Rβ Complex Reveals Structural Features Underlying Type III IFN Functional Plasticity", Immunity, 46(3):379-392.
Mikulecy et al. (2016) "Crystal Structure of Human Interferon-γ Receptor 2 Reveals the Structural Basis for Receptor Specificity", Acta Crystallographica Section D: Structural Biology, 72(9):1017-1025.
Moraga et al. (May 12, 2017) "Synthekines are Surrogate Cytokine and Growth Factor Agonists That Compel Signaling Through Non-Natural Receptor Dimers", eLife, 6:e22882 (22 pages).
Moraga et al. (2015) "Tuning Cytokine Receptor Signaling by Re-orienting Dimer Geometry With Surrogate Ligands", Cell, 160(6):1196-1208.
Munson et al. (Sep. 1, 1980) "Ligand: A Versatile Computerized Approach for Characterization of Ligand-binding Systems", Analytical Biochemistry, 107(1):220-239.
Nakajima et al. (Apr. 15, 2001) "A Role of Interferon-γ (IFN-γ) in Tumor Immunity: T Cells with the Capacity to Reject Tumor Cells Are Generated but Fail to Migrate to Tumor Sitesin IFN-γ-deficient Mice", Cancer Research, 61(8):3399-3405.
Nuara et al. (Feb. 12, 2008) "Structure and Mechanism of IFN-γ Antagonism by an Orthopoxvirus IFN-γ-Binding Protein", Proceedings of the National Academy of Sciences, 105(6):1861-1866.
Pace et al. (Feb. 1, 1985) "Comparative Effects of Various Classes of Mouse Interferons on Macrophage Activation for Tumor Cell Killing", Journal of Immunology, 134(2):977-981.
Painter et al. (Apr. 2006) "Optimal Description of a Protein Structure in Terms of Multiple Groups Undergoing TLS Motion", Acta Crystallographica. Section D, Biological Crystallography, 62(4):439-450.
Pernis et al. (Jul. 14, 1995) "Lack of Interferon Gamma Receptor Beta Chain and the Prevention of Interferon Gamma Signaling in TH1 Cells", Science, 269(5221):245-247.
Putnam David A. (Jan. 15, 1996) "Antisense Strategies and Therapeutic Applications", American Journal of Health-System Pharmacy, 53(2):151-160.
Randal et al. (Feb. 7, 2001) "The Structure and Activity of a Monomeric Interferon-gamma:alpha-chain Receptor Signaling Complex", Structure, 9(2):155-163.
Richter et al. (Jul. 14, 2017) "Ligand-induced Type II Interleukin-4 Receptor Dimers Are Sustained by Rapid Re-association Within Plasma Membrane Microcompartments", Nature Communications, 8:15976(15 pages).
Roder et al. (Sep. 9, 2014) "Rapid Transfer of Transmembrane Proteins for Single Molecule Dimerization Assays in Polymer-Supported Membranes", ACS Chemical Biology, 9(11):2479-2484.
Serge et al. (Jul. 6, 2008) "Dynamic Multiple-Target Tracing to Probe Spatiotemporal Cartography of Cell Membranes", Nature Method, 5:687-694.
Smart et al. (Apr. 2012) "Exploiting Structure Similarity in Refinement: Automated NCS and Target-structure Restraints in BUSTER", Acta Crystallographica. Section D, Biological Crystallography, 68(4):368-380.
Spiess et al. (Oct. 2015) "Alternative Molecular Formats and Therapeutic Applications for Bispecific Antibodies", Molecular Immunology, 67(2 Pt A):95-106.
Stark et al. (1998) "How Cells Respond to Interferons", Annual Review of Biochemistry, 67:227-264.
Tau et al. (Nov. 15, 2001) "Regulation of IFN-γ Signaling Is Essential for the Cytotoxic Activity of CD8+ T Cells", Journal of Immunology, 167(10):5574-5582.
Thiel et al.(Sep. 15, 2000) "Observation of an Unexpected Third Receptor Molecule in the Crystal Structure of Human Interferon-gamma Receptor Complex", Structure, 8(9):927-936.
Thomas et al., "Structural Linkage Between Ligand Discrimination and Receptor Activation by Type I Interferons", Cell, Aug. 19, 2011, 146(4):621-632.

(56) References Cited

OTHER PUBLICATIONS

Landar et al. (May 26, 2000) "Design, Characterization, and Structure of a Biologically Active Single-Chain Mutant of Human IFN-gamma", Journal of Molecular Biology, 299(1):169-179.

Mendoza et al. (Mar. 2019) "Structure of the IFN Gamma Receptor Complex Guides Design of Biased Agonists", Nature, 567(7746):56-60 (19 pages).

* cited by examiner

QDPYVKEAENLKKYFNAGHSDVADNGTLFLGILKNWKEESDR
KIMQSQIVSFYFKLFKNFKDDQSIQKSVETIKEDMNVKFFNS
NKKKRDDFEKLTNYSVTDLNVQRKAIHELIQVMAELSPAAKT
GKRKRSQ (SEQ ID NO: 1)

QDPYVKEAENLKKYFNAGHSDVADNGTLFLGILKNWKEESDR
KIMQSQIVSFYFKLFKNFKDDQSIQKSVETIKEDMNVKFFNS
NKKKRDDFEKLTNYSVTDLNVQRKAIHELIQVMAELSPAAKT
GKRKRSQ*GGGSLEVLFQGPGGGS*QDPYVKEAENLKKYFNAGH
SDVADNGTLFLGILKNWKEESDRKIMQSQIVSFYEKLFKNFK
DDQSIQKSVETTAYDMNVKFFRSNKKKRDDFEKLTNYSVTDL
NVQRKAIHELIQVMAELSPAAKTGKRKRSQ (SEQ ID NO: 2)

QDPYVKEAENLKKYFNAGHSDVADNGTLFLGILKNWKEESDR
KIMQSQIVSFYFKLFKNFKDDQSIQKSVETIKEDMNVKFFNS
NKKKRDDFEKLTNYSVTDLNVQRKAIDELIQVMAELSPAAKT
GKRKRSQ*GGGSLEVLFQGPGGGS*QDPYVKEAENLKKYFNAGH
SDVADNGTLFLGILKNWKEESDRKIMQSQIVSFYFKLFKNFK
DDQSIQKSVETAYDMNVKFFRSNKKKRDDFEKLTNYSVTDL
NVQRKAIHELIQVMAELSPAAKTGKRKRSQ (SEQ ID NO: 3)

QDPYVKEAENLKKYFNAGHSDVADNGTLFLGILKNWKEESDR
KIMQSIVSFYFKLFKNFKDDQSIQKSVETIAYDMNVKFFRS
NKKKRDDFEKLTNYSVTDLNVQRKATHELIQVMAELSPAAKT
GKRKRSQ (SEQ ID NO: 4)

QDPYVKEAENLKKYFNAGHSDV*EEK*GTLFLGILKNWKEESDR
KIMQSQIVSFYFKLFKNFKDDQSIQKSVETIAYDMNVKFFRS
NKKKRDDFEKLTNYSVTDLNVQRKAI[D]ELIQVMAELSPAAKT
GKRKRSQ*GGGSLEVLFQGPGGGS*QDPYVKEAENLKKYFNAGH
SDVADNGTLFLGILKNWKEESDRKIMQSQIVSFYFKLFKNFK
DDQSIQKSVETIAYDMNVKFFRSNKKKKRDDFEKLTNYSVTDL
NVQRKAIHELIQVMAELSPAAKTGKRKRSQ (SEQ ID NO: 5)

SEQUENCE LISTING

<160> NUMBER OF SEQ ID NOS: 14

<210> SEQ ID NO 1
<211> LENGTH: 133
<212> TYPE: PRT
<213> ORGANISM: Homo sapiens
<220> FEATURE:
<221> NAME/KEY: misc_feature
<223> OTHER INFORMATION: human interferon-gamma

<400> SEQUENCE: 1

```
Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Lys Arg Asp Asp Phe Glu Lys Leu Thr
                85                  90                  95
```

```
Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln
    130

<210> SEQ ID NO 2
<211> LENGTH: 282
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (134)..(149)
<223> OTHER INFORMATION: Linker
<220> FEATURE:
<221> NAME/KEY: misc_feature
<223> OTHER INFORMATION: Interferon-gamma variant GIFN1

<400> SEQUENCE: 2

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Gly Gly Gly Ser Leu Glu Val Leu Phe Gln Gly
    130                 135                 140

Pro Gly Gly Gly Ser Gln Asp Pro Tyr Val Lys Glu Ala Glu Asn Leu
145                 150                 155                 160

Lys Lys Tyr Phe Asn Ala Gly His Ser Asp Val Ala Asp Asn Gly Thr
                165                 170                 175

Leu Phe Leu Gly Ile Leu Lys Asn Trp Lys Glu Glu Ser Asp Arg Lys
            180                 185                 190

Ile Met Gln Ser Gln Ile Val Ser Phe Tyr Phe Lys Leu Phe Lys Asn
        195                 200                 205

Phe Lys Asp Asp Gln Ser Ile Gln Lys Ser Val Glu Thr Ile Ala Tyr
    210                 215                 220

Asp Met Asn Val Lys Phe Phe Arg Ser Asn Lys Lys Arg Asp Asp
225                 230                 235                 240

Phe Glu Lys Leu Thr Asn Tyr Ser Val Thr Asp Leu Asn Val Gln Arg
                245                 250                 255

Lys Ala Ile His Glu Leu Ile Gln Val Met Ala Glu Leu Ser Pro Ala
            260                 265                 270

Ala Lys Thr Gly Lys Arg Lys Arg Ser Gln
        275                 280
```

```
<210> SEQ ID NO 3
<211> LENGTH: 282
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (134)..(149)
<223> OTHER INFORMATION: Linker
<220> FEATURE:
<221> NAME/KEY: misc_feature
<223> OTHER INFORMATION: Interferon-gamma variant GIFN2

<400> SEQUENCE: 3
```

| | | | | | | | | | | | | | | |
|---|---|---|---|---|---|---|---|---|---|---|---|---|---|---|
| Gln | Asp | Pro | Tyr | Val | Lys | Glu | Ala | Glu | Asn | Leu | Lys | Lys | Tyr | Phe | Asn |
| 1 | | | | 5 | | | | | 10 | | | | | 15 | |

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
50                  55                  60

Ser Ile Gln Lys Ser Val Glu Thr Ile Lys Glu Asp Met Asn Val Lys
65                  70                  75                  80

Phe Phe Asn Ser Asn Lys Lys Arg Asp Asp Phe Glu Lys Leu Thr
                85                  90                  95

Asn Tyr Ser Val Thr Asp Leu Asn Val Gln Arg Lys Ala Ile Asp Glu
                100                 105                 110

Leu Ile Gln Val Met Ala Glu Leu Ser Pro Ala Ala Lys Thr Gly Lys
            115                 120                 125

Arg Lys Arg Ser Gln Gly Gly Ser Leu Glu Val Leu Phe Gln Gly
    130                 135                 140

Pro Gly Gly Gly Ser Gln Asp Pro Tyr Val Lys Glu Ala Glu Asn Leu
145                 150                 155                 160

Lys Lys Tyr Phe Asn Ala Gly His Ser Asp Val Ala Asp Asn Gly Thr
                165                 170                 175

Leu Phe Leu Gly Ile Leu Lys Asn Trp Lys Glu Glu Ser Asp Arg Lys
            180                 185                 190

Ile Met Gln Ser Gln Ile Val Ser Phe Tyr Phe Lys Leu Phe Lys Asn
        195                 200                 205

Phe Lys Asp Asp Gln Ser Ile Gln Lys Ser Val Glu Thr Ile Ala Tyr
    210                 215                 220

Asp Met Asn Val Lys Phe Phe Arg Ser Asn Lys Lys Arg Asp Asp
225                 230                 235                 240

Phe Glu Lys Leu Thr Asn Tyr Ser Val Thr Asp Leu Asn Val Gln Arg
                245                 250                 255

Lys Ala Ile His Glu Leu Ile Gln Val Met Ala Glu Leu Ser Pro Ala
            260                 265                 270

Ala Lys Thr Gly Lys Arg Lys Arg Ser Gln
        275                 280

```
<210> SEQ ID NO 4
<211> LENGTH: 133
<212> TYPE: PRT
<213> ORGANISM: Artificial Sequence
<220> FEATURE:
<223> OTHER INFORMATION: Synthetic polypeptide
```

```
<220> FEATURE:
<221> NAME/KEY: misc_feature
<222> LOCATION: (134)..(149)
<223> OTHER INFORMATION: Linker
<220> FEATURE:
<221> NAME/KEY: misc_feature
<223> OTHER INFORMATION: Interferon-gamma variant GIFN3

<400> SEQUENCE: 4

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Ala Tyr Asp Met Asn Val Lys
65                  70                  75                  80

Phe Phe Arg Ser Asn Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln
    130

<210> SEQ ID NO 5
<211> LENGTH: 282
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (134)..(149)
<223> OTHER INFORMATION: Linker
<220> FEATURE:
<221> NAME/KEY: misc_feature
<223> OTHER INFORMATION: Interferon-gamma variant GIFN4

<400> SEQUENCE: 5

Gln Asp Pro Tyr Val Lys Glu Ala Glu Asn Leu Lys Lys Tyr Phe Asn
1               5                   10                  15

Ala Gly His Ser Asp Val Glu Glu Lys Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Ala Tyr Asp Met Asn Val Lys
65                  70                  75                  80

Phe Phe Arg Ser Asn Lys Lys Arg Asp Asp Phe Glu Lys Leu Thr
                85                  90                  95

Asn Tyr Ser Val Thr Asp Leu Asn Val Gln Arg Lys Ala Ile Asp Glu
            100                 105                 110

Leu Ile Gln Val Met Ala Glu Leu Ser Pro Ala Ala Lys Thr Gly Lys
        115                 120                 125

Arg Lys Arg Ser Gln Gly Gly Gly Ser Leu Glu Val Leu Phe Gln Gly
```

```
                    130                 135                 140
Pro Gly Gly Gly Ser Gln Asp Pro Tyr Val Lys Glu Ala Glu Asn Leu
145                 150                 155                 160

Lys Lys Tyr Phe Asn Ala Gly His Ser Asp Val Ala Asp Asn Gly Thr
                165                 170                 175

Leu Phe Leu Gly Ile Leu Lys Asn Trp Lys Glu Glu Ser Asp Arg Lys
            180                 185                 190

Ile Met Gln Ser Gln Ile Val Ser Phe Tyr Phe Lys Leu Phe Lys Asn
        195                 200                 205

Phe Lys Asp Asp Gln Ser Ile Gln Lys Ser Val Glu Thr Ile Ala Tyr
    210                 215                 220

Asp Met Asn Val Lys Phe Phe Arg Ser Asn Lys Lys Arg Asp Asp
225                 230                 235                 240

Phe Glu Lys Leu Thr Asn Tyr Ser Val Thr Asp Leu Asn Val Gln Arg
                245                 250                 255

Lys Ala Ile His Glu Leu Ile Gln Val Met Ala Glu Leu Ser Pro Ala
            260                 265                 270

Ala Lys Thr Gly Lys Arg Lys Arg Ser Gln
        275                 280
```

<210> SEQ ID NO 6
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: Linker peptide

<400> SEQUENCE: 6

```
Gly Gly Gly Ser Leu Glu Val Leu Phe Gln Gly Pro Gly Gly Gly Ser
1               5                   10                  15
```

<210> SEQ ID NO 7
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: 18S fwd primer

<400> SEQUENCE: 7
gtaacccgtt gaacccatt                                        20

<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: 18 S rev primer

<400> SEQUENCE: 8
ccatccaatc ggtagtagcg                                       20

<210> SEQ ID NO 9
<211> LENGTH: 19
<212> TYPE: DNA

```
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: HLA-A fwd primer

<400> SEQUENCE: 9
ccaggtaggc tctcaactg                                                     19

<210> SEQ ID NO 10
<211> LENGTH: 19
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: HLA-A rev primer

<400> SEQUENCE: 10
ccaggtaggc tctcaactg                                                     19

<210> SEQ ID NO 11
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: HLA-B fwd primer

<400> SEQUENCE: 11
aaccgtcctc ctgctgctct c                                                  21

<210> SEQ ID NO 12
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: HLA-B rev primer

<400> SEQUENCE: 12
ctgtgtgttc cggtcccaat ac                                                 22

<210> SEQ ID NO 13
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: PD-L1 fwd primer

<400> SEQUENCE: 13
tggcatttgc tgaacgcatt t                                                  21

<210> SEQ ID NO 14
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
```

```
<221> NAME/KEY: misc_feature
<223> OTHER INFORMATION: PD-L1 rev primer

<400> SEQUENCE: 14
tgcagccagg tctaattgtt tt                                              22
```

INTERFERON-GAMMA BIASED AGONISTS

CROSS-REFERENCE TO RELATED APPLICATIONS

The present application is a U.S. National Phase Application of PCT International Application No. PCT/US2019/043977, filed on Jul. 29, 2019, designating the United States of America, which is an International Application of and claims the benefit of priority to U.S. Provisional Patent Application Serial No. 62/712,128, filed on Jul. 30, 2018. The disclosures of the above-referenced applications are herein expressly incorporated by reference in their entireties, including any drawing.

STATEMENT REGARDING FEDERALLY SPONSORED R&D

This invention was made with Government support under contracts AI051321 and CA177684 awarded by the National Institutes of Health. The Government has certain rights in the invention.

INCORPORATION OF THE SEQUENCE LISTING

The present application is being filed along with a Sequence Listing in electronic format. The material in the accompanying Sequence Listing is hereby incorporated by reference into this application. The accompanying Sequence Listing text file, entitled Sequence Listing_078430-505N01US, was created on Jan. 27, 2011, and is 13 KB.

FIELD

The present disclosure relates generally to the field of molecular biology and immunology and particularly relates to novel interferon gamma (IFN-γ) polypeptide variants with reduced binding affinity to at least one of its receptors. The disclosure also provides compositions and methods useful for producing such IFN-γ polypeptide variants, as well as methods for modulating IFN-γ-mediated signaling, and/or for the treatment of health diseases associated with the perturbation of signal transduction mediated by IFN-γ.

BACKGROUND

Biopharmaceuticals or the use of pharmaceutical compositions comprising a therapeutic protein for the treatment of diseases or health conditions is a core strategy for a number of pharmaceutical and biotechnology companies. For example, several members of the cytokine family have been reported to be effective in the treatment of cancer and play a major role in the development of cancer immunotherapy. Therefore, the cytokine family has been the focus of much clinical work and effort to improve its administration and bio-assimilation. However, the clinical success of existing therapeutic approaches involving cytokines has been limited. Their limitations are often due to off-target toxicity and ineffectiveness of the cytokines, which is largely due to the fact that cytokines have receptors on both desired and undesired responder cells that counterbalance one another and lead to unwanted side effects. In recent years, cytokine engineering has emerged as a promising strategy with various attempts to tailor cytokines to arrive at recombinant cytokines with more desired activities and reduced toxicity.

In particular, the interferons have been of particular clinical interest for immunotherapy due to their powerful immune-modulating effects. However, they are extremely pleiotropic (e.g., acting on many different cells types), and have been clinically relatively ineffective, with the exception of some rare cases. For example, human interferon-gamma (IFN-γ), which is generally considered to be a master regulator of the immune system, has been reported as a potent and therapeutically active reagent. IFN-γ, along with IL-2, is the most central and pleiotropic cytokine that acts to both activate and suppress various immune functions depending on the cell types that respond. IFN-γ is produced in a variety of immune cells, such as activated T cells and natural killer (NK) cells. IFN-γ interacts with a specific receptor at the cell surface and activates signal transduction pathways that produce immunomodulatory effects of this cytokine. IFN-γ induces up-regulation of major histocompatibility complex (MHC) class I molecules, which results in enhanced antigen presentation of antigens from viruses and tumors, leading to improved killing of virus-infected cells as well as tumor cells. IFN-γ has been approved for treatment of a variety of diseases including chronic granulomatous disease and malignant osteoporosis. Hence, IFN-γ could be an important therapeutic agent but its effect is mitigated by pleiotropy because its receptors are expressed on many different cell types, resulting in counterbalancing activities that reduce its efficacy in treating disease. In addition, natural IFN-γ polypeptides can elicit undesirable side effects as well as various problems of administration, bioavailability, and short half-life. For example, IFN-γ has been reported to also upregulate various checkpoint receptors on tumor cells, such as Programmed Cell Death Ligand-1 (PD-L1), which in turn diminishes the antitumor response.

Hence, there is a need for additional approaches to improve properties of IFN-γ for its use as a therapeutic agent. In particular, there is a need for variants of IFN-γ that can selectively activate certain downstream genes and actions over others, leading to improved use as an anti-tumor agent or immune modulator.

SUMMARY

The present disclosure relates generally to the field of molecular biology and immunology, and particularly to compositions and methods for modulating signal transduction pathway mediated by IFN-γ in a subject in need thereof. As described in greater detail below, IFN-γ-mediated signaling can be modulated via selective reduction of IFN-γ-binding to one or both of its two receptors, interferon-gamma receptor subunit 1 (IFN-γR1) and interferon-gamma receptor subunit 2 (IFN-γR2). In some particular embodiments, the disclosure provides novel IFN-γ polypeptide variants with reduced binding affinity to IFN-γR1 or IFN-γR2 that completely or partially agonize the downstream signal mediated by the respective IFN-γR1 and/or IFN-γR2 receptors. The disclosure also provides compositions and methods useful for producing such IFN-γ polypeptide variants, as well as methods for the treatment of health diseases associated with perturbations of signal transduction mediated by IFN-γ.

In one aspect, provided herein are various recombinant polypeptides including a first amino acid sequence having at least 95% identity to an IFN-γ polypeptide having the amino acid sequence of SEQ ID NO: 1, and further including at least one amino acid substitution at a position corresponding to an amino acid residue selected from the group consisting of Q1, D2, P3, K6, Q64, Q67, K68, E71, T72, K74, E75, D76, N78, V79, K80, N83, S84, K86, R89, and D90 of SEQ ID NO: 1, and any combination thereof.

Non-limiting exemplary embodiments of the disclosed recombinant polypeptides according to the present disclosure include one or more of the following features. In some embodiments, the at least one amino acid substitution is at a position corresponding to an amino acid residue selected from the group consisting of K74, E75, and N83 of SEQ ID NO: 1, and any combination thereof. In some embodiments, the at least one amino acid substitution is at a position corresponding to the amino acid residue K74 of SEQ ID NO: 1. In some embodiments, the at least one amino acid substitution is a Lys-to-Ala substitution (K74A). In some embodiments, the at least one amino acid substitution is at a position corresponding to the amino acid residue E75 of SEQ ID NO: 1. In some embodiments, the at least one amino acid substitution is a Glu-to-Tyr substitution (E75Y). In some embodiments, the at least one amino acid substitution is at a position corresponding to the amino acid residue N83 of SEQ ID NO: 1. In some embodiments, the at least one amino acid substitution is an Asn-to-Arg substitution (N83R). In some embodiments, the first amino acid sequence includes the amino acid substitutions K74A, E75Y, and N83R. In some embodiments, the first amino acid sequence further includes one or more additional amino acid substitutions at positions corresponding to amino acid residues selected from the group consisting of A23, D24, N25, and H111 of SEQ ID NO: 1, and any combination thereof.

In some embodiments disclosed herein, the recombinant polypeptide of the disclosure further including a second amino acid sequence having at least 95% identity to a gamma-interferon polypeptide having the amino acid sequence of SEQ ID NO: 1, wherein the second amino acid sequence is operably linked to the first amino acid sequence. In some embodiments, the second amino acid sequence includes at least one amino acid substitution at a position corresponding to an amino acid residue selected from the group consisting of Q1, D2, P3, K6, Q64, Q67, K68, E71, T72, K74, E75, D76, N78, V79, K80, N83, S84, K86, R89, and D90 of SEQ ID NO: 1, and any combination thereof. In some embodiments, the second amino acid sequence includes at least one amino acid substitution at a position corresponding to an amino acid residue selected from the group consisting of K74, E75, and N83 of SEQ ID NO: 1, and any combination thereof. In some embodiments, the at least one amino acid substitution in the second amino acid sequence is at a position corresponding to an amino acid residue selected from the group consisting of K74, E75, and N83 of SEQ ID NO: 1, and any combination thereof. In some embodiments, the at least one amino acid substitution in the second amino acid sequence is at a position corresponding to the amino acid residue K74 of SEQ ID NO: 1. In some embodiments, the at least one amino acid substitution in the sequence amino acid sequence is a Lys-to-Ala substitution (K74A). In some embodiments, the at least one amino acid substitution in the second amino acid sequence is at a position corresponding to the amino acid residue E75 of SEQ ID NO: 1. In some embodiments, the at least one amino acid substitution in the second amino acid sequence is a Glu-to-Tyr substitution (E75Y). In some embodiments, the at least one amino acid substitution in the sequence amino acid sequence is at a position corresponding to the amino acid residue N83 of SEQ ID NO: 1. In some embodiments, the at least one amino acid substitution in the second amino acid sequence is an Asn-to-Arg substitution (N83R).

In some embodiments of the recombinant polypeptide disclosed herein, the first amino acid sequence and the second amino acid sequence of the polypeptide include the same amino acid substitutions. In some embodiments, the first amino acid sequence and the second amino acid sequence include different amino acid substitutions. In some embodiments, the second amino acid sequence is operably linked to the first amino acid sequence via a peptide linker sequence. In some embodiments, the peptide linker sequence includes 1-100 amino acid residues. In some embodiments, the peptide linker sequence includes at least one glycine residue. In some embodiments, the peptide linker sequence includes a glycine-serine linker. In some embodiments, the peptide linker sequence is a cleavable linker sequence.

In some embodiments, the recombinant polypeptide of the disclosure includes, in the N-terminal to C-terminal direction, (a) a first polypeptide segment including a first amino acid sequence with 100% sequence identity to SEQ ID NO: 1; (b) a cleavable peptide linker sequence; and (c) a second polypeptide segment including the amino acid sequence of SEQ ID NO: 1 with amino acid substitutions K74A, E75Y, and N83R. In some other embodiments, the recombinant polypeptide of the disclosure includes, in the N-terminal to C-terminal direction, (a) a first polypeptide segment including the amino acid sequence of SEQ ID NO: 1 with the amino acid substitution H111D; (b) a cleavable peptide linker sequence; and (c) a second polypeptide segment including the amino acid sequence of SEQ ID NO: 1 with the amino acid substitutions K74A, E75Y, and N83R. In yet some other embodiments, the recombinant polypeptide of the disclosure includes, in the N-terminal to C-terminal direction, (a) a first polypeptide segment including the amino acid sequence of SEQ ID NO: 1 with the amino acid substitutions A23E, D24E, N25K, and H111D; (b) a cleavable peptide linker sequence; and (c) a second polypeptide segment including the amino acid sequence of SEQ ID NO: 1 with the amino acid substitutions K74A, E75Y, and N83R. In some embodiments, the recombinant polypeptide of the disclosure includes an amino acid sequence selected from the group consisting of SEQ ID NO: 2, SEQ ID NO: 3, SEQ ID NO: 4, and SEQ ID NO: 5.

In some embodiments of the recombinant polypeptide disclosed herein, at least one of the amino acid substitutions confers reduced binding affinity of the polypeptide to interferon-gamma receptor subunit 1 (IFN-γR1) and/or interferon-gamma receptor subunit 2 (IFN-γR2), compared to the respective binding affinity of a reference polypeptide lacking the at least one amino acid substitution. In some embodiments, the at least one amino acid substitution confers a substantial reduction in binding affinity of the polypeptide to interferon-gamma receptor subunit 2 (IFN-γR2) while substantially retains its binding affinity to interferon-gamma receptor subunit 1 (IFN-γR1), compared to the respective binding affinity of a reference polypeptide lacking the at least one amino acid substitution. In some embodiments, the ratio of IFN-γR2 binding affinity to IFN-γR1 binding affinity of the polypeptide is about 1:500 to about 1:2, as determined by a solid-phase receptor binding assay.

In one aspect, some embodiments of the disclosure relate to a recombinant nucleic acid molecule including a nucleic acid sequence encoding a polypeptide that includes an amino acid sequence having at least 90% identity to the amino acid sequence of a recombinant polypeptide as disclosed herein. In some embodiments, the nucleic acid sequence is operably linked to a heterologous nucleic acid sequence. In some embodiments, the nucleic acid molecule is further defined as an expression cassette or an expression vector.

In another aspect, some embodiments of the disclosure relate to a recombinant cell including a recombinant nucleic acid molecule as disclosed herein. In some embodiments, the recombinant cell is a prokaryotic cell or a eukaryotic cell. In another aspect, some embodiments of the disclosure relate to a cell culture including at least one recombinant cell as disclosed herein.

In yet another aspect, disclosed herein are embodiments of methods for producing a polypeptide including (i) providing one or more recombinant cells as disclosed herein; and (ii) culturing the one or more recombinant cells in a culture medium such that the cells produce the polypeptide encoded by the recombinant nucleic acid molecule. In some embodiments, the methods according to this aspect are performed in vitro, in vivo, or ex vivo. Further provided herein, in another aspect, is a recombinant polypeptide produced by the production method disclosed herein.

In one aspect, some embodiments of the disclosure relate to a composition including a polypeptide as described herein and a pharmaceutically acceptable excipient.

In another aspect, some embodiments of the disclosure relate to a composition including a nucleic acid molecule as described herein and a pharmaceutically acceptable excipient.

In another aspect, some embodiments of the disclosure relate to a composition including a recombinant cell as described herein and a pharmaceutically acceptable excipient.

In yet another aspect, some embodiments disclosed herein relate to a method for modulating IFN-γ-mediated signaling in a subject, the method including administering to the subject an effective amount of a polypeptide as disclosed herein, or a nucleic acid molecule as disclosed herein.

In yet another aspect, some embodiments disclosed herein relate to a method for the treatment of a health disease in a subject in need thereof, the method including administering to the subject an effective amount of a polypeptide as disclosed herein, or a nucleic acid molecule as disclosed herein.

Implementations of embodiments of the treatment methods according to the present disclosure can include one or more of the following features. In some embodiments, he administered polypeptide has reduced capacity to upregulate expression of Programmed death-ligand 1 (PD-L1) in the subject, as compared to a reference polypeptide lacking the at least one amino acid substitution. In some embodiments, the administered polypeptide substantially retains its capacity to upregulate expression of one or more of MHC Class I molecules. In some embodiments, the administered polypeptide has reduced capacity to upregulate expression of PD-L1 while substantially retaining its capacity to upregulate expression of one or more MHC Class I molecules in the subject. In some embodiments, the administration of the polypeptide or nucleic acid molecule does not inhibit T cell activity in the subject. In some embodiments, the administered polypeptide or nucleic acid molecule enhances antitumor immunity in a tumor microenvironment. In some embodiments, the polypeptide or nucleic acid molecule is administered to the subject as a single therapeutic agent or in combination with one or more additional therapeutic agents. In some embodiments, the subject is a mammal. In some embodiments, the mammal is a human. In some embodiments, the subject has or is suspected of having a health disease associated with IFN-γ-mediated signaling. In some embodiments, the health disease is a cancer, an immune disease, or a chronic infection.

Each of the aspects and embodiments described herein are capable of being used together, unless excluded either explicitly or clearly from the context of the embodiment or aspect.

The foregoing summary is illustrative only and is not intended to be in any way limiting. In addition to the illustrative embodiments and features described herein, further aspects, embodiments, objects and features of the disclosure will become fully apparent from the drawings and the detailed description and the claims.

BRIEF DESCRIPTION OF THE DRAWINGS

In FIG. 2, which depicts a side view of the IFN-γ dimer (white and dark gray ribbons, the amino acid residues positions at one of the IFN-γR2 binding interfaces are shown as black sticks. In this figure, IFN-γ amino acid residues that interact with IFN-γR2 include Q1, D2, P3, K6, Q64, Q67, K68, E71, T72, K74, E75, D76, N78, V79, K80, N83, S84, K86, R89, and D90.

In FIG. 3A, which depicts a surface view of the IFN-γ dimer (white and dark gray surfaces), E74A, E75Y, and N75R (black surfaces) mutations are at the IFN-γR2 binding interface and predicted to alter binding. FIG. 3B summarizes the results of a surface plasmon resonance (SPR) experiments measuring affinity of IFN-γR2 for the wild-type 2:2 IFN-γ/IFN-γR1 intermediate complex. FIG. 3C shows that IFN-γR2 binding to the 2:2 IFN-γ (K74A/E75Y/N75R)/IFN-γR1 complex is reduced compared to the wild-type IFN-γ, as evidenced by the SPR traces.

FIGS. 4A-4D depict the structures of four exemplary IFN-γ variants designed to alter binding to one or more of the receptor interfaces (indicated by translucent circles). FIG. 4A depicts the structure of IFN-γ variant GIFN1, in which three amino acid substitutions K74A, E75Y, N83R were engineered into site IIb of the IFN-γ molecule. FIG. 4B depicts the structure of IFN-γ variant GIFN2 which contains three amino acid substitutions K74A, E75Y, N83R engineered into site IIb, and H111D substitution engineered into site Ib of the IFN-γ molecule. FIG. 4C depicts the structure of IFN-γ variant GIFN3, in which three amino acid substitutions K74A, E75Y, N83R were engineered into sites IIa and IIb of the IFN-γ molecule. FIG. 4D depicts the structure of IFN-γ variant GIFN4 which contains the following amino acid substitutions in the IFN-γ molecule: K74A, E75Y, N83R in sites IIa and IIb; A23E, D24E, N25K in site Ia; and H111D in site Ib.

As shown in FIG. 9B, the amino acid sequence of IFN-γ variant GIFN4 contains the following amino acid substitutions in the IFN-γ molecule: K74A, E75Y, N83R in sites IIa and IIb (shown in bold letters); A23E, D24E, N25K in site Ia of chain A (bold italic letters); and H111D in site Ib of chain A (boxed). The amino acid sequences of two IFN-γ monomers are linked to each other via a cleavable peptide linker (italic letters).

FIG. 10A illustrates dose-response for phospho-STAT1 signaling of IFN-γ (black) and IFN-γ variants (GIFN1 (dashed black), GIFN2 (gray), GIFN3 (dashed gray), and GIFN4 (light gray)). In FIG. 10B, A549, a human lung carcinoma cell line, was treat with IFN-γ (WT) or IFN-γ variants at 0.1 nM, 0.5 nM, 2.5 nM, 12.5 nM, and 62.5 nM doses (bars from left to right). After 48 hours, the cells were stained for PD-L1 expression and analyzed. In FIG. 10C, the expression of PD-L1 gene was measured by qPCR by treating A549 cells for 48 hours with 62.5 nM of each protein. Untreated (white); Wild-type IFN-γ (black)); GIFN2 (gray); GIFN3 (dashed gray); GIFN4 (light gray) In FIG. 10D, the experiments were performed similarly to those described in FIG. 10B with the exception that Class I MHC was measured by FACS technique. In FIG. 10E, gene expression of HLA-A was measured by qPCR by treating A549 cells for 48 hours with 62.5 nM of protein. Untreated (white); Wild-type IFN-γ (black)); GIFN2 (gray); GIFN3 (dashed gray); GIFN4 (light gray). In FIGS. 10F-10G, dendritic cells were purified from human blood and treated with IFN-γ (WT) or partial agonists to determine PD-L1 or MHC Class I antigen expression. FIGS. 10H-10I graphically summarize the results of antibody-based experiments performed to determine the ratio of MHC I. PD-L1 expression in A549 cells (FIG. 10H) and dendritic cells (FIG. 10I) treated with each of the IFN-γ partial agonists at different concentrations relative to control cells treated with wild-type IFN-γ.

DETAILED DESCRIPTION OF THE DISCLOSURE

Figure 1:
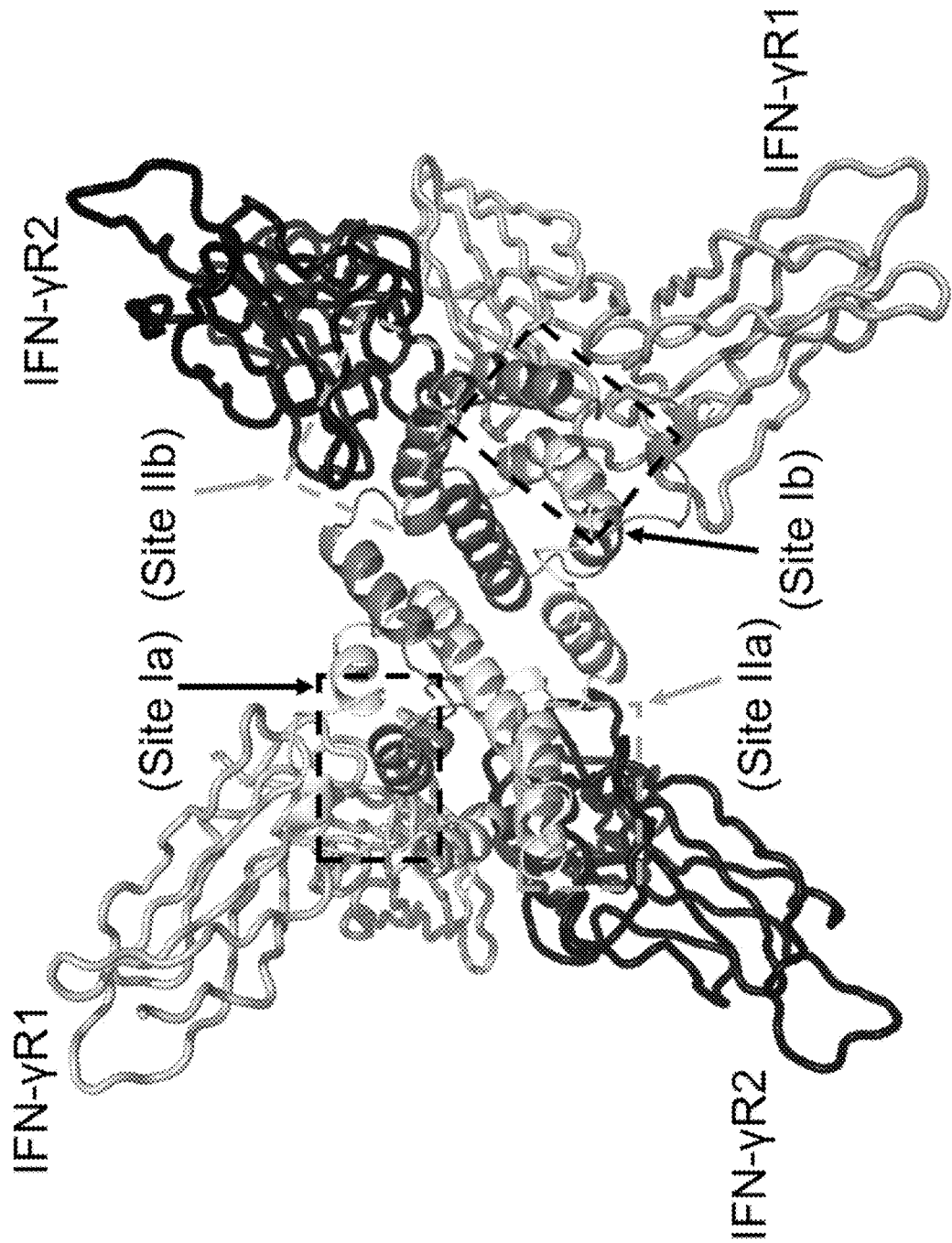
FIG. 1 graphically depicts a structure of the IFN-γ complex with IFN-γR1 and IFN-γR2. IFN-γ (white and dark gray cartoons) is a homodimeric cytokine which binds two IFN-γR1 receptors (light gray ribbons) and two IFN-γR2 receptors (black ribbons). The IFN-γR1 binding sites within the IFN-γ molecule are termed Site Ia and Site Ib, whereas the IFN-γR2 binding sites within the IFN-γ molecule are termed Site IIa and Site IIb.

The present disclosure relates generally to the field of molecular biology immunology, and medicine, including compositions and methods for modulating IFN-γ-mediated signaling pathway in a subject in need thereof. Some embodiments of the disclosure relate to IFN-γ polypeptide variants that are modified to exhibit physical properties and activities that differ from unmodified and wild-type IFN-γ polypeptides. Nucleic acid molecules encoding these IFN-γ polypeptide variants also are provided. Also provided are methods of treatment and diagnosis using the IFN-γ polypeptide variants.

In some further embodiments of the disclosure, IFN-γ-mediated signaling is modulated via selective reduction of IFN-γ-binding to one of its two receptors, IFN-γR1 and IFN-γR2. More particularly, in some embodiments, the disclosure provides novel IFN-γ polypeptide variants with reduced binding affinity to interferon-gamma receptor subunit 1 (IFN-γR1) or interferon-gamma receptor subunit 2 (IFN-γR2) that completely or partially agonize the downstream signal transduction mediated through the respective IFN-γR1 or IFN-γR2 receptors. Some embodiments of the disclosure relate to compositions and methods useful for producing such IFN-γ polypeptide variants, as well as methods for the treatment of health diseases associated with perturbations of signal transduction mediated by IFN-γ.

As described in greater detail below, in order to attempt to engineer variants of IFN-γ that are clinically useful, the present disclosure provides for, inter alia, the determination of the crystal structure of the human IFN-γ in complex with its IFN-γR1 and IFN-γR2 receptors. In addition, using this structure as an engineering blueprint for how IFN-γ binds to its receptors, several mutated residues in IFN-γ have been engineered to impair either or both IFN-γR1 and IFN-γR2 binding, and created variants of IFN-γ that act as partial signaling agonists for STAT1-P, and biased agonists for downstream actions of IFN-γ. In particular, these IFN-γ variants exhibit a reduced capacity to upregulate PD-L1 expression, while retaining significant capacity to upregulate MHC class I expression. As described in greater detail below, several functional outputs of IFN-γ have been examined, including ENA78, EOTAXIN, G-CSF, HGF, IFN-b, IL-10, IL-12P70, IL-13, IL-15, IL-17F, IL-18, IL-1b, IL-2, IL-23, IL-27, IL-5, IL-7, IL-8, IL-9, IP-10, LEPTIN, LIF, MCP-3, MIG, PDGF-BB, RANTES, sCD40L, SCF, sFAS, sICAM-1, sVCAM-1, TGF-a, TGF-b, TNF-a, TNF-b, and VEGF-D; and were found to be differentially secreted compared to a control, as determined in a bead-based immunoassay cytokine secretion experiment. Without being bound to any particular theory, it is believed that these biased agonists also exhibit biases for other functional readouts of IFN-γ on many different responder cells. Non-limiting examples of cell surface markers suitable for the biased agonist approaches described herein include MHC Class I, PD-L1, MHC Class II (HLA-DR), CD40, CD86, CD80, CD107a, and CD69. The IFN-γ variants disclosed herein illustrate a novel approach to tune IFN-γ signaling for therapy. In particular, the structural information described herein informs the engineering of IFN-γ for desirable therapeutic properties. As discussed in greater detail below, the present disclosure provides, inter alia, (1) partial and biased IFN-γ agonist molecules and properties, (2) amino acid positions in the IFN-γR2 binding site of IFN-γ identified based on the crystal structure described herein, which has not been published previously, that can serve as mutational targets to create additional biased agonists. In particular, without being bound by theory, these amino acids, either mutated only on IFN-γR2 or in tandem with IFN-γR1 mutations, can define the target site on IFN-γ to design and create biased agonists. Thus, the crystal structure described herein allows for the creation of the IFN-γ biased agonists. In various embodiments of the disclosure, some of the biased agonist IFN-γ sequences contain mutations in some subset of these amino acids in the IFN-γR2 binding site of the IFN-γ molecule while others contain mutated residues within the IFN-γR1 binding site of the IFN-γ molecule.

The IFN-γ variants disclosed herein provide several advantages. The concept of biased agonists is very modular and versatile and, in principle, can have clinical utility in a wide range of immunotherapies. For example, while wild-type IFN-γ has not yet demonstrated utility in the clinical trials conducted to date, the partial and biased agonists (e.g., IFN-γ variants) disclosed herein, which decouple the downstream actions of IFN-γ, pave the way for use such IFN-γ variants in immunotherapy, for example in the treatment of cancer or other immune diseases including autoimmune diseases.

Definitions

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a"," "an"," and "the" include plural references unless the context clearly dictates otherwise. For example, the term "a cell" includes one or more cells, comprising mixtures thereof "A and/or B" is used herein to include all of the following alternatives: "A"," "B"," "A or B"," and "A and B".

The term "about"," as used herein, has its ordinary meaning of approximately. If the degree of approximation is not otherwise clear from the context, "about" means either within plus or minus 10% of the provided value, or rounded to the nearest significant figure, in all cases inclusive of the provided value. Where ranges are provided, they are inclusive of the boundary values.

The terms "administration" and "administering," as used herein, refer to the delivery of a bioactive composition or formulation by an administration route comprising, but not limited to, oral, intravenous, intra-arterial, intramuscular, intraperitoneal, subcutaneous, intramuscular, and topical administration, or combinations thereof. The term includes, but is not limited to, administering by a medical professional and self-administering.

The term "effective amount," "therapeutically effective amount," or "pharmaceutically effective amount" of a subject recombinant polypeptide of the disclosure generally refers to an amount sufficient for a composition to accomplish a stated purpose relative to the absence of the composition (e.g., achieve the effect for which it is administered, treat a disease, reduce a signaling pathway, or reduce one or more symptoms of a disease or health condition). An example of an "effective amount" is an amount sufficient to contribute to the treatment, prevention, or reduction of a symptom or symptoms of a disease, which could also be referred to as a "therapeutically effective amount." A "reduction" of a symptom means decreasing of the severity or frequency of the symptom(s), or elimination of the symptom (s). The exact amount of a composition including a "therapeutically effective amount" will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and Remington: *The Science and Practice of Pharmacy*, 20th Edition, 2003, Gennaro, Ed., Lippincott, Williams & Wilkins).

The term "operably linked"," as used herein, denotes a physical or functional linkage between two or more elements, e.g., polypeptide sequences or polynucleotide sequences, which permits them to operate in their intended fashion. For example, an operably linkage between a polynucleotide of interest and a regulatory sequence (for example, a promoter) is functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. Thus, a promoter is in operable linkage with a nucleic acid sequence if it can mediate transcription of the nucleic acid sequence. It should be understood that, operably linked elements may be contiguous or non-contiguous. In the context of a polypeptide, "operably linked" refers to a physical linkage (e.g., directly or indirectly linked) between amino acid sequences (e.g., different segments, modules, or domains) to provide for a described activity of the polypeptide. In the present disclosure, various segments, region, or domains of the recombinant polypeptides of the disclosure may be operably linked to retain proper folding, processing, targeting, expression, binding, and other functional properties of the recombinant polypeptides in the cell. Unless stated otherwise, various modules, domains, and segments of the recombinant polypeptides of the disclosure are operably linked to each other. Operably linked modules, domains, and segments of the multivalent polypeptides or multivalent antibodies of the disclosure may be contiguous or non-contiguous (e.g., linked to one another through a linker).

The term "percent identity," as used herein in the context of two or more nucleic acids or proteins, refers to two or more sequences or subsequences that are the same or have a specified percentage of nucleotides or amino acids that are the same (e.g., about 60% sequence identity, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm.nih.gov/BLAST. Such sequences are then said to be "substantially identical." This definition also refers to, or may be applied to, the complement of a test sequence. This definition also includes sequences that have deletions and/or additions, as well as those that have substitutions. Sequence identity typically exists over a region that is at least about 20 amino acids or nucleotides in length, or over a region that is 10-100 amino acids or nucleotides in length, or over the entire length of a given sequence.

If necessary, sequence identity can be calculated using published techniques and widely available computer programs, such as the GCS program package (Devereux et al, Nucleic Acids Res. 12:387, 1984), BLASTP, BLASTN, FASTA (Atschul et al., J. Molecular Biol. 215:403, 1990). Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof.

The term "pharmaceutically acceptable excipient" as used herein refers to any suitable substance that provides a pharmaceutically acceptable carrier, additive or diluent for administration of a compound(s) of interest to a subject. As such, "pharmaceutically acceptable excipient" can encompass substances referred to as pharmaceutically acceptable diluents, pharmaceutically acceptable additives, and pharmaceutically acceptable carriers. As used herein, the term "pharmaceutically acceptable carrier" includes, but is not limited to, saline, solvents, dispersion media, coatings, antibacterial and antifungal agents, isotonic and absorption delaying agents, and the like, compatible with pharmaceutical administration. Supplementary active compounds (e.g., antibiotics and additional therapeutic agents) can also be incorporated into the compositions.

The term "recombinant" or "engineered" nucleic acid molecule as used herein, refers to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule can be one which: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) includes conjoined nucleotide sequences that are not conjoined in nature; 3) has been engineered using molecular cloning techniques such that it lacks one or more nucleotides with respect to the naturally occurring nucleic acid molecule sequence; and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. Another non-limiting example of a recombinant nucleic acid and recombinant protein is an IFN-γ polypeptide variant as disclosed herein.

As used herein, a "subject" or an "individual" or a "patient" includes animals, such as human (e.g., human subjects) and non-human animals. Thus, the subject can be a human patient or an individual who has or is suspected of having a disease of interest (e.g., cancer) and/or one or more symptoms of the disease. The subject can also be an individual who is diagnosed with a risk of the condition of interest at the time of diagnosis or later. The term "non-human animals" includes all vertebrates, e.g., mammals, e.g., rodents, e.g., mice, and non-mammals, such as non-human primates, e.g., sheep, dogs, cows, chickens, amphibians, reptiles, etc.

As used herein, the term "variant" of an IFN-γ polypeptide refers to a polypeptide in which one or more amino acid substitutions, deletions, and/or insertions are present as compared to the amino acid sequence of a reference IFN-γ polypeptide. As such, the term "IFN-γ polypeptide variant" includes naturally occurring allelic variants or alternative splice variants of an IFN-γ polypeptide. For example, a polypeptide variant includes the substitution of one or more amino acids in the amino acid sequence of a parent polypeptide with a similar or homologous amino acid(s) or a dissimilar amino acid(s). There are many scales on which amino acids can be ranked as similar or homologous. (Gunnar von Heijne, *Sequence Analysis in Molecular Biology*, p. 123-39 (Academic Press, New York, NY 1987.) Exemplary variants include alanine substitutions at one or more of amino acid positions. Other exemplary substitutions include conservative substitutions that have little or no effect on the overall net charge, polarity, or hydrophobicity of the polypeptide.

As will be understood by one having ordinary skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

The term "vector" is used herein to refer to a nucleic acid molecule or sequence capable of transferring or transporting another nucleic acid molecule. The transferred nucleic acid molecule is generally linked to, e.g., inserted into, the vector nucleic acid molecule. Generally, a vector is capable of replication when associated with the proper control elements. The term "vector" includes cloning vectors and expression vectors, as well as viral vectors and integrating vectors. An "expression vector" is a vector that includes a regulatory region, thereby capable of expressing DNA sequences and fragments in vitro and/or in vivo. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses. In some embodiments, a vector is a gene delivery vector. In some embodiments, a vector is used as a gene delivery vehicle to transfer a gene into a cell.

It is understood that aspects and embodiments of the disclosure described herein include "comprising," "consisting," and "consisting essentially of" aspects and embodiments. As used herein, "comprising" is synonymous with "including," "containing," or "characterized by," and is inclusive or open-ended and does not exclude additional, unrecited elements or method steps. As used herein, "consisting of" excludes any elements, steps, or ingredients not specified in the claimed composition or method. As used herein, "consisting essentially of" does not exclude materials or steps that do not materially affect the basic and novel characteristics of the claimed composition or method. Any recitation herein of the term "comprising", particularly in a description of components of a composition or in a description of steps of a method, is understood to encompass those compositions and methods consisting essentially of and consisting of the recited components or steps.

Headings, e.g., (a), (b), (i) etc., are presented merely for ease of reading the specification and claims. The use of headings in the specification or claims does not require the steps or elements be performed in alphabetical or numerical order or the order in which they are presented.

Interferon Gamma

IFN-γ is a cytokine that is secreted in response to viral infections or cancerous growths. IFN-γ regulates T-cell class I and II MHC antigen expression, Fc receptors, and macrophages (Stark et al., Annu Rev Biochem, 67, 227-264, 1998). IFN-γ signals through a multimeric receptor complex consisting of two different chains: the IFN-γ receptor binding subunit (IFN-γR, IFN-γR1), and a transmembrane accessory factor (AF-1, IFN-γR2). Interaction between the components of the IFN-γ receptor complex has been extensively documented (Kotenko et al., J Biol Chem, 270, 20915-20921, 1995). The IFN-γ signaling complex is formed upon ligand-driven dimerization of the IFN-γ receptors (Farrar and Schreiber, Annu Rev Immunol 11:571-611, 1993) composed of two IFN-γR1 molecules, which bind with high affinity, and two IFN-γR2 molecules, which bind with low affinity. The inherent low affinity of IFN-γR2 for the 2:2 IFN-γ/IFN-γR1 intermediate complex has hindered efforts to crystallize the complete hexameric signaling complex. As described in further detailed below, some embodiments of the disclosure provide a higher affinity IFN-γR1 to stabilize interactions with IFN-γR2, thereby, enabling determination of the 2:2:2 IFN-γ/IFN-γR1/IFN-γR2 structure at 3.1 angstroms. Using insights from the crystal structure, several IFN-γ variants were generated to determine the contribution of each step of complex formation on signaling and function. The structure-function studies described herein demonstrates that the IFN-γR1 receptor provides sensitivity, while IFN-γR2 is essential for achieving the maximal potency of signaling and IFN-γ response. The experiments described herein demonstrated that the engineered IFN-γ molecules provide an avenue for differentiating IFN-γ activity through tuning of the intensity of the cell signal f cell signaling mediated by IFN-γ receptor(s). As one example, one partial agonist, GIFN4, fully upregulates class I MHC antigen expression while limiting PD-L1 expression on both lung cancer cells and blood purified dendritic cells. The experimental results described in the present disclosure provide new insights on IFN-γ ligand-receptor interactions, disease associated mutations which disrupt these interactions, and new molecules for studying IFN-γ mediated signaling and disease.

IFN-γ has been shown to have a unique role among the three IFN families, in that, in addition to possessing antiviral activity, IFN-γ is a potent immunomodulatory cytokine (Pace et al., J. Immunol. 134: 977-981, 1985). The cloning of IFN-γ (Gray and Goeddel, Nature, 298, 859-863, 1982; and Gray et al., Nature, 295, 503-508, 1982) facilitated the study of IFN-γ signaling and activity of the wild-type molecule through the use of recombinant proteins. Despite the structure of the IFN-γ homodimer being the first IFN to be visualized (Ealick et al., Science 252 698-702, 1991), the structure of the complete extracellular hexameric (2:2:2 IFN-γ/IFN-γR1/IFN-γR2) signaling complex is the last of the IFN superfamily structures to be solved.

As used herein, an IFN-γ polypeptide refers to any interferon-γ polypeptide, including but not limited to, a recombinantly produced polypeptide, synthetically produced polypeptide, and IFN-γ isolated from cells or tissues, such as from T-lymphocytes and NK cells and other sources. As isolated from any source or as produced, IFN-γ polypeptides can be heterogeneous in length and typically range from 124 to 146 amino acids in length. Heterogeneity is typically observed at both termini. Generally, heterogeneity exists at the N-terminus due to post-translational removal of Cys-Tyr-Cys amino acids and at the C-terminus due to variable proteolytic processing. Heterogeneity also can result due to N-glycosylation of the polypeptide. Heterogeneity of IFN-γ polypeptides can differ depending on the source of the IFN-γ polypeptide. Hence reference to IFN-γ polypeptides refers to the heterogeneous population as produced or isolated. When a homogeneous preparation is intended, it will be so-stated. Reference to an IFN-γ polypeptide herein is to its monomeric or dimeric form, as appropriate.

For example, the term "human IFN-γ" (hIFN-γ) as used herein includes IFN-γ, allelic variant isoforms, synthetic molecules, proteins isolated from human tissue and cells, and modified forms thereof. Exemplary unmodified mature human IFN-γ polypeptides include, but are not limited to, unmodified and wild-type IFN-γ polypeptide (such as the polypeptide comprising the sequence set forth in SEQ ID NO: 1) and the unmodified and wild-type precursor IFN-γ polypeptide that includes a signal peptide.

The term IFN-γ polypeptide also includes allelic or species variants of IFN-γ, and truncated forms or fragments thereof which retain substantial IFN-γ activity, or retain at least one activity of the full-length mature IFN-γ polypeptide from which the truncated forms or fragments were derived. The term IFN-γ includes homologous polypeptides from different species including, but not limited to animals, including humans and non-human species, such as other mammals. As with human IFN-γ, non-human IFN-γ also includes variants of heterogeneous lengths or fragments or portions of IFN-γ that are of sufficient length or include appropriate regions to retain at least one activity of the full-length mature polypeptide from which the variant was derived.

As used herein, an IFN-γ dimer refers to a combination of two monomeric IFN-γ polypeptides having the same or a different number of amino acids and/or different sequence of amino acids. For purposes herein, the first monomer of a dimer is designated "chain A" and the second monomer of the dimer is designated "chain B." Typically, the dimeric form of the polypeptide contains two monomers associated via non-covalent interactions, such as hydrophobic interactions, hydrogen bonds, van der Waals and other such interactions. Such IFN-γ dimers can form spontaneously when expressed and typically form spontaneously, such as, for example, as occurs using the methods of protein production described herein. IFN-γ dimers also can be produced as fusion proteins, such as in the form of a single chain dimeric IFN-γ polypeptide comprised of the same or different monomers, optionally providing a polypeptide linker sequence between the monomers.

Compositions of the Disclosure

Interferon-Gamma (IFN-γ) Polypeptide Variants

In one aspect, provided herein are novel IFN-γ polypeptide variants that confer a reduction in the intensity of cell signaling mediated by IFN-γ receptor(s) as compared to a wild-type IFN-γ polypeptide. These IFN-γ polypeptide variants are termed IFN-γ "partial agonists." In some embodiments, the disclosed IFN-γ polypeptide variants possess reduced binding affinity to at least one of its native receptors, e.g., interferon-gamma receptor subunit 1 (IFN-γR1) and/or interferon-gamma receptor subunit 2 (IFN-γR2), such that binding of the IFN-γ polypeptide variants to one or more of the receptors results in a complete or partial agonism of the downstream signal mediated through such receptor. In some embodiments, the disclosed IFN-γ partial agonists confer a reduction in the intensity of cell signaling mediated by IFN-γR1 relative to the response observed for a wild-type IFN-γ. In some embodiments, the disclosed IFN-γ partial agonists confer a reduced intensity of cell signaling mediated by IFN-γR2 compared to the response observed for a wild-type IFN-γ. In some embodiments, the disclosed IFN-γ partial agonists confer a reduced intensity of cell signaling mediated by both IFN-γR1 and IFN-γR2.

In some embodiments, the IFN-γ polypeptide variants of the disclosure include one or more amino acid substitutions at amino acid positions located at the IFN-γR1 binding interface of the IFN-γ polypeptide. As will be understood by one skilled in the art, a binding interface of an IFN-γ polypeptides disclosed herein includes those amino acid residues in the IFN-γ polypeptide which interact with one or more amino acid residues in the interface of a second polypeptide, e.g., IFN-γR1 or IFN-γR2. As such, a binding interface of an IFN-γ complex as described herein includes the set of amino acids that attach two polypeptide chains in a protein structure of the IFN-γ complex by non-covalent interactions. In some embodiments, the IFN-γ polypeptide variants of the disclosure include one or more amino acid substitutions at amino acid positions located at the IFN-γR2 binding interface of the IFN-γ polypeptide. Additional information regarding the IFN-γR1 binding interface and the IFN-γR2 binding interface can be found in, e.g., Nuara A A et al., Proc Natl Acad Sci USA February 12; 105(6): 1861-1866, 2008; Walter M R et al., Nature. 376:230-235, 1995; and Randal M and Kossiakoff A A, Structure (London) 9:155-163, 2001.

In some embodiments, provided herein is a recombinant polypeptide comprising a first amino acid sequence (e.g., chain A) having at least 95%, at least 96%, at least 97%, at least 98%, at least 99% sequence identity to identity to an IFN-γ polypeptide having the amino acid sequence of SEQ ID NO: 1, and further including one or more amino acid substitutions at amino acid positions located at the IFN-γR2 binding interface of the IFN-γ polypeptide. In some embodiments, the recombinant polypeptide comprising a first amino acid sequence having at least 95%, at least 96%, at least 97%, at least 98%, at least 99% sequence identity to identity to an IFN-γ polypeptide having the amino acid sequence of SEQ ID NO: 1, and further including one or more amino acid substitutions at amino acid positions located at the IFN-γR2 binding interface of the IFN-γ polypeptide, and retains substantial IFN-γ activity or at least one activity of the IFN-γ polypeptide having the amino acid sequence of SEQ ID NO: 1.

As will be understood by one skilled in the art, the phrase "in a position or positions corresponding to an amino acid residue" used in reference to a polypeptide refers to amino acid positions that are determined to correspond to one another based on sequence and/or structural alignments with a specified reference protein. For example, in a position corresponding to an amino acid position of human IFN-γ polypeptide set forth as SEQ ID NO: 1 can be determined empirically by aligning the sequence of amino acids set forth in SEQ ID NO: 1 with a particular IFN-γ polypeptide of interest. Corresponding positions can be determined by such alignment by one of skill in the art using manual alignments or by using the numerous alignment programs available (for example, BLASTP). Corresponding positions also can be based on structural alignments, for example by using computer simulated alignments of protein structure. Recitation that amino acids of a polypeptide correspond to amino acids in a disclosed sequence refers to amino acids identified upon alignment of the polypeptide with the disclosed sequence to maximize identity or homology (where conserved amino acids are aligned) using a standard alignment algorithm, such as the GAP algorithm. As used herein, "at a position corresponding to" refers to a position of interest (e.g., base number or residue number) in a nucleic acid molecule or protein relative to the position in another reference nucleic acid molecule or protein. The position of interest to the position in another reference protein can be in, for example, a precursor protein, an allelic variant, a heterologous protein, an amino acid sequence from the same protein of another species, etc. By aligning the sequences of IFN-γ polypeptides derived from different species, one skilled in the art can identify corresponding residues, using conserved and identical amino acid residues as guides. Corresponding positions can be determined by comparing and aligning sequences to maximize the number of matching nucleotides or residues, for example, such that identity between the sequences is greater than 95%, preferably greater than 96%, more preferably greater than 97%, even more preferably greater than 98% and most preferably greater than 99%. The position of interest is then given the number assigned in the reference nucleic acid molecule.

In some embodiments, the polypeptide includes a first amino acid sequence having at least 95%, at least 96%, at least 97%, at least 98%, at least 99% sequence identity to an IFN-γ polypeptide having the amino acid sequence of SEQ ID NO: 1, and further includes one or more amino acid substitutions at amino acid positions located at the IFN-γR2 binding interface of the IFN-γ polypeptide. Generally, the one or more amino acid substitutions can be at any amino acid positions at the IFN-γR2 binding interface of the IFN-γ polypeptide. Non-limiting examples of amino acid positions at the IFN-γR2 interaction interface of an IFN-γ polypeptide disclosed herein include amino acid positions corresponding to Q1, D2, P3, K6, Q64, Q67, K68, E71, T72, K74, E75, D76, N78, V79, K80, N83, S84, K86, R89, and D90 of the amino acid sequence of SEQ ID NO: 1. In some embodiments, the first amino acid sequence of the disclosed polypeptide includes at least 1, 2, 3, 4, 5, 6, 7, 8, 9, 10, 11, 12, 13, 14, 15, 16, 17, 18, 19, or 20 amino acid substitutions at amino acid positions located at the IFN-γR2 binding interface of the IFN-γ polypeptide. In some embodiments, the first amino acid sequence of the disclosed polypeptide includes about 1 to 5, about 2 to 10, about 5 to 15, about 10 to 20, about 15 to 20, about 2 to 8, about 3 to 10, or about 4 to 12 amino acid substitutions at amino acid positions located at the IFN-γR2 binding interface of the IFN-γ polypeptide. In some embodiments, the first amino acid sequence of the disclosed polypeptide includes one, two, three, four, five, six, seven, eight, nine, or ten amino acid substitutions at amino acid positions located at the IFN-γR2 binding interface of the IFN-γ polypeptide.

In some embodiments, the polypeptide includes a first amino acid sequence having at least 95% identity to an IFN-γ polypeptide having the amino acid sequence of SEQ ID NO: 1, and further including at least one amino acid substitution at a position corresponding to an amino acid residue selected from the group consisting of Q1, D2, P3, K6, Q64, Q67, K68, E71, T72, K74, E75, D76, N78, V79, K80, N83, S84, K86, R89, and D90 of SEQ ID NO: 1, and any combination thereof. In some embodiments, the polypeptide includes a first amino acid sequence having at least 95%, at least 96%, at least 97%, at least 98%, at least 99% sequence identity to an IFN-γ polypeptide having the amino acid sequence of SEQ ID NO: 1, and further including at least one amino acid substitution at a position corresponding to an amino acid residue selected from the group consisting of Q1, D2, P3, K6, Q64, Q67, K68, E71, T72, K74, E75, D76, N78, V79, K80, N83, S84, K86, R89, and D90 of SEQ ID NO: 1, and any combination thereof. In some embodiments, the polypeptide includes a first amino acid sequence having 100% sequence identity to the amino acid sequence of SEQ ID NO: 1, and further including at least one amino acid substitution at a position corresponding to an amino acid residue selected from the group consisting of Q1, D2, P3, K6, Q64, Q67, K68, E71, T72, K74, E75, D76, N78, V79, K80, N83, S84, K86, R89, and D90 of SEQ ID NO: 1, and any combination thereof. In some embodiments, the at least one amino acid substitution is at a position corresponding to an amino acid residue selected from the group consisting of K74, E75, and N83 of SEQ ID NO: 1, and any combination thereof. In some embodiments, the at least one amino acid substitution is at a position corresponding to the amino acid residue K74 of SEQ ID NO: 1. In some embodiments, the at least one amino acid substitution is a Lys-to-Ala substitution (K74A). In some embodiments, the at least one amino acid substitution is at a position corresponding to the amino acid residue E75 of SEQ ID NO: 1. In some embodiments, the at least one amino acid substitution is a Glu-to-Tyr substitution (E75Y). In some embodiments, the at least one amino acid substitution is at a position corresponding to the amino acid residue N83 of SEQ ID NO: 1. In some embodiments, the at least one amino acid substitution is an Asn-to-Arg substitution (N83R). In some embodiments, at least one amino acid substitution in the first amino acid sequence is at positions corresponding to K74A, E75Y, and N83R substitutions of SEQ ID NO: 1.

In some embodiments, the first amino acid sequence further includes one or more amino acid substitutions at amino acid positions located at the IFN-γR1 binding interface of the IFN-γ polypeptide. Generally, the one or more amino acid substitutions can be at any amino acid positions at the IFN-γR1 binding interface of the IFN-γ polypeptide. Non-limiting examples of amino acid positions at the IFN-γR1 binding interface of an IFN-γ polypeptide disclosed herein include amino acid positions corresponding to Q1, D2, Y4, V5, E9, K12, A17, G18, H19, S20, D21, V22, A23, D24, N25, G26, T27, L28, L30, K34, K37, K108, H111, E112, I114, Q115, A118, E119, A124, K125 of the amino acid sequence of SEQ ID NO: 1. In some embodiments, the first amino acid sequence of the disclosed polypeptide includes at least 1, 2, 3, 4, 5, 6, 7, 8, 9, 10, 11, 12, 13, 14, 15, 16, 17, 18, 19, or 20 amino acid substitutions at amino acid positions located at the IFN-γR1 binding interface of the IFN-γ polypeptide. In some embodiments, the first amino acid sequence of the disclosed polypeptide includes about 1 to 5, about 2 to 10, about 5 to 15, about 10 to 20, about 15 to 20, about 2 to 8, about 3 to 10, or about 4 to 12 amino acid substitutions at amino acid positions located at the IFN-γR1 binding interface of the IFN-γ polypeptide. In some embodiments, the first amino acid sequence of the disclosed polypeptide includes one, two, three, four, five, six, seven, eight, nine, or ten amino acid substitutions at amino acid positions at the IFN-γR1 binding interface of the IFN-γ polypeptide. In some embodiments, the one or more amino acid substitutions at the IFN-γR1 binding interface of an IFN-γ polypeptide disclosed herein include amino acid substitutions corresponding to A23, D24, N25, and H111 of the sequence of SEQ ID NO: 1. In some embodiments, the one or more amino acid substitutions in the first amino acid sequence of an IFN-γ polypeptide disclosed herein is at a position corresponding to an amino acid residue selected from the group consisting of Q1, D2, Y4, V5, E9, K12, A17, G18, H19, S20, D21, V22, A23, D24, N25, G26, T27, L28, L30, K34, and K37 of SEQ ID NO: 1, and any combination thereof.

In some embodiments, the polypeptide of the disclosure further includes a second amino acid sequence (e.g., chain B) having at least 95% identity to an IFN-γ polypeptide having the amino acid sequence of SEQ ID NO: 1, wherein the second amino acid sequence is operably linked to the first amino acid sequence. In some embodiments, the second amino acid sequence of the disclosed polypeptide has at least 95% identity to an IFN-γ polypeptide having the amino acid sequence of SEQ ID NO: 1 and retains substantial IFN-γ activity or at least one activity of the IFN-γ polypeptide having the amino acid sequence of SEQ ID NO: 1. In some embodiments, the second amino acid sequence of the disclosed polypeptide has at least 95%, at least 96%, at least 97%, at least 98%, at least 99% sequence identity to an IFN-γ polypeptide having the amino acid sequence of SEQ ID NO: 1. In some embodiments, the second amino acid sequence of the disclosed polypeptide has 100% sequence identity to an IFN-γ polypeptide having the amino acid sequence of SEQ ID NO: 1. In some embodiments, the second amino acid sequence includes one or more amino acid substitutions at amino acid positions located at the IFN-γR2 binding interface of the IFN-γ polypeptide and retains at least one activity of the IFN-γ polypeptide having the amino acid sequence of SEQ ID NO: 1. Generally, the one or more amino acid substitutions in the second amino acid sequence can correspond to any amino acid positions at the IFN-γR2 binding interface of the IFN-γ polypeptide. Non-limiting examples of amino acid positions in the second amino acid sequence at the IFN-γR2 binding interface of an IFN-γ polypeptide disclosed herein include amino acid positions corresponding to Q1, D2, P3, K6, Q64, Q67, K68, E71, T72, K74, E75, D76, N78, V79, K80, N83, S84, K86, R89, and D90 of the amino acid sequence of SEQ ID NO: 1. In some embodiments, the second amino acid sequence of the disclosed polypeptide includes at least 1, 2, 3, 4, 5, 6, 7, 8, 9, 10, 11, 12, 13, 14, 15, 16, 17, 18, 19, or 20 amino acid substitutions at amino acid positions located at the IFN-γR2 binding interface of the IFN-γ polypeptide. In some embodiments, the second amino acid sequence of the disclosed polypeptide includes about 1 to 5, about 2 to 10, about 5 to 15, about 10 to 20, about 15 to 20, about 2 to 8, about 3 to 10, or about 4 to 12 amino acid substitutions at amino acid positions located at the IFN-γR2 binding interface of the IFN-γ polypeptide.

In some embodiments, the second amino acid sequence of the disclosed IFN-γ polypeptide has at least 95% identity to an IFN-γ polypeptide having the amino acid sequence of SEQ ID NO: 1, and further including at least one amino acid substitution at a position corresponding to an amino acid residue selected from the group consisting of Q1, D2, P3, K6, Q64, Q67, K68, E71, T72, K74, E75, D76, N78, V79, K80, N83, S84, K86, R89, and D90 of SEQ ID NO: 1, and any combination thereof. In some embodiments, the second amino acid sequence of the disclosed polypeptide has at least 95%, at least 96%, at least 97%, at least 98%, at least 99% sequence identity to an IFN-γ polypeptide having the amino acid sequence of SEQ ID NO: 1, and further including at least one amino acid substitution at a position corresponding to an amino acid residue selected from the group consisting of Q1, D2, P3, K6, Q64, Q67, K68, E71, T72, K74, E75, D76, N78, V79, K80, N83, S84, K86, R89, and D90 of the sequence of SEQ ID NO: 1, and any combination thereof. In some embodiments, the second amino acid sequence of the disclosed polypeptide has 100% sequence identity to the amino acid sequence of SEQ ID NO: 1, and further including at least one amino acid substitution at a position corresponding to an amino acid residue selected from the group consisting of Q1, D2, P3, K6, Q64, Q67, K68, E71, T72, K74, E75, D76, N78, V79, K80, N83, S84, K86, R89, and D90 of SEQ ID NO: 1, and any combination thereof. In some embodiments, the at least one amino acid substitution in the second amino acid sequence is at a position corresponding to an amino acid residue selected from the group consisting of K74, E75, and N83 of SEQ ID NO: 1, and any combination thereof. In some embodiments, the at least one amino acid substitution in the second amino acid sequence is at a position corresponding to the amino acid residue K74 of SEQ ID NO: 1. In some embodiments, the at least one amino acid substitution in the second amino acid sequence is a Lys-to-Ala substitution (K74A). In some embodiments, the at least one amino acid substitution in the second amino acid sequence is at a position corresponding to the amino acid residue E75 of SEQ ID NO: 1. In some embodiments, the at least one amino acid substitution in the second amino acid sequence is a Glu-to-Tyr substitution (E75Y). In some embodiments, the at least one amino acid substitution in the second amino acid sequence is at a position corresponding to the amino acid residue N83 of SEQ ID NO: 1. In some embodiments, the at least one amino acid substitution in the second amino acid sequence is an Asn-to-Arg substitution (N83R). In some embodiments, at least one amino acid substitution in the second amino acid sequence is at positions corresponding to K74A, E75Y, and N83R substitutions of SEQ ID NO: 1.

In some embodiments, the second amino acid sequence further includes one or more amino acid substitutions at amino acid positions located at the IFN-γR1 binding interface of the IFN-γ polypeptide. Generally, the one or more amino acid substitutions in the second amino acid sequence can be at any amino acid positions located at the IFN-γR1 binding interface of an IFN-γ polypeptide disclosed herein, and include amino acid positions corresponding to Q1, D2, Y4, V5, E9, K12, A17, G18, H19, 520, D21, V22, A23, D24, N25, G26, T27, L28, L30, K34, K37, K108, H111, E112, I114, Q115, A118, E119, A124, K125 of the amino acid sequence of SEQ ID NO: 1. In some embodiments, the second amino acid sequence includes at least 1, 2, 3, 4, 5, 6, 7, 8, 9, 10, 11, 12, 13, 14, 15, 16, 17, 18, 19, or 20 amino acid substitutions at amino acid positions located at the IFN-γR1 binding interface of the IFN-γ polypeptide and retains at least one activity of the IFN-γ polypeptide having the amino acid sequence of SEQ ID NO: 1. In some embodiments, the second amino acid sequence includes about 1 to 5, about 2 to 10, about 5 to 15, about 10 to 20, about 15 to 20, about 2 to 8, about 3 to 10, or about 4 to 12 amino acid substitutions at amino acid positions located at the IFN-γR1 binding interface of the IFN-γ polypeptide. In some embodiments, the one or more amino acid substitutions in the second amino acid sequence of an IFN-γ polypeptide disclosed herein is at a position corresponding to an amino acid residue selected from the group consisting of K108, H111, E112, I114, Q115, A118, E119, A124, and K125 of SEQ ID NO: 1, an any combination thereof. In some embodiments, the one or more amino acid substitutions in the second amino acid sequence of an IFN-γ polypeptide disclosed herein include amino acid substitutions corresponding to A23, D24, N25, and H111 of the sequence of SEQ ID NO: 1.

In some embodiments, the first amino acid sequence is directly linked to the second amino acid sequence. In some embodiments, the first amino acid sequence is directly linked to a second amino acid sequence via at least one covalent bond. In some embodiments, a first amino acid sequence is directly linked to the second amino acid sequence via at least one peptide bond. In some embodiments, the C-terminal amino acid of the first amino acid sequence can be operably linked to the N-terminal amino acid of the second amino acid sequence. Alternatively, the N-terminal amino acid of the first amino acid sequence can be operably linked to the C-terminal amino acid of the second amino acid sequence.

In some embodiments, the recombinant polypeptides disclosed herein have no intervening amino acid residues between the sequences of the first and second amino acid sequences. In some embodiments, the first amino acid sequence of the recombinant polypeptide disclosed herein is operably linked to the second amino acid sequence via a linker. There is no particular limitation on the linkers that can be used in the polypeptides described herein. In some embodiments, the linker is a synthetic compound linker such as, for example, a chemical cross-linking agent. Non-limiting examples of suitable cross-linking agents that are commercially available include N-hydroxysuccinimide (NHS), disuccinimidylsuberate (DSS), bis(sulfosuccinimidyl)suberate (BS3), dithiobis(succinimidylpropionate) (DSP), dithiobis(sulfosuccinimidylpropionate) (DTSSP), ethyleneglycol bis(succinimidylsuccinate) (EGS), ethyleneglycol bis(sulfosuccinimidylsuccinate) (sulfo-EGS), disuccinimidyl tartrate (DST), disulfosuccinimidyl tartrate (sulfo-DST), bis[2-(succinimidooxycarbonyloxy)ethyl]sulfone (BSOCOES), and bis[2-(sulfosuccinimidooxycarbonyloxy)ethyl]sulfone (sulfo-BSOCOES). Other examples of alterative structures and linkages suitable for the recombinant polypeptides of the disclosure include those described in Spiess et al., Mol. Immunol. 67:95-106, 2015.

In some embodiments, the first amino acid sequence of the polypeptide disclosed herein is operably linked to the second amino acid sequence via a linker polypeptide sequence (e.g., peptidal linkage). In principle, there are no particular limitations to the length and/or amino acid composition of the linker polypeptide sequence. In some embodiments, any arbitrary single-chain peptide comprising about 1 to 100 amino acid residues (e.g., 2, 3, 4, 5, 6, 7, 8, 9, 10, 11, 12, 13, 14, 15, 16, 17, 18, 19, 20, etc. amino acid residues) can be used as a peptide linker. In some embodiments, the linker polypeptide sequence includes about 5 to 50, about 10 to 60, about 20 to 70, about 30 to 80, about 40 to 90, about 50 to 100, about 60 to 80, about 70 to 100, about 30 to 60, about 20 to 80, about 30 to 90 amino acid residues. In some embodiments, the linker polypeptide sequence includes about 1 to 10, about 5 to 15, about 10 to 20, about 15 to 25, about 20 to 40, about 30 to 50, about 40 to 60, about 50 to 70 amino acid residues. In some embodiments, the linker polypeptide sequence includes about 40 to 70, about 50 to 80, about 60 to 80, about 70 to 90, or about 80 to 100 amino acid residues. In some embodiments, the linker polypeptide sequence includes about 1 to 10, about 5 to 15, about 10 to 20, about 15 to 25 amino acid residues.

In some embodiments, the length and amino acid composition of the linker polypeptide sequence can be optimized to vary the orientation and/or proximity of the first and the second amino acid sequences to one another to achieve a desired activity of the disclosed recombinant polypeptides, e.g., IFN-γ polypeptide variants disclosed herein. In some embodiments, the orientation and/or proximity of the first and the second amino acid sequences to one another can be varied as a "tuning" tool to achieve a tuning effect that would enhance or reduce the binding affinity of the IFN-γ polypeptide variant to one or more of its target(s) such as, for example, its binding affinity to interferon-gamma receptor subunit 1 (IFN-γR1) and/or interferon-gamma receptor subunit 2 (IFN-γR2). In some embodiments, the orientation and/or proximity of the first and the second amino acid sequences to one another can be optimized to create a partial agonist to full agonist versions of the IFN-γ polypeptide variant. In certain embodiments, the linker contains only glycine and/or serine residues (e.g., glycine-serine linker). Examples of such peptide linkers include: Gly, Ser; Gly Ser; Gly Gly Ser; Ser Gly Gly; Gly Gly Gly Ser; Ser Gly Gly Gly; Gly Gly Gly Gly Ser; Ser Gly Gly Gly Gly; Gly Gly Gly Gly Gly Ser; Ser Gly Gly Gly Gly Gly; Gly Gly Gly Gly Gly Gly Ser; Ser Gly Gly Gly Gly Gly Gly; (Gly Gly Gly Gly Ser)n, wherein n is an integer of one or more; and (Ser Gly Gly Gly Gly)n, wherein n is an integer of one or more. In some embodiments, the linker polypeptides are modified such that the amino acid sequence GSG (that occurs at the junction of traditional Gly/Ser linker polypeptide repeats) is not present. For example, in some embodiments, the polypeptide linker includes an amino acid sequence selected from the group consisting of: (GGGXX)nGGGGS and GGGGS(XGGGS)n, where X is any amino acid that can be inserted into the sequence and not result in a polypeptide comprising the sequence GSG, and n is an integer from 0 to 4. In some embodiments, the sequence of a linker peptide is $(GGGX_1X_2)$nGGGGS and $X_1$ is P and $X_2$ is S and n is an integer from 0 to 4. In some other embodiments, the sequence of a linker polypeptide is $(GGGX_1X_2)$nGGGGS and $X_i$ is G and $X_2$ is Q and n is an integer from 0 to 4. In some other embodiments, the sequence of a linker polypeptide is $(GGGX1X_2)$nGGGGS and $X_1$ is G and $X_2$ is A and n is an integer from 0 to 4. In yet some other embodiments, the sequence of a linker polypeptide is GGGGS(XGGGS)n, and X is P and n is an integer from 0 to 4. In some embodiments, a linker polypeptide of the disclosure comprises or consists of the amino acid sequence $(GGGGA)_2$GGGGS. In some embodiments, a linker polypeptide comprises or consists of the amino acid sequence $(GGGGQ)_2$GGGGS. In another embodiment, a linker polypeptide comprises or consists of the amino acid sequence $(GGGPS)_2$GGGGS. In another embodiment, a linker polypeptide comprises or consists of the amino acid sequence GGGGS $(PGGGS)_2$. In yet a further embodiment, a linker polypeptide comprises or consists of the amino acid sequence set forth in SEQ ID NO: 6.

It will be appreciated by one of ordinary skill in the art upon reading this disclosure that the polypeptide linker sequence described herein can be an uncleavable sequence or a cleavable sequence such as, e.g., a consensus cleavage site for protease. Accordingly, in some embodiments of the disclosure, the polypeptide linker sequence is a cleavable linker sequence. In some embodiments, the cleavable linker sequence comprises one or more proteolytic cleavage sites. In some embodiments, the one or more proteolytic cleavage sites are positioned within the sequence of the cleavable linker and/or flanking at either end of the cleavable linker. Generally, any proteolytic cleavage sites known in the art can be incorporated into the polypeptides of the disclosure and can be, for example, proteolytic cleavage sequences that are cleaved post-production by a protease. Further suitable proteolytic cleavage sites also include proteolytic cleavage sequences that can be cleaved following addition of an external protease. In some embodiments, at least one of the one or more proteolytic cleavage sites can be cleaved by a protease selected from the group consisting of thrombin, PreScission™ protease, and tobacco etch virus (TEV) protease. In some embodiments, at least one of the one or more proteolytic cleavage sites can be cleaved by an endopeptidase, which is sometimes referred to as endoproteinase or proteolytic peptidase that breaks peptide bonds of nonterminal amino acids (i.e., within the molecule), in contrast to exopeptidase, which breaks peptide bonds from end-pieces of terminal amino acids. Endopeptidases suitable for the disclosed antibodies include, but are not limited to trypsin, chymotrypsin, elastase, thermolysin, pepsin, glutamyl endopeptidase, or neprilysin.

In some embodiments, the polypeptides of the disclosure include an autoprotease peptide operably linked downstream to the first amino acid sequence and upstream to the second amino acid sequence. As used herein the term "autoprotease" refers to a "self-cleaving" peptide that possesses autoproteolytic activity and is capable of cleaving itself from a larger polypeptide moiety. First identified in the foot-and-mouth disease virus (FMDV), a member of the picornavirus group, several autoproteases have been subsequently identified such as, for example, "2A like" peptides from equine rhinitis A virus (E2A), porcine teschovirus-1 (P2A) and *Thosea asigna* virus (T2A), and their activities in proteolytic cleavage have been shown in various in vitro and in vivo eukaryotic systems. As such, the concept of autoproteases is available to one of skill in the art with many naturally occurring autoprotease systems have been identified. Well studied autoprotease systems are e.g. viral proteases, developmental proteins (e.g. HetR, Hedgehog proteins), RumA autoprotease domain, UmuD, etc.). Non-limiting examples of autoprotease peptide sequences suitable for the compositions and methods of the present disclosure include the peptide sequences from porcine teschovirus-1 2A (P2A), a foot-and-mouth disease virus (FMDV) 2A (F2A), an Equine Rhinitis A Virus (ERAV) 2A (E2A), a *Thosea asigna* virus 2A (T2A), a cytoplasmic polyhedrosis virus 2a (BmCPV2A), a Flacherie Virus 2A (BmIFV2A), or a combination thereof.

In some embodiments of the disclosure, the recombinant IFN-γ polypeptide of the disclosure is a chimeric polypeptide (e.g., fusion polypeptide) comprising a first amino acid sequence operably linked to a second amino acid sequence with which it is not naturally linked. The first and second amino acid sequences may normally exist as separate proteins that are brought together in the chimeric polypeptide or they may normally exist in the same protein but are placed in a new arrangement in the chimeric polypeptide. One of ordinary skill in the art will readily understand that the chimeric IFN-γ polypeptides disclosed herein may be created, for example, by chemical synthesis (e.g., synthetic polypeptides), or by creating and translating a polynucleotide in which the peptide regions are encoded in the desired relationship.

One of ordinary skill in the art will readily appreciate that designation of two amino acid sequences of the recombinant IFN-γ polypeptide disclosed herein as the "first" amino acid sequence and/or the "second" amino acid sequence is not intended to imply any particular structural arrangement of the "first" and "second" amino acid sequences within the chimeric IFN-γ polypeptide. By way of non-limiting example, in some embodiments, the amino acid sequences for the first monomer (e.g., chain A) and the second mononer (e.g., chain B) of a recombinant IFN-γ dimer of the disclosure may be swapped in order. For example, in some embodiments, a dimeric IFN-γ polypeptide of the disclosure may include, in the N-terminal to C-terminal direction: an amino acid sequence encoding the first monomer (e.g., chain A), a linker, and an amino acid sequence encoding the second mononer (e.g., chain B). In some other embodiments, a dimeric IFN-γ polypeptide of the disclosure may include, in the N-terminal to C-terminal direction: an amino acid sequence encoding the second monomer (e.g., chain B), a linker, and an amino acid sequence encoding the first mononer (e.g., chain A). In some other embodiments, a dimeric IFN-γ polypeptide disclosed herein may include (1) an N-terminal amino acid sequence comprising at least one amino acid substitution at the IFN-γR1 binding interface and (2) a C-terminal amino acid sequence comprising at least one amino acid substitution at the IFN-γR2 binding interface. In other embodiments, a dimeric IFN-γ polypeptide disclosed herein may include (1) an N-terminal amino acid sequence comprising at least one amino acid substitution at the IFN-γR2 binding interface and (1) a C-terminal portion amino acid sequence comprising at least one amino acid substitution at the IFN-γR1 binding interface. In addition, or alternatively, the recombinant IFN-γ polypeptide in accordance with some embodiments of the disclosure may include more than one amino acid sequence comprising amino acid substitutions at the IFN-γR1 binding interface, and/or more than one amino acid sequences comprising amino acid substitutions at the IFN-γR1 binding interface.

It is also contemplated that the first amino acid sequence and the second amino acid sequence of the recombinant IFN-γ polypeptide disclosed herein may include the same or different amino acid substitutions. Accordingly, in some embodiments of the disclosure, the first amino acid sequence and the second amino acid sequence of the recombinant polypeptide disclosed herein include the same number of amino acid substitutions. In some embodiments of the disclosure, the first amino acid sequence and the second amino acid sequence of the recombinant polypeptide disclosed herein include different numbers of amino acid substitutions. In some embodiments, the first amino acid sequence and the second amino acid sequence of the recombinant polypeptide disclosed herein include the same amino acid substitutions. In some embodiments, the first amino acid sequence and the second amino acid sequence of the recombinant polypeptide disclosed herein include different amino acid substitutions. In some embodiments, at least one of the first amino acid sequence and the second amino acid sequence of the recombinant polypeptide disclosed herein does not include any amino acid substitution compared to a naturally-occurring IFN-γ polypeptide.

In some embodiments, the recombinant polypeptide of the disclosure includes, in the N-terminal to C-terminal direction: (a) a first polypeptide segment including a first amino acid sequence with 100% sequence identity to SEQ ID NO: 1; (b) a cleavable peptide linker sequence; and (c) a second polypeptide segment including the amino acid sequence of SEQ ID NO: 1 with amino acid substitutions K74A, E75Y, and N83R (see, e.g., FIGS. 6A-6B). In some other embodiments, the recombinant polypeptide of the disclosure includes, in the N-terminal to C-terminal direction: (a) a first polypeptide segment including the amino acid sequence of SEQ ID NO: 1 with the amino acid substitution H111D; (b) a cleavable peptide linker sequence; and (c) a second polypeptide segment including the amino acid sequence of SEQ ID NO: 1 with the amino acid substitutions K74A, E75Y, and N83R (see, e.g., FIGS. 7A-7B). In yet other embodiments, the recombinant polypeptide of the disclosure includes, in the N-terminal to C-terminal direction, (a) a first polypeptide segment including the amino acid sequence of SEQ ID NO: 1 with the amino acid substitutions A23E, D24E, N25K, and H111D; (b) a cleavable peptide linker sequence; and (c) a second polypeptide segment including the amino acid sequence of SEQ ID NO: 1 with the amino acid substitutions K74A, E75Y, and N83R (see, e.g., FIGS. 9A-9B). As discussed above, one of ordinary skill in the art will readily appreciate that designation of two amino acid sequences of the recombinant IFN-γ polypeptide disclosed herein as the "first" amino acid sequence and/or the "second" amino acid sequence is not intended to imply any particular structural arrangement of the "first" and "second" amino acid sequences within the chimeric IFN-γ polypeptide. Thus, in some embodiments, the first polypeptide segment (e.g., chain A) and the second polypeptide segment (e.g., chain B) of a recombinant IFN-γ dimer of the disclosure may be swapped in order.

In some embodiments, the recombinant polypeptide of the disclosure includes an amino acid sequence that has at least 80% sequence identity to an amino acid sequence selected from the group consisting of SEQ ID NOS: 2, 3, 4, and 5. In some embodiments, the recombinant polypeptide includes an amino acid sequence that has at least 85%, at least 90%, at least 95%, at least 96%, at least 97%, at least 98%, at least 99%, or 100% sequence identity to an amino acid sequence selected from the group consisting of SEQ ID NOS: 2, 3, 4, and 5. In some embodiments, the recombinant polypeptide includes an amino acid sequence that has at least 80%, at least 85%, at least 90%, at least 95%, at least 96%, at least 97%, at least 98%, at least 99%, or 100% sequence identity to the amino acid sequence of SEQ ID NO: 2. In some embodiments, the recombinant polypeptide includes an amino acid sequence that has at least 80%, at least 85%, at least 90%, at least 95%, at least 96%, at least 97%, at least 98%, at least 99%, or 100% sequence identity to the amino acid sequence of SEQ ID NO: 3. In some embodiments, the recombinant polypeptide includes an amino acid sequence that has at least 80%, at least 85%, at least 90%, at least 95%, at least 96%, at least 97%, at least 98%, at least 99%, or 100% sequence identity to the amino acid sequence of SEQ ID NO: 4. In some embodiments, the recombinant polypeptide includes an amino acid sequence that has at least 80%, at least 85%, at least 90%, at least 95%, at least 96%, at least 97%, at least 98%, at least 99%, or 100% sequence identity to the amino acid sequence of SEQ ID NO: 5. In some embodiments, the recombinant polypeptide of the disclosure includes an amino acid sequence selected from the group consisting of SEQ ID NO: 2, SEQ ID NO: 3, SEQ ID NO: 4, and SEQ ID NO: 5.

In some embodiments of the recombinant polypeptide disclosed herein, at least one of the amino acid substitutions confers reduced binding affinity of the polypeptide to interferon-gamma receptor subunit 1 (IFN-γR1) and/or interferon-gamma receptor subunit 2 (IFN-γR2), compared to the respective binding affinity of a reference polypeptide lacking the at least one amino acid substitution. In some embodiments, the at least one amino acid substitution confers a substantial reduction in binding affinity of the polypeptide to interferon-gamma receptor subunit 2 (IFN-γR2) while substantially retains its binding affinity to interferon-gamma receptor subunit 1 (IFN-γR1), compared to the respective binding affinity of a reference polypeptide lacking the at least one amino acid substitution.

The binding activity of recombinant polypeptides of the disclosure, including the IFN-γ polypeptide variants as described herein, can be assayed by any suitable method known in the art. For example, the binding activity of an IFN-γ polypeptide variant disclosed herein and its receptors (e.g., IFN-γR1 and/or IFN-γR2) can be determined by Scatchard analysis (Munsen et al. Analyt. Biochem. 107: 220-239, 1980). Specific binding may also be assessed using techniques known in the art including but not limited to competition ELISA, Biacore® assays and/or KinExA® assays. A polypeptide that "preferentially binds" or "specifically binds" (used interchangeably herein) to a target protein is a term well understood in the art, and methods to determine such specific or preferential binding are also known in the art. A polypeptide is said to exhibit "specific binding" or "preferential binding" if it reacts or associates more frequently, more rapidly, with greater duration and/or with greater affinity with a particular target protein than it does with alternative proteins. In some embodiments, a polypeptide "specifically binds" or "preferentially binds" to a target if it binds with greater affinity, avidity, more readily, and/or with greater duration than it binds to other substances. In some embodiments, a polypeptide "specifically binds" or "preferentially binds" to a target if it binds with greater affinity, avidity, more readily, and/or with greater duration to that target in a sample than it binds to other substances present in the sample. For example, an IFN-γ polypeptide as described herein that specifically or preferentially binds to a receptor (e.g., IFN-γR1 or IFN-γR2) is an IFN-γ polypeptide that binds this receptor with greater affinity, avidity, more readily, and/or with greater duration than it binds to other IFN-γ receptors or non-IFN-γ receptors. It is also understood by reading this definition, for example, that a polypeptide which specifically or preferentially binds to a first target may or may not specifically or preferentially bind to a second target. As such, "specific binding" or "preferential binding" does not necessarily require (although it can include) exclusive binding.

A variety of assay formats may be used to select a recombinant polypeptide that binds a molecule of interest (e.g., IFN-γR1 or IFN-γR2). For example, solid-phase ELISA immunoassay, immunoprecipitation, Biacore™ (GE Healthcare, Piscataway, NJ), KinExA, fluorescence-activated cell sorting (FACS), Octet™ (ForteBio, Inc., Menlo Park, CA) and Western blot analysis are among many assays that may be used to identify a polypeptide that specifically reacts with a receptor or a ligand binding portion thereof, that specifically binds with a cognate ligand or binding partner. Generally, a specific or selective binding reaction will be at least twice the background signal or noise, more typically more than 10 times background, more than 20 times background, even more typically, more than 50 times background, more than 75 times background, more than 100 times background, yet more typically, more than 500 times background, even more typically, more than 1000 times background, and even more typically, more than 10,000 times background. In some embodiments, an IFN-γ polypeptide variant is said to "specifically bind" a ligand or receptor when the equilibrium dissociation constant ($K_D$) is <7 nM.

One of ordinary skill in the art will appreciate that "binding affinity" can also be used as a measure of the strength of a non-covalent interaction between two molecules, e.g., an IFN-γ polypeptide and an IFN-γ receptor. The term "binding affinity" is used to describe monovalent interactions (intrinsic activity). Binding affinity between two molecules may be quantified by determination of the dissociation constant ($K_D$). In turn, $K_D$ can be determined by measurement of the kinetics of complex formation and dissociation using, e.g., the surface plasmon resonance (SPR) method (Biacore). The rate constants corresponding to the association and the dissociation of a monovalent complex are referred to as the association rate constants $k_a$ (or $k_{on}$) and dissociation rate constant $k_d$ (or $k_{off}$), respectively. $K_D$ is related to $k_a$ and $k_d$ through the equation $K_D=k_d/k_a$. The value of the dissociation constant can be determined directly by well-known methods and can be computed even for complex mixtures by methods such as those set forth in Caceci et al. (Byte 9: 340-362, 1984). For example, the $K_D$ may be established using a double-filter nitrocellulose filter binding assay such as that disclosed by Wong & Lohman (1993, Proc. Natl. Acad. Sci. USA 90: 5428-5432). Other standard assays to evaluate the binding ability of the IFN-γ polypeptides variants of the present disclosure towards target receptors are known in the art, including for example, ELISAs, Western blots, RIAs, and flow cytometry analysis, and other assays exemplified in the Examples. The binding kinetics and binding affinity of the IFN-γ polypeptides variants also can be assessed by standard assays known in the art, such as Surface Plasmon Resonance (SPR), e.g. by using a Biacore™ system, or KinExA. In some embodiments, the binding affinity of the IFN-γ polypeptide variant of the disclosure to IFN-γR2 and/or IFN-γR1 is determined by a solid-phase receptor binding assay (Matrosovich M N et al., Methods Mol Biol. 865:71-94, 2012). In some embodiments, the binding affinity of the IFN-γ polypeptide variant of the disclosure to IFN-γR2 and/or IFN-γR1 is determined by a Surface Plasmon Resonance (SPR) assay.

In some embodiments, the ratio of IFN-γR2 binding affinity to IFN-γR1 binding affinity of the IFN-γ polypeptide variant of the disclosure is about 1:500 to about 1:2. In some embodiments, the ratio of IFN-γR2 binding affinity to IFN-γR1 binding affinity of the polypeptide is about 1:500 to about 1:200, about 1:400 to about 1:100, about 1:300 to about 1:50, about 1:200 to about 1:20, about 1:100 to about 1:2, or about 1:50 to about 1:2. In some embodiments, the ratio of IFN-γR2 binding affinity to IFN-γR1 binding affinity of the polypeptide is about 1:500, about 1:400, about 1:300, about 1:200, about 1:100, about 1:50, about 1:20, about 1:10, about 1:5, about 1:200, or about 1:2. In some embodiments, the ratio of IFN-γR2 binding affinity to IFN-γR1 binding affinity of the polypeptide is about 1:500 to about 1:2, as determined by a solid-phase receptor binding assay.

In some embodiments, the IFN-γ polypeptide variants of the disclosure, e.g., IFN-γ partial agonists, significantly reduce levels of PD-L1 upregulation in cells treated with such IFN-γ partial agonists, while retaining significant capacity to upregulate MHC class I expression, as determined by an MHC I: PD-L1 expression ratio relative to a reference ratio observed in control cells treated with wild-type IFN-γ. In some embodiments, the MHC I: PD-L1 expression ratio in cells treated with an IFN-γ partial agonist disclosed herein relative to a reference ratio observed in control cells treated wild-type IFN-γ is about 2:1 to about 100:1. In some embodiments, the MHC I: PD-L1 expression ratio in cells treated with an IFN-γ partial agonist of the present disclosure relative to a reference ratio observed in control cells treated with wild-type IFN-γ is about 2:1 to about 50:1, about 5:1 to about 40:1, about 10:1 to about 30:1, about 20:1 to about 50:1, about 5:1 to about 40:1, about 15:1 to about 30:1, or about 10:1 to about 20:1. In some embodiments, the MHC I: PD-L1 expression ratio in cells treated with an IFN-γ partial agonist as disclosed herein relative to a reference ratio observed in control cells treated with wild-type IFN-γ is about 2:1 to about 50:1, about 5:1 to about 20:1, about 10:1 to about 40:1, about 20:1 to about 30:1, about 5:1 to about 10:1, about 2:1 to about 5:1, or about 40:1 to about 50:1, as determined by a suitable expression assay such as a nucleic acid-based expression assay or an antibody-based expression assay.

As discussed above, the IFN-γ induced side effects are generally believed to be caused, at least in part, by IFN-γ's pleiotropic activity pattern. That is because IFN-γ acts on most cell types in the body evoking a complex toxicity pattern when administered systemically. Similar systemic toxicity also prevents application of many other immune-modulating cytokines such as interleukin-1 (IL-1), IL-2, and tumor necrosis factor (TNF). Hence, without being bound to any particular theory, it is also contemplated that the recombinant polypeptides as disclosed herein can also be targeted to specific cell types, tissues, or in the vicinity thereof, in order to further circumvent potential toxicity problem caused by the systemic administration of a recombinant polypeptide of the disclosure to a subject in need thereof. Many strategies can be pursued to obtain targeted delivery of the polypeptides of the disclosure to a particular cell type, tissue, on in the vicinity thereof. Generally, the delivery of a polypeptide disclosed herein to a target cell types, tissues, or in the vicinity thereof, can be effectively achieved by any one of several methodologies and strategies known in the art such as, for example, direct injection at the tumor site via, for example, a three-dimensional guidance systems. Another example of suitable strategy for effective targeted delivery of the polypeptides of the disclosure is via the use of vectors such as viral vectors or tumor infiltrating immune cells.

In another strategy of targeted delivery, the polypeptides of the disclosure can be operably linked to one or more targeting moieties (e.g., nucleic acids, ligands, haptens, antibodies, and aptamers). Optionally, the disclosed polypeptide can be attached to at least one targeting moieties via a linker such as, e.g., a biodegradable linker. For example, antibody IFN-γ fusion proteins of the disclosed polypeptide can be used to guide the disclosed IFN-γ polypeptide variant specifically to a tumor site. Accordingly, in some embodiments, the disclosed IFN-γ polypeptide variant can be fused to one or more tumor targeting moieties. In some particular embodiments, the polypeptide of the disclosure is operably linked to one or more monoclonal antibodies or antibody fragments targeting an oncogenic receptor, a marker, or a component of the extracellular matrix associated with tumor cells. In some other particular embodiments, the polypeptide of the disclosure is operably linked to one or more ligands of an oncogenic receptor or a receptor expressed by tumor cells. Further information in this regard can be found, for example, in a recent review by Uze and Tavernier (*Cytokine & Growth Factor Reviews* 26 (2015) 179-182), which is incorporated herein by reference.

It will be also appreciated by one of ordinary skill in the art upon reading this disclosure that any one of the IFN-γ partial agonists as disclosed herein can be targeted to different subsets of immune cells, whereby exerts its biased action towards the targeted immune cell subsets. Generally, the IFN-γ partial agonists of the disclosure can be targeted to any known immune cell types, tissues, organs, or in the vicinity thereof. Non-limiting examples of immune cell types suitable for the targeting of the IFN-γ partial agonists disclosed herein include B cells, T cells, NK cells, monocytes, macrophages, and combinations of any thereof. Suitable B cells and T cells include, but are not limited to, activated CD4, naïve CD4, activated CD48, naïve CD8, and peripheral B cells. Non-limiting examples of NK cells suitable for the targeting of the IFN-γ partial agonists disclosed herein include CD3 NK cells, CD16+NK cells, CD56+NK cells. In addition, or alternatively, monocytes expressing one or more of the following markers CD14, CD16, and CD56 are non-limiting examples of monocytes suitable for the targeting of the IFN-γ partial agonists disclosed herein.

Without being bound by theory, the conjugation of the polypeptides of the present disclosure to an antibody facilitates the targeted delivery of the compound to the site of intended action such as a cancer cell, tumor, or in the vicinity thereof, and reduces the risk of systemic toxicity.

One skilled in the art will appreciate that the complete amino acid sequence of any one of the recombinant polypeptides as disclosed herein can be used to construct a back-translated gene. For example, a DNA oligomer containing a nucleotide sequence coding for a given polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the DNA sequences encoding a recombinant polypeptide as disclosed herein will be inserted into an expression vector and operably linked to an expression control sequence appropriate for expression of the recombinant polypeptide in the desired transformed host. Proper assembly can be confirmed by nucleotide sequencing, restriction mapping, and expression of a biologically active polypeptide in a suitable host. As is known in the art, in order to obtain high expression levels of a transfected gene in a host, the gene must be operably linked to transcriptional and translational expression control sequences that are functional in the chosen expression host.

In addition or alternatively, the generation of any one of the recombinant polypeptides described herein can be achieved via expression of nucleic acid molecules that have been altered by recombinant molecular biological techniques. Furthermore, the recombinant polypeptides in accordance with the present disclosure can be chemically synthesized. Chemically synthesized polypeptides are routinely generated by those of skill in the art.

Nucleic Acid Molecules

In one aspect, some embodiments disclosed herein relate to recombinant nucleic acid molecules encoding the recombinant polypeptides of the disclosure, including the IFN-γ polypeptide variants as described herein, expression cassettes, and expression vectors containing these nucleic acid molecules operably linked to heterologous nucleic acid sequences such as, for example, regulator sequences which allow expression of the IFN-γ polypeptide variants in a host cell or ex-vivo cell-free expression system.

The terms "nucleic acid molecule" and "polynucleotide" are used interchangeably herein, and refer to both RNA and DNA molecules, including nucleic acid molecules comprising cDNA, genomic DNA, synthetic DNA, and DNA or RNA molecules containing nucleic acid analogs. A nucleic acid molecule can be double-stranded or single-stranded (e.g., a sense strand or an antisense strand). A nucleic acid molecule may contain unconventional or modified nucleotides. The terms "polynucleotide sequence" and "nucleic acid sequence" as used herein interchangeably refer to the sequence of a polynucleotide molecule. The polynucleotide and polypeptide sequences disclosed herein are shown using standard letter abbreviations for nucleotide bases and amino acids as set forth in 37 CFR § 1.82), which incorporates by reference WIPO Standard ST.25 (1998), Appendix 2, Tables 1-6.

Nucleic acid molecules of the present disclosure can be nucleic acid molecules of any length, including nucleic acid molecules that are generally between about 5 Kb and about 50 Kb, for example between about 5 Kb and about 40 Kb, between about 5 Kb and about 30 Kb, between about 5 Kb and about 20 Kb, or between about 10 Kb and about 50 Kb, for example between about 15 Kb to 30 Kb, between about 20 Kb and about 50 Kb, between about 20 Kb and about 40 Kb, about 5 Kb and about 25 Kb, or about 30 Kb and about 50 Kb.

In some embodiments disclosed herein, the nucleic acid molecules of the disclosure include a nucleotide sequence encoding a polypeptide which includes an amino acid sequence having at least 90%, 95%, 96%, 97, 98%, 99% sequence identity to the amino acid sequence of a recombinant polypeptide as disclosed herein. In some embodiments, the nucleic acid molecules of the disclosure include a nucleotide sequence encoding a polypeptide which includes a first amino acid sequence having at least 95% identity to an IFN-γ polypeptide having the amino acid sequence of SEQ ID NO: 1; and further including at least one amino acid substitution at a position corresponding to an amino acid residue selected from the group consisting of Q1, D2, P3, K6, Q64, Q67, K68, E71, T72, K74, E75, D76, N78, V79, K80, N83, S84, K86, R89, and D90 of SEQ ID NO: 1, and any combination thereof. In some embodiments, the nucleic acid molecules of the disclosure further include a second amino acid sequence having at least 95% identity to a gamma-interferon polypeptide having the amino acid sequence of SEQ ID NO: 1, wherein the second amino acid sequence is operably linked to the first amino acid sequence. In some embodiments, the second amino acid sequence includes at least one amino acid substitution at a position corresponding to an amino acid residue selected from the group consisting of Q1, D2, P3, K6, Q64, Q67, K68, E71, T72, K74, E75, D76, N78, V79, K80, N83, S84, K86, R89, and D90 of SEQ ID NO: 1, and any combination thereof.

In some embodiments disclosed herein, the nucleic acid molecules of the disclosure include a nucleotide sequence encoding a polypeptide which includes an amino acid sequence having at least 90%, 95%, 96%, 97, 98%, 99% sequence identity to an amino acid sequence selected from the group consisting of SEQ ID NOS: 2, 3, 4, and 5. In some embodiments, the nucleic acid molecules of the disclosure include a nucleotide sequence encoding a polypeptide which includes an amino acid sequence having at least 90%, 95%, 96%, 97, 98%, 99%, or 100% sequence identity to the amino acid sequence of SEQ ID NO: 2. In some embodiments, the nucleic acid molecules of the disclosure include a nucleotide sequence encoding a polypeptide which includes an amino acid sequence having at least 90%, 95%, 96%, 97, 98%, 99%, or 100% sequence identity to the amino acid sequence of SEQ ID NO: 3. In some embodiments, the nucleic acid molecules of the disclosure include a nucleotide sequence encoding a polypeptide which includes an amino acid sequence having 90%, 95%, 96%, 97, 98%, 99%, or 100% sequence identity to the amino acid sequence of SEQ ID NO: 4. In some embodiments, the nucleic acid molecules of the disclosure include a nucleotide sequence encoding a polypeptide which includes an amino acid sequence having 90%, 95%, 96%, 97, 98%, 99%, or 100% sequence identity to the amino acid sequence of SEQ ID NO: 5. In some embodiments, the nucleic acid molecules of the disclosure include a nucleotide sequence encoding a polypeptide which includes an amino acid sequence selected from the group consisting of SEQ ID NO: 2, SEQ ID NO: 3, SEQ ID NO: 4, and SEQ ID NO: 5.

Some embodiments disclosed herein relate to vectors or expression cassettes including a recombinant nucleic acid molecule as disclosed herein. As used herein, the term "expression cassette" refers to a construct of genetic material that contains coding sequences and enough regulatory information to direct proper transcription and/or translation of the coding sequences in a recipient cell, in vivo and/or ex vivo. The expression cassette may be inserted into a vector for targeting to a desired host cell and/or into a subject. As such, the term expression cassette may be used interchangeably with the term "expression construct". As used herein, the term "construct" is intended to mean any recombinant nucleic acid molecule such as an expression cassette, plasmid, cosmid, virus, autonomously replicating polynucleotide molecule, phage, or linear or circular, single-stranded or double-stranded, DNA or RNA polynucleotide molecule, derived from any source, capable of genomic integration or autonomous replication, comprising a nucleic acid molecule where one or more nucleic acid sequences has been linked in a functionally operative manner, e.g. operably linked.

Also provided herein are vectors, plasmids or viruses containing one or more of the nucleic acid molecules encoding any of the recombinant polypeptides disclosed herein. The nucleic acid molecules described above can be contained within a vector that is capable of directing their expression in, for example, a cell that has been transformed/transduced with the vector. Suitable vectors for use in eukaryotic and prokaryotic cells are known in the art and are commercially available or readily prepared by a skilled artisan. Additional vectors can also be found, for example, in *Current Protocols in Molecular Biology* (Ausubel F M et al., eds., 1987, including supplements through 2014) and *Molecular Cloning: A Laboratory Manual*, fourth edition (Sambrook et al., 2012).

It should be understood that not all vectors and expression control sequences will function equally well to express the DNA sequences described herein. Neither will all hosts function equally well with the same expression system. However, one of skill in the art may make a selection among these vectors, expression control sequences and hosts to achieve desired expression levels of the polypeptides of the present disclosure without undue experimentation. For example, when selecting a vector, the host cell is considered because the vector is required to replicate in such host cell. The vector's copy number, the ability to control that copy number, and the expression of any other proteins encoded by the vector, such as antibiotic markers, should also be considered. For example, vectors that can be used include those that allow the DNA encoding the recombinant polypeptides of the present disclosure to be amplified in copy number. Such amplifiable vectors are known in the art.

Accordingly, in some embodiments, the recombinant polypeptides of the disclosure, including the IFN-γ polypeptide variants as described herein, can be expressed from vectors, e.g., expression vectors. The vectors are useful for autonomous replication in a host cell or may be integrated into the genome of a host cell upon introduction into the host cell, and thereby are replicated along with the host genome (e.g., non-episomal mammalian vectors). Generally, the expression vector comprises expression control elements operably linked to the coding sequences to facilitate expression in the host cell. In general, expression vectors of utility in recombinant DNA techniques are often in the form of plasmids (vectors). However, other forms of expression vectors, such as viral vectors (e.g., e.g., replication-competent or replication-deficient retroviruses, adenoviruses, and adeno-associated viruses) are also included. Exemplary recombinant expression vectors can include one or more regulatory sequences, selected on the basis of the host cells to be used for expression, operably linked to the nucleic acid sequence to be expressed. In some embodiments, the vector is a lentiviral vector, an adeno virus vector, an adeno-associated virus vector, or a retroviral vector.

DNA vector can be introduced into prokaryotic or eukaryotic cells via conventional transformation or transfection techniques. Suitable methods for transforming or transfecting host cells can be found in Sambrook et al. (2012, supra) and other standard molecular biology laboratory manuals.

The nucleic acid sequences encoding the recombinant polypeptides of the disclosure, including the IFN-γ polypeptide variants as described herein, can be optimized for expression in the host cell of interest. For example, the G-C content of the sequence can be adjusted to levels average for a given cellular host, as calculated by reference to known genes expressed in the host cell. Methods for codon optimization are known in the art. Codon usages within the coding sequence of the recombinant polypeptides disclosed herein can be optimized to enhance expression in the host cell, such that about 1%, about 5%, about 10%, about 25%, about 50%, about 75%, or up to 100% of the codons within the coding sequence have been optimized for expression in a particular host cell.

Vectors suitable for use include T7-based vectors for use in bacteria, the pMSXND expression vector for use in mammalian cells, and baculovirus-derived vectors for use in insect cells. In some embodiments, nucleic acid inserts, which encode the subject recombinant polypeptide in such vectors, can be operably linked to a promoter, which is selected based on, for example, the cell type in which expression is sought.

In selecting an expression control sequence, a variety of factors should also be considered. These include, for example, the relative strength of the sequence, its controllability, and its compatibility with the actual DNA sequence encoding the subject polypeptide, particularly as regards potential secondary structures. Hosts should be selected by consideration of their compatibility with the chosen vector, the toxicity of the product coded for by the DNA sequences of this disclosure, their secretion characteristics, their ability to fold the polypeptides correctly, their fermentation or culture requirements, and the ease of purification of the products coded for by the DNA sequences.

Within these parameters one of skill in the art may select various vector/expression control sequence/host combinations that will express the desired DNA sequences in fermentation or in large scale animal cell culture, for example, using CHO cells or COS-7 cells.

The choice of expression control sequence and expression vector, in some embodiments, will depend upon the choice of host. A wide variety of expression host/vector combinations can be employed. Non-limiting examples of useful expression vectors for eukaryotic hosts, include, for example, vectors with expression control sequences from SV40, bovine papilloma virus, adenovirus and cytomegalovirus. Non-limiting examples of useful expression vectors for bacterial hosts include known bacterial plasmids, such as plasmids from E. coli, including col El, pCRI, pER32z, pMB9 and their derivatives, wider host range plasmids, such as RP4, phage DNAs, e.g., the numerous derivatives of phage lambda, e.g., NM989, and other DNA phages, such as M13 and filamentous single stranded DNA phages. Non-limiting examples of useful expression vectors for yeast cells include the 2p plasmid and derivatives thereof. Non-limiting examples of useful vectors for insect cells include pVL 941 and pFastBac™ 1.

In addition, any of a wide variety of expression control sequences can be used in these vectors. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the major operator and promoter regions of phage lambda, for example PL, the control regions of fd coat protein, the promoter for 3-phosphoglycerate kinase or other glycolytic enzymes, the promoters of acid phosphatase, e.g., PhoA, the promoters of the yeast a-mating system, the polyhedron promoter of Baculovirus, and other sequences known to control the expression of genes of prokaryotic or eukaryotic cells or their viruses, and various combinations thereof.

A T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans will readily appreciate numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance (neoR) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that can be used in the disclosure include, for example, retroviral, adenoviral, and adeno-associated vectors, herpes virus, simian virus 40 (SV40), and bovine papilloma virus vectors (see, for example, Gluzman (Ed.), Eukaryotic Viral Vectors, 1982, CSH Laboratory Press, Cold Spring Harbor, N.Y.).

Prokaryotic or eukaryotic cells that contain and express a nucleic acid molecule that encodes a subject recombinant polypeptide disclosed herein are also features of the disclosure. A cell of the disclosure is a transfected cell, e.g, a cell into which a nucleic acid molecule, for example a nucleic acid molecule encoding an IFN-γ polypeptide variant, has been introduced by means of recombinant DNA techniques. The progeny of such a cell are also considered within the scope of the disclosure.

The precise components of the expression system are potentially widely variable. For example, an IFN-γ polypeptide variant as disclosed herein can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, the components of the expression system should be compatible with one another. Artisans or ordinary skill are able to make such a determination. Furthermore, if guidance is required in selecting an expression system, skilled artisans may consult Ausubel et al. (*Current Protocols in Molecular Biology*, John Wiley and Sons, New York, N.Y., 1993) and Pouwels et al. (*Cloning Vectors: A Laboratory Manual*, 1985 Suppl. 1987).

The expressed polypeptides can be isolated from the expression system using routine biochemical procedures, and can be used, e.g., as therapeutic agents, as described herein.

In some embodiments, recombinant polypeptides obtained will be glycosylated or unglycosylated depending on the host organism used to produce the recombinant polypeptides. If bacteria are chosen as the host then the recombinant polypeptide produced will be unglycosylated. Eukaryotic cells, on the other hand, will typically glycosylate the recombinant polypeptides, although perhaps not in the same way as native polypeptides is glycosylated. The recombinant polypeptides produced by the transformed host can be purified according to any suitable methods known in the art. Produced recombinant polypeptides can be isolated from inclusion bodies generated in bacteria such as *E. coli*, or from conditioned medium from either mammalian or yeast cultures producing a given recombinant polypeptide of the disclosure using cation exchange, gel filtration, and or reverse phase liquid chromatography.

In addition, or alternatively, another exemplary method of constructing a DNA sequence encoding the recombinant polypeptides of the disclosure is by chemical synthesis. This includes direct synthesis of a peptide by chemical means of the amino acid sequence encoding for a recombinant polypeptide exhibiting the properties described. This method can incorporate both natural and unnatural amino acids at positions that affect the binding affinity of the recombinant polypeptides with a target protein. Alternatively, a gene which encodes the desired recombinant polypeptides can be synthesized by chemical means using an oligonucleotide synthesizer. Such oligonucleotides are designed based on the amino acid sequence of the desired recombinant polypeptides, and preferably selecting those codons that are favored in the host cell in which the recombinant polypeptide of the disclosure will be produced. In this regard, it is well recognized in the art that the genetic code is degenerate, that an amino acid may be coded for by more than one codon. For example, Phe (F) is coded for by two codons, TIC or TTT, Tyr (Y) is coded for by TAC or TAT and his (H) is coded for by CAC or CAT. Trp (W) is coded for by a single codon, TGG. Accordingly, it will be appreciated by those skilled in the art that for a given DNA sequence encoding a particular recombinant polypeptide, there will be many DNA degenerate sequences that will code for that recombinant polypeptide. For example, it will be appreciated that in addition to the DNA sequences for recombinant polypeptides provided in the Sequence Listing, there will be many degenerate DNA sequences that code for the recombinant polypeptides disclosed herein. These degenerate DNA sequences are considered within the scope of this disclosure. Therefore, "degenerate variants thereof" in the context of this disclosure means all DNA sequences that code for and thereby enable expression of a particular recombinant polypeptide.

The DNA sequence encoding the subject recombinant polypeptide, whether prepared by site directed mutagenesis, chemical synthesis or other methods, can also include DNA sequences that encode a signal sequence. Such signal sequence, if present, should be one recognized by the cell chosen for expression of the recombinant polypeptide. It can be prokaryotic, eukaryotic or a combination of the two. In general, the inclusion of a signal sequence depends on whether it is desired to secrete the recombinant polypeptide as disclosed herein from the recombinant cells in which it is made. If the chosen cells are prokaryotic, the DNA sequence generally does not encode a signal sequence. If the chosen cells are eukaryotic, a signal sequence is frequently included.

The nucleic acid molecules provided can contain naturally occurring sequences, or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (e.g, either a sense or an antisense strand).

The nucleic acid molecules are not limited to sequences that encode polypeptides; some or all of the non-coding sequences that lie upstream or downstream from a coding sequence (e.g., the coding sequence of an IFN-γ polypeptide variant) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

Exemplary isolated nucleic acid molecules of the present disclosure can include fragments not found as such in the natural state. Thus, this disclosure encompasses recombinant molecules, such as those in which a nucleic acid sequence (for example, a sequence encoding an IFN-γ polypeptide variant) is incorporated into a vector (e.g., a plasmid or viral vector) or into the genome of a heterologous cell (or the genome of a homologous cell, at a position other than the natural chromosomal location).

The terms, "cell"," "cell culture"," "cell line"," "recombinant host cell"," "recipient cell" and "host cell" as used herein, include the primary subject cells and any progeny thereof, without regard to the number of transfers. It should be understood that not all progeny are exactly identical to the parental cell (due to deliberate or inadvertent mutations or differences in environment); however, such altered progeny are included in these terms, so long as the progeny retain the same functionality as that of the originally transformed cell.

Pharmaceutical Compositions

In some embodiments, the recombinant polypeptides of the disclosure, including the IFN-γ polypeptide variants, and nucleic acids as described herein, can be incorporated into compositions, including pharmaceutical compositions. Such compositions typically include the recombinant polypeptides and a pharmaceutically acceptable excipient, e.g., carrier.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™. (BASF, Parsippany, N.J.), or phosphate buffered saline (PBS). In all cases, the composition should be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. Prevention of the action of microorganisms can be achieved by various antibacterial and antifungal agents, for example, parabens, chlorobutanol, phenol, ascorbic acid, thimerosal, and the like. In many cases, it will be generally to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions, if used, generally include an inert diluent or an edible carrier. For the purpose of oral therapeutic administration, the active compound (e.g., recombinant polypeptides, IFN-γ polypeptide variants, IFN-γ partial agonists, and/or nucleic acid molecules of the disclosure) can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches, and the like, can contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate or Sterotes™; a glidant such as colloidal silicon dioxide; a sweetening agent such as sucrose or saccharin; or a flavoring agent such as peppermint, methyl salicylate, or orange flavoring.

In the event of administration by inhalation, the subject recombinant polypeptides of the disclosure are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration of the subject recombinant polypeptides of the disclosure can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In some embodiments, the recombinant polypeptides of the disclosure can also be prepared in the form of suppositories (e.g., with conventional suppository bases such as cocoa butter and other glycerides) or retention enemas for rectal delivery.

In some embodiments, the recombinant polypeptides of the disclosure can also be administered by transfection or infection using methods known in the art, including but not limited to the methods described in McCaffrey et al. (Nature 418:6893, 2002), Xia et al. (Nature Biotechnol. 20: 1006-1010, 2002), or Putnam (Am. J. Health Syst. Pharm. 53: 151-160, 1996, erratum at Am. J. Health Syst. Pharm. 53:325, 1996).

In some embodiments, the subject recombinant polypeptides of the disclosure are prepared with carriers that will protect the recombinant polypeptides against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811. As described in greater detail below, the recombinant polypeptides of the present disclosure may also be modified to achieve extended duration of action such as by PEGylation, acylation, Fc fusions, linkage to molecules such as albumin, etc. In some embodiments, the recombinant polypeptides can be further modified to prolong their half-life in vivo and/or ex vivo. Non-limiting examples of known strategies and methodologies suitable for modifying the recombinant polypeptides of the disclosure include (1) chemical modification of a recombinant polypeptide described herein with highly soluble macromolecules such as polyethylene glycol ("PEG") which prevents the recombinant polypeptides from contacting with proteases; and (2) covalently linking or conjugating a recombinant polypeptide described herein with a stable protein such as, for example, albumin. Accordingly, in some embodiments, the recombinant polypeptides of the disclosure can be fused to a stable protein, such as, albumin. For example, human albumin is known as one of the most effective proteins for enhancing the stability of polypeptides fused thereto and there are many such fusion proteins reported.

In some embodiments, the pharmaceutical compositions of the disclosure include one or more pegylation reagents. As used herein, the term "PEGylation" refers to modifying a protein by covalently attaching polyethylene glycol (PEG) to the protein, with "PEGylated" referring to a protein having a PEG attached. A range of PEG, or PEG derivative sizes with optional ranges of from about 10,000 Daltons to about 40,000 Daltons may be attached to the recombinant polypeptides of the disclosure using a variety of chemistries. In some embodiments, the average molecular weight of said PEG, or PEG derivative, is about 1 kD to about 200 kD such as, e.g., about 10 kD to about 150 kD, about 50 kD to about 100 kD, about 5 kD to about 100 kD, about 20 kD to about 80 kD, about 30 kD to about 70 kD, about 40 kD to about 60 kD, about 50 kD to about 100 kD, about 100 kD to about 200 kD, or about 1 150 kD to about 200 kD. In some embodiments, the average molecular weight of said PEG, or PEG derivative, is about 5 kD, about 10 kD, about 20 kD, about 30 kD, about 40 kD, about 50 kD, about 60 kD, about 70 kD, or about 80 kD. In some embodiments, the average molecular weight of said PEG, or PEG derivative, is about 40 kD. In some embodiments, the pegylation reagent is selected from methoxy polyethylene glycol-succinimidyl propionate (mPEG-SPA), mPEG-succinimidyl butyrate (mPEG-SBA), mPEG-succinimidyl succinate (mPEG-SS), mPEG-succinimidyl carbonate (mPEG-SC), mPEG-Succinimidyl Glutarate (mPEG-SG), mPEG-N-hydroxyl-succinimide (mPEG-NHS), mPEG-tresylate and mPEG-aldehyde. In some embodiments, the pegylation reagent is polyethylene glycol; for example said pegylation reagent is polyethylene glycol with an average molecular weight of 20,000 Daltons covalently bound to the N-terminal methionine residue of the recombinant polypeptides of the disclosure. In some embodiments, the pegylation reagent is polyethylene glycol with an average molecular weight of about 5 kD, about 10 kD, about 20 kD, about 30 kD, about 40 kD, about 50 kD, about 60 kD, about 70 kD, or about 80 kD covalently bound to the N-terminal methionine residue of the recombinant polypeptides of the disclosure. In some embodiments, the pegylation reagent is polyethylene glycol with an average molecular weight of about 40 kD covalently bound to the N-terminal methionine residue of the recombinant polypeptides of the disclosure.

Accordingly, in some embodiments, the recombinant polypeptides of the disclosure are chemically modified with one or more polyethylene glycol moieties, e.g., PEGylated; or with similar modifications, e.g. PASylated. In some embodiments, the PEG molecule or PAS molecule is conjugated to one or more amino acid side chains of the disclosed recombinant polypeptide. In some embodiments, the PEGylated or PASylated polypeptide contains a PEG or PAS moiety on only one amino acid. In other embodiments, the PEGylated or PASylated polypeptide contains a PEG or PAS moiety on two or more amino acids, e.g., attached to two or more, five or more, ten or more, fifteen or more, or twenty or more different amino acid residues. In some embodiments, the PEG or PAS chain is 2000, greater than 2000, 5000, greater than 5,000, 10,000, greater than 10,000, greater than 10,000, 20,000, greater than 20,000, and 30,000 Da. The PASylated polypeptide may be coupled directly to PEG or PAS (e.g., without a linking group) through an amino group, a sulfhydryl group, a hydroxyl group, or a carboxyl group. In some embodiments, the recombinant polypeptide of the disclosure is covalently bound to a polyethylene glycol with an average molecular weight of 20,000 Daltons. In some embodiments, the recombinant polypeptide of the disclosure is covalently bound to a polyethylene glycol with an average molecular weight ranging from about 1 kD to about 200 kD such as, e.g., about 10 kD to about 150 kD, about 50 kD to about 100 kD, about 5 kD to about 100 kD, about 20 kD to about 80 kD, about 30 kD to about 70 kD, about 40 kD to about 60 kD, about 50 kD to about 100 kD, about 100 kD to about 200 kD, or about 1 150 kD to about 200 kD. In some embodiments, the recombinant polypeptide of the disclosure is covalently bound to a polyethylene glycol with an average molecular weight of about 5 kD, about 10 kD, about 20 kD, about 30 kD, about 40 kD, about 50 kD, about 60 kD, about 70 kD, or about 80 kD. In some embodiments, the recombinant polypeptide of the disclosure is covalently bound to a polyethylene glycol with an average molecular weight of about 40 kD.

Methods of Treatment

Administration of any one of the therapeutic compositions described herein, e.g., recombinant polypeptides, IFN-γ polypeptide variants, IFN-γ partial agonists, nucleic acids, and pharmaceutical compositions, can be used to treat patients in the treatment of relevant diseases, such as cancers and chronic infections. In some embodiments, the recombinant polypeptides, IFN-γ polypeptide variants, IFN-γ partial agonists, nucleic acids, and/or pharmaceutical compositions as described herein can be incorporated into therapeutic agents for use in methods of treating an individual who has, who is suspected of having, or who may be at high risk for developing one or more autoimmune disorders or health diseases associated with checkpoint inhibition. Exemplary autoimmune disorders and health diseases can include, without limitation, cancers and chronic infection.

Accordingly, in one aspect, some embodiments of the disclosure relate to methods for modulating IFN-γ-mediated signaling in a subject, the method including administering to the subject an effective amount of a polypeptide as disclosed herein, or a nucleic acid molecule as disclosed herein. In another aspect, some embodiments relate to methods for the treatment of a health disease in a subject in need thereof, the method including administering to the subject an effective amount of a polypeptide as disclosed herein, or a nucleic acid molecule as disclosed herein.

In some embodiments, the disclosed pharmaceutical composition is formulated to be compatible with its intended route of administration. The recombinant polypeptides of the disclosure may be given orally or by inhalation, but it is more likely that they will be administered through a parenteral route. Examples of parenteral routes of administration include, for example, intravenous, intradermal, subcutaneous, transdermal (topical), transmucosal, and rectal administration. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates and agents for the adjustment of tonicity such as sodium chloride or dextrose. pH can be adjusted with acids or bases, such as mono- and/or di-basic sodium phosphate, hydrochloric acid or sodium hydroxide (e.g., to a pH of about 7.2-7.8, e.g., 7.5). The parenteral preparation can be enclosed in ampoules, disposable syringes or multiple dose vials made of glass or plastic.

Dosage, toxicity and therapeutic efficacy of such subject recombinant polypeptides of the disclosure can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are generally suitable. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the disclosure, the therapeutically effective dose can be estimated initially from cell culture assays. A dose may be formulated in animal models to achieve a circulating plasma concentration range that includes the $IC_{50}$ (e.g., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a "therapeutically effective amount" of a subject recombinant polypeptide of the disclosure (e.g, an effective dosage) depends on the polypeptide selected. For instance, single dose amounts in the range of approximately 0.001 to 0.1 mg/kg of patient body weight can be administered; in some embodiments, about 0.005, 0.01, 0.05 mg/kg may be administered. In some embodiments, 600,000 IU/kg is administered (IU can be determined by a lymphocyte proliferation bioassay and is expressed in International Units (IU) as established by the World Health Organization 1st International Standard for Interleukin-2 (human)). The dosage may be similar to, but is expected to be less than, that prescribed for PROLEUKIN®. The compositions can be administered one from one or more times per day to one or more times per week; including once every other day. The skilled artisan will appreciate that certain factors may influence the dosage and timing required to effectively treat a subject, including but not limited to the severity of the disease, previous treatments, the general health and/or age of the subject, and other diseases present. Moreover, treatment of a subject with a therapeutically effective amount of the subject recombinant polypeptides of the disclosure can include a single treatment or, can include a series of treatments. In some embodiments, the compositions are administered every 8 hours for five days, followed by a rest period of 2 to 14 days, e.g., 9 days, followed by an additional five days of administration every 8 hours.

In one aspect, provided herein is a method for modulating IFN-γ-mediated signaling in a subject, the method including administering to the subject an effective amount of a polypeptide as disclosed herein, or a nucleic acid molecule as disclosed herein.

In another aspect, provided herein is a method for the treatment of a health disease in a subject in need thereof, the method including administering to the subject an effective amount of a polypeptide as disclosed herein, or a nucleic acid molecule as disclosed herein.

In some embodiments, the administered recombinant polypeptide substantially confers bias in cell surface expression of one or more of receptors. Accordingly, in some embodiments, administration of an IFN-γ polypeptide variant as disclosed herein to a subject may confer bias in cell surface expression of one or more receptors such as, PD-L1, MHC Class I molecules, MHC Class II (HLA-DR), CD40, CD69, CD80, CD107a, and CD86. In some embodiments, the administered polypeptide substantially confers bias in cell surface expression of one or more of PD-L1, MHC Class I molecules, MHC Class II, CD80, CD86, and combinations of any thereof. In some embodiments, the administered polypeptide substantially confers bias in cell surface expression of one or more of PD-L1 and MHC Class I molecules.

In some embodiments, the administered recombinant polypeptide has reduced capacity to upregulate expression of PD-L1 in the subject, as compared to a reference polypeptide lacking the at least one amino acid substitution such as, e.g., a wild-type IFN-γ polypeptide. Accordingly, in some embodiments, administration of an IFN-γ polypeptide variant as disclosed herein to a subject may confer reduced capacity to upregulate PD-L1 expression in the subject, as compared to a reference polypeptide. The capacity to upregulate expression of PD-L1 can be reduced by at least, or at least about, 10%, 15%, 20%, 25%, 30%, 35%, 40%, 45%, 50%, 55%, 60%, 65%, 70%, 75%, 80%, 85%, 90%, 95%, or 100%, or a range of any two of the proceeding values, for example from about 20% to about 60% (inclusive of values in between these percentages), as compared to the capacity to upregulate PD-L1 expression by a reference polypeptide lacking the at least one amino acid substitution (e.g., a wild-type IFN-γ polypeptide). Accordingly, in some embodiments, administration of an IFN-γ polypeptide variant as disclosed herein to a subject may confer a reduction in capacity to upregulate PD-L1 expression by at least about 10%, about 20%, about 30%, about 40%, about 50%, about 60%, about 70%, about 80%, about 90%, or about 100% as compared to the capacity to upregulate PD-L1 expression by a reference polypeptide. In some embodiments, administration of a disclosed IFN-γ polypeptide variant to a subject may confer a reduction in capacity to upregulate PD-L1 expression ranging from about to about 20% to about 50%, about 40% to about 70%, about 60% to about 90%, about 70% to about 100%, about 50% to about 100%, about 60% to about 90%, or about 70% to about 80% as compared to the capacity to upregulate PD-L1 expression by a reference polypeptide.

In some embodiments, the administered polypeptide substantially retains its capacity to upregulate expression of one or more of MHC Class I molecules, e.g. HLA-A, HLA-B, and HLA-C, as compared to a reference polypeptide lacking the at least one amino acid substitution such as, e.g., a wild-type IFN-γ polypeptide. Accordingly, in some embodiments, administration of an IFN-γ polypeptide variant as disclosed herein to a subject may retain its capacity to upregulate expression of one, two, or all three HLA-A, HLA-B, and HLA-C, as compared to a reference polypeptide. In some embodiments, the administered polypeptide has reduced capacity to upregulate expression of PD-L1 while substantially retaining its capacity to upregulate expression of one or more MHC Class I molecules in the subject.

In some embodiments, the administration of the polypeptide or nucleic acid molecule does not inhibit T-cell activity in the subject. In some embodiments, the administered recombinant polypeptide enhances antitumor immunity in a tumor microenvironment, as compared to a reference subject. In some embodiments, administration of an IFN-γ polypeptide variant as disclosed herein to a subject may confer enhanced innate immune responses which lead to tumor control. In some embodiments, administration of an IFN-γ polypeptide variant as disclosed herein to a subject may confer enhanced adaptive immune responses, e.g., those mediated by the cytotoxic T-lymphocyte-associated protein 4 (CTLA-4) and/or the programmed cell death receptor 1 (PD-1) as well as its ligand (PD-L1, which is also named B7-H1). In some embodiments. The antitumor immunity in a tumor microenvironment can be enhanced by at least about 10%, 15%, 20%, 25%, 30%, 35%, 40%, 45%, 50%, 55%, 60%, 65%, 70%, 75%, 80%, 85%, 90%, 95%, or 100%, or a range of any two of the proceeding values, for example from about 20% to about 60% (inclusive of values in between these percentages), as compared to the antitumor immunity in an untreated subject under similar conditions. Accordingly, in some embodiments, administration of an IFN-γ polypeptide variant as disclosed herein to a subject may confer an enhanced antitumor immunity in a tumor microenvironment by at least about 10%, about 20%, about 30%, about 40%, about 50%, about 60%, about 70%, about 80%, about 90%, or about 100% as compared to the antitumor immunity in an untreated subject under similar conditions. In some embodiments, administration of a disclosed IFN-γ polypeptide variant to a subject may confer an enhancement in antitumor immunity ranging from about to about 20% to about 50%, about 40% to about 70%, about 60% to about 90%, about 70% to about 100%, about 50% to about 100%, about 60% to about 90%, or about 70% to about 80% in a tumor microenvironment as compared to the antitumor immunity in an untreated subject under similar conditions.

In some embodiments, the subject is a mammal. In some embodiments, the mammal is human. In some embodiments, the subject has or is suspected of having a health disease associated with inhibition of cell signaling mediated by the cell surface receptor. In some particular embodiments, the health disease is a cancer or a chronic infection.

Systems or Kits

Systems or kits of the present disclosure include one or more of any of the polypeptides, IFN-γ polypeptide variants, nucleic acids, vectors, or pharmaceutical compositions disclosed herein as well as syringes (including pre-filled syringes) and/or catheters (including pre-filled syringes) used to administer any of the recombinant polypeptides, IFN-γ polypeptide variants, nucleic acids, vectors, or pharmaceutical composition to an individual. The kits also include written instructions for using of any of the recombinant polypeptides, IFN-γ polypeptide variants, nucleic acids, vectors, or pharmaceutical composition disclosed herein as well as syringes and/or catheters for use with their administration.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All publications and patent applications mentioned in this disclosure are herein incorporated by reference to the same extent as if each individual publication or patent application was specifically and individually indicated to be incorporated by reference.

No admission is made that any reference cited herein constitutes prior art. The discussion of the references states what their authors assert, and the inventors reserve the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure, and are to be included within the spirit and purview of this application.

EXAMPLES

Additional embodiments are disclosed in further detail in the following examples, which are provided by way of illustration and are not in any way intended to limit the scope of this disclosure or the claims.

Example 1

General Experimental Procedures

The practice of the present disclosure will employ, unless otherwise indicated, conventional techniques of molecular biology, microbiology, cell biology, biochemistry, nucleic acid chemistry, and immunology, which are known to those skilled in the art. Such techniques are explained in the literature, such as, *Molecular Cloning: A Laboratory Manual*, fourth edition (Sambrook et al., 2012) and *Molecular Cloning: A Laboratory Manual*, third edition (Sambrook and Russel, 2001), (jointly referred to herein as "Sambrook"); *Current Protocols in Molecular Biology* (Ausubel F M et al., eds., 1987, including supplements through 2014); *PCR: The Polymerase Chain Reaction*, (Mullis et al., eds., 1994); Beaucage et al. eds., *Current Protocols in Nucleic Acid Chemistry*, John Wiley & Sons, Inc., New York, 2000, (including supplements through 2014), *Gene Transfer and Expression in Mammalian Cells* (Makrides, ed., Elsevier Sciences B.V., Amsterdam, 2003), and *Current Protocols in Immunology* (Horgan K. and S. Shaw (1994) (including supplements through 2014). As appropriate, procedures involving the use of commercially available kits and reagents are generally carried out in accordance with manufacturer defined protocols and/or parameters unless otherwise noted.

Example 2

Crystal Structure of the Hexameric IFN-γ/IFN-γR1/IFN-γR2 Complex

This Example describes the results of experiments performed to determine the crystal structure of the hexameric complex 2:2:2 IFN-γ/IFN-γR1/IFN-γR2, which in turns helps elucidate the chemistry that drives each of the ligand-receptor interactions of the hexameric complex.

One challenge in understanding the integral role of IFN-γ signaling in coordinating essential immune functions has been due in large part to the structural complexity of the hexameric IFN-γ/IFN-γR1/IFN-γR2 complex. Without being bound to any particular theory, it is believed that the lack of a detailed understanding of this IFN-γ hexameric structure is due to the low affinity of IFN-γR2 for IFN-γ, IFN-γR1, or IFN-γ/IFN-γR1, and this property of IFN-γR2 has caused a challenge for solving the atomic structure of the complete IFN-γ signaling complex. The partial 2:2 IFN-γ/IFN-γR1 complex (PDB:1FG9) was previously solved. However, the structure of the complete hexameric complex 2:2:2 IFN-γ/IFN-γR1/IFN-γR2 remains unsolved, presumably due to low affinity of IFN-γR2 for either IFN-γ, IFN-γR1, or its low affinity to the 2:2 IFN-γ/IFN-γR1 proteins.

In the experiments described in this Example, to overcome the IFN-γR2 low affinity problem, all of the components of the IFN-γ signaling complex were expressed and individually purified. The receptors IFN-γR1 F05 and IFN-γR2 were expressed in HEK293 GnTI– cells using a lentivirus infection protocol (Bandaranayake et al., 2011). The cytokine, IFN-γ, was expressed in Hi5 insect cells. Crystals were subsequently screened for diffraction, and diffraction data was collected at 3.1. The structure was solved by molecular replacement using the 2:2 IFN-γ/IFN-γR1 intermediate complex (PDB: 1FG9) and IFN-γR2 (PDB: 5EH1). As shown in FIG. 1, the 2:2:2 IFN-γ receptor complex has a two-fold symmetrical structure with the IFN-γR2. In FIG. 1, the structure of the IFN-γ complex with IFN-γR1 and IFN-γR2 is shown as a homodimeric cytokine which binds two IFN-γR1 and two IFN-γR2 receptors. The IFN-γR1 binding sites within the IFN-γ molecule are termed Site Ia and Site Ib, whereas the IFN-γR2 binding sites within the IFN-γ molecule are termed Site IIa and Site IIb. In these experiments, IFN-γR2 was found to bind to the composite interface formed by the high affinity 2:2 IFN-γ/IFN-γR1 intermediate complex (See FIG. 1).

Figure 2:
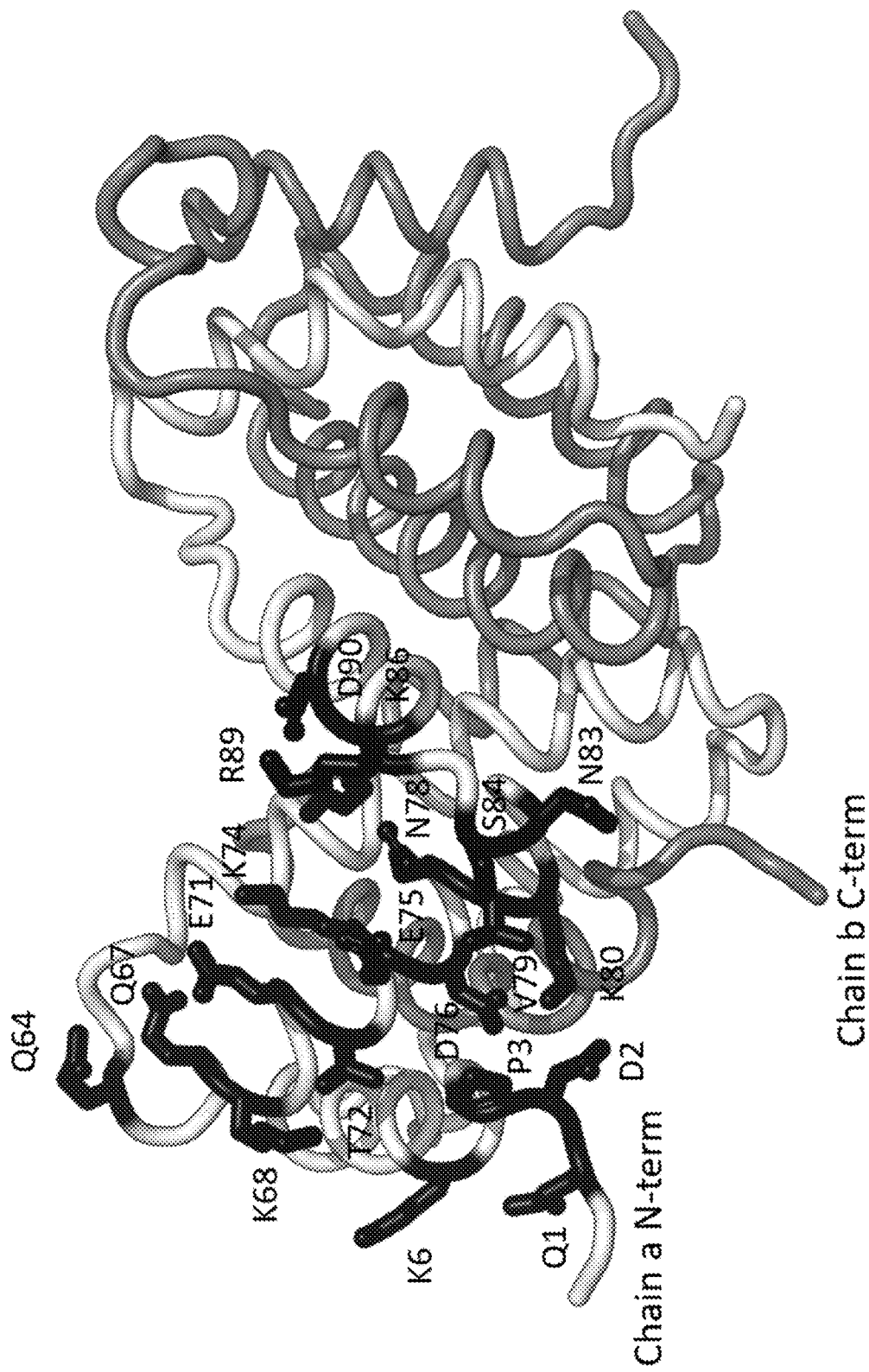
FIG. 2 graphically illustrates amino acid residues in IFN-γ molecule that interact with IFN-γR2.

The structure of the IFN-γ signaling complex described herein helps elucidate at least two long-standing questions in the field. The first question being that, despite the previously lack of measurable affinity between IFN-γ and IFN-γR2, the complete hexameric IFN-γ complex shown in FIG. 1 demonstrates that an interaction exists between IFN-γ and IFN-γR2 which includes a site II interface. Secondly, the IFN-γ signaling complex described herein has revealed the chemistry that drives ligand-receptor interactions at each of the site IIa and IIb interfaces of the complex. In FIG. 2, the amino acid residues positions at one of the two IFN-γR2 binding interfaces are shown as black sticks. In this figure, IFN-γ amino acid residues that interact with IFN-γR2 include Q1, D2, P3, K6, Q64, Q67, K68, E71, T72, K74, E75, D76, N78, V79, K80, N83, S84, K86, R89, and D90. In addition, it was observed that ligand-receptor interactions at each of site IIa and IIb are further stabilized by hydrogen bonds distributed throughout the interface.

As discussed in further detailed below, in addition to revealing the mechanism of IFN-γR2 recognition and the specific contacts important for IFN-γ/IFN-γR2 binding, the structure of the complete IFN-γ signaling complex also provided insights into the design of partial agonists to affect signal transduction mediated by IFN-γ in ways not before possible. In addition, the experimental data described herein leads to the discovery in that some of the IFN-γ activities can be uncoupled and modulated individually. As described in greater detail below, some IFN-γ partial agonists can achieve biased expression of class I MHC antigen presentation and PD-L1 surface expression, which molecules may provide new avenues for intervening in the checkpoint blockade signaling axis.

Example 3

Structure-Based Design of IFN-γ Partial Agonist with Biased Signaling Outputs

This Example describes the results of experiments performed to design IFN-γ partial agonists for biased MHC I/PD-L1 expressions based on the crystal structure of the hexameric complex 2:2:2 IFN-γ/IFN-γR1/IFN-γR2 described in Example 2.

Figure 3A:
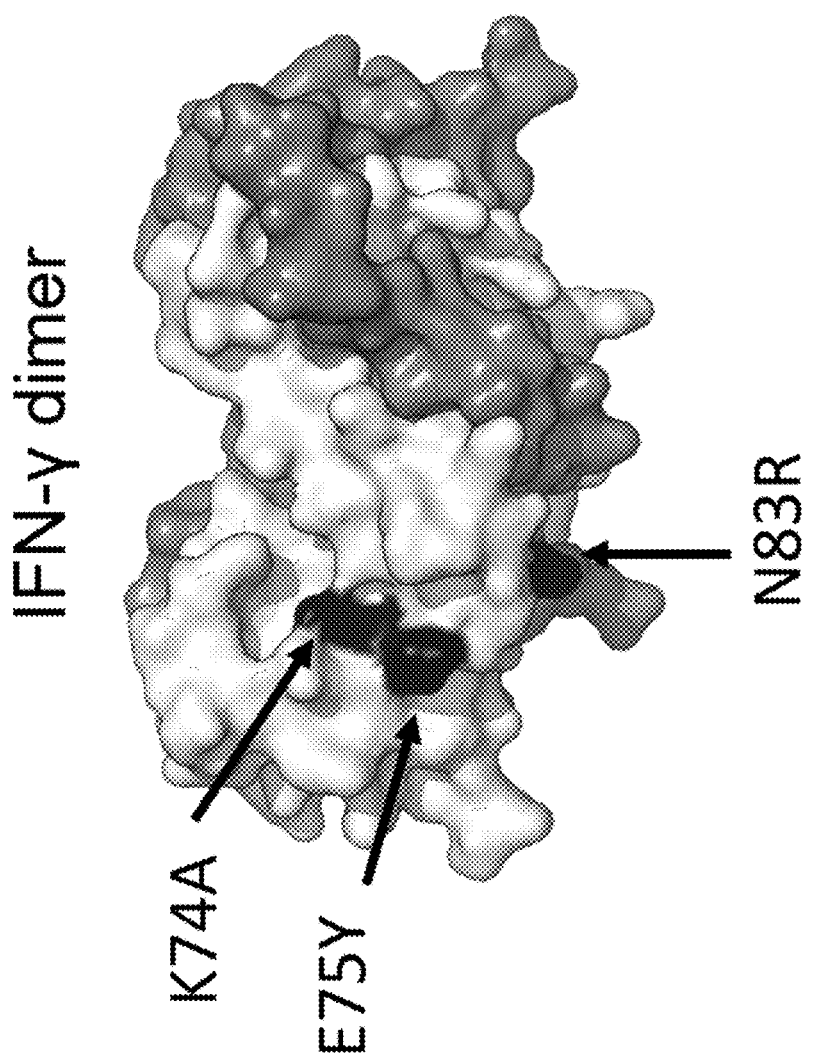
FIGS. 3A-3C graphically summarize the results from experiments performed to illustrate a non-limiting example of IFN-γ polypeptide variants in accordance with some embodiments of the disclosure.
Figures 3B, 3C:
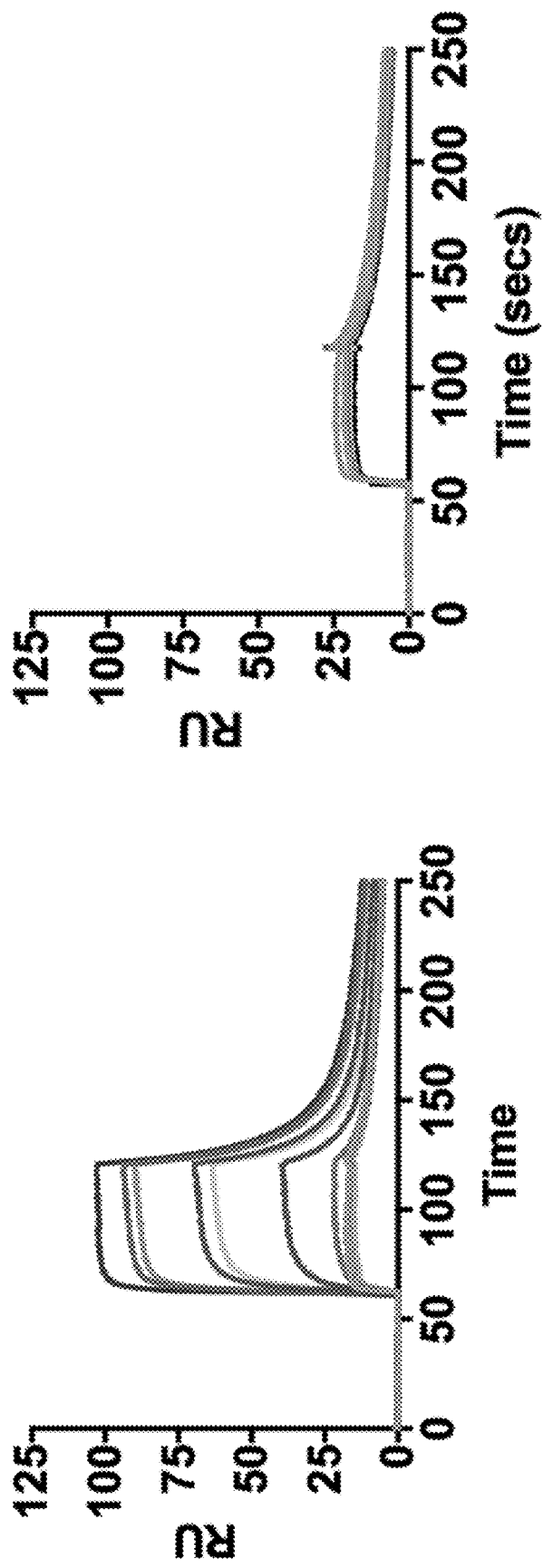

The structure of the IFN-γ signaling complex as described in Example 2 above provided opportunities to address new questions to further understand IFN-γ signaling and activity. By identifying the shared interactions, previously unknown, at sites IIa/IIb, one now can better understand IFN-γ signaling at each step of complex formation. Since IFN-γ is a dimeric cytokine driving the dimerization of four receptors, further experiments were performed to design and generate variants of IFN-γ to affect one or more of the different signaling intermediates. The design of the partial agonists was achieved by first engineering a version of IFN-γ that abolished binding to IFN-γR2 receptor. Based on the structure described in Example 2, a triple IFN-γ mutant having three amino acid substitutions K74A, E75Y, and N83R (See FIG. 3A) was designed and validated for the loss of measurable binding to IFN-γR2 as determined by surface plasmon resonance (FIGS. 3B-3D). Without being bound to any particular theory, several other mutations or combinations thereof of the IFN-γR2 binding site amino acids of IFN-γ as indicated in the crystal structure (FIG. 2), either alone or in combination with mutations within the IFN-γR1 binding site, could also result in similar effects on IFN-γR2 binding.

In FIG. 3A, which depicts a surface view of the mutated IFN-γ dimer (white and dark gray surfaces), the mutations E74A, E75Y, and N75R (black surfaces) were engineered into the IFN-γ molecule at the IFN-γR2 binding interface and predicted to alter binding. FIG. 3B depicts traces of a surface plasmon resonance (SPR) experiment measuring affinity of IFN-γR2 for the wild-type 2:2 IFN-γ/IFN-γR1 intermediate complex. In comparison, IFN-γR2 binding to the mutant 2:2 IFN-γ (K74A/E75Y/N75R)/IFN-γR1 complex is reduced compared to the wild-type IFN-γ, as evidenced by the SPR traces (as shown in FIG. 3C). In these surface plasmon resonance analyses, GE Biacore T100 was used to measure the KD by equilibrium methods. Approximately 100 RU of IFN-γR1 was captured on a SA-chip (GE) including a reference channel of an unrelated cytokine receptor (IL-2Rβ). The saturating concentration for both IFN-γ wild-type or IFN-γK74A/E75Y/N83A was 50 nM and was present in all dilutions of IFN-γR2.

Figures 4A, 4B:
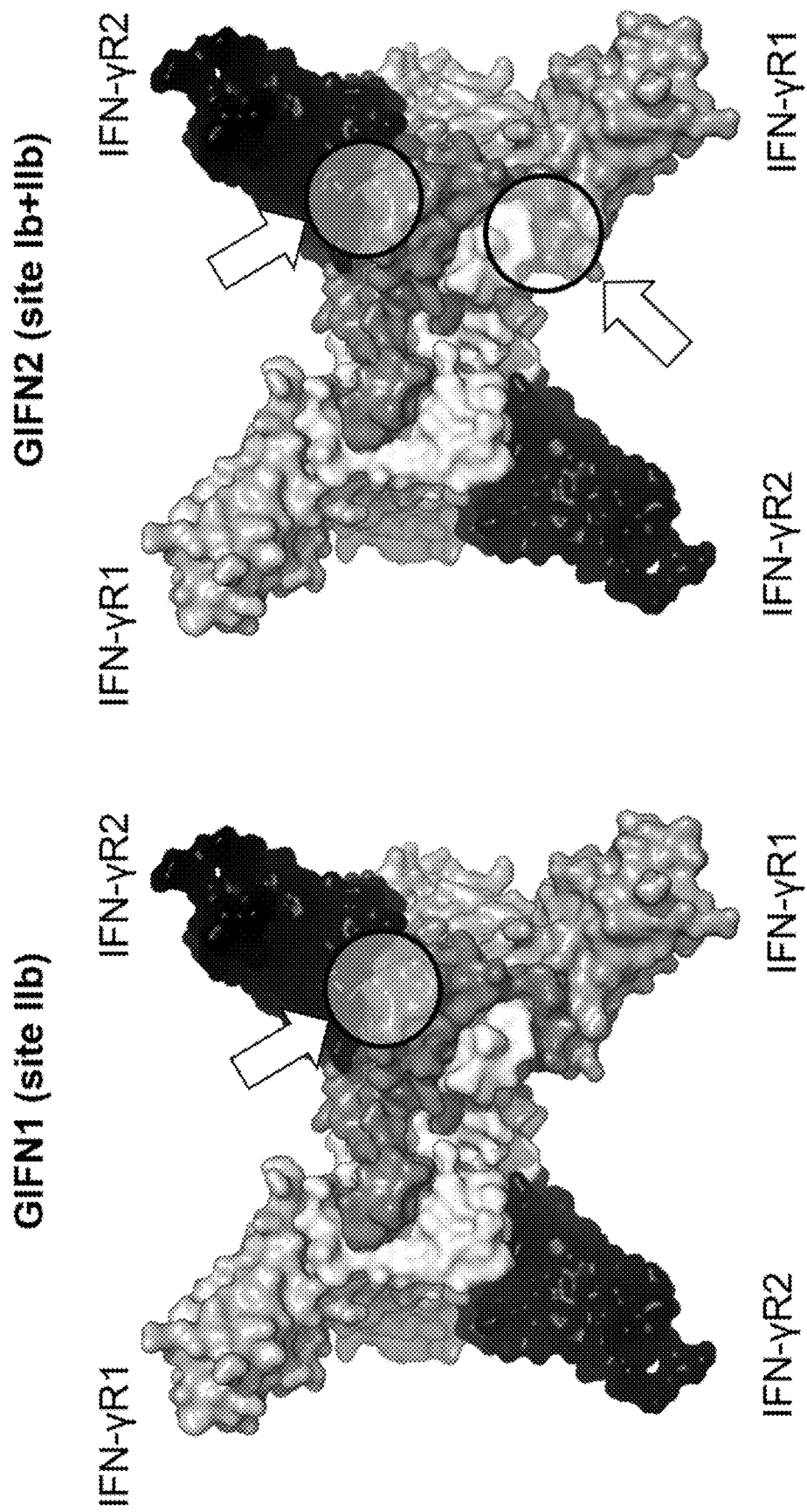
FIGS. 4A-4D graphically illustrate four non-limiting exemplary IFN-γ polypeptide variants in accordance with some embodiments of the disclosure. In these drawings, IFN-γ molecule (white and gray surfaces) is a homodimeric cytokine which binds two IFN-γR1 receptors (light gray) and two IFN-γR2 (black) receptors.
Figures 4C, 4D:
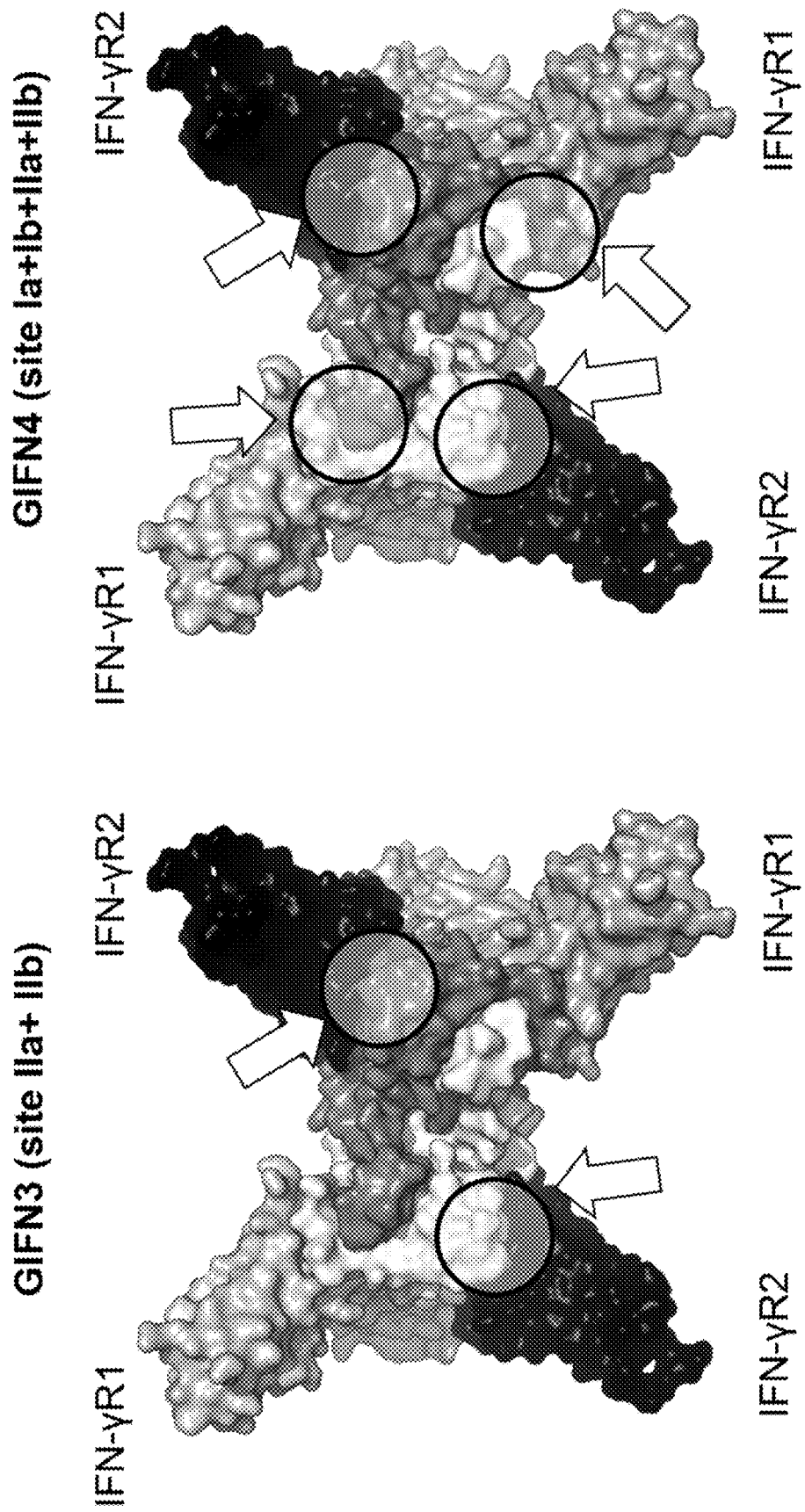
Figures 5A, 5B:
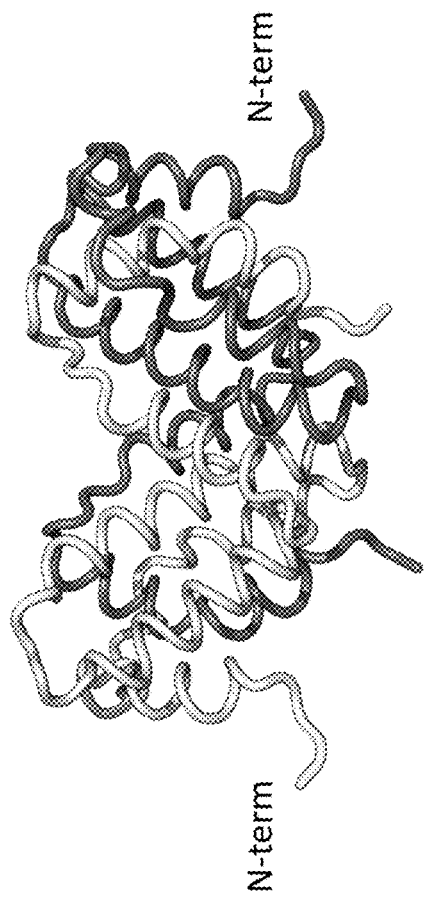
FIGS. 5A-5B depict a homodimeric structure (FIG. 5A) and amino acid sequence of a wild-type IFN-γ monomeric molecule (FIG. 5B; SEQ ID NO: 1).

Several additional IFN-γ polypeptide variants were also designed and validated. Exemplifications of these variants are illustrated in FIGS. 4A-4D. In these drawings, IFN-γ molecule (white and tan gray surfaces) is a homodimeric cytokine which binds two IFN-γR1 receptors (light gray) and two IFN-γR2 (black) receptors. FIG. 4A shows the structure of the IFN-γ variant GIFN1, in which three amino acid substitutions K74A, E75Y, N83R were engineered into site IIb of the IFN-γ molecule. FIG. 4B shows the structure of the IFN-γ variant GIFN2 which contains three amino acid substitutions K74A, E75Y, N83R engineered into site IIb, and H111D substitution engineered into site Ib of the IFN-γ molecule. FIG. 4C shows the structure of the IFN-γ variant GIFN3, in which three amino acid substitutions K74A, E75Y, N83R were engineered into sites IIa and IIb of the IFN-γ molecule. FIG. 4D shows the structure of the IFN-γ variant GIFN4 which contains the following amino acid substitutions in the IFN-γ molecule: K74A, E75Y, N83R in sites IIa and IIb; A23E, D24E, N25K in site Ia; and H111D in site Ib.

Figures 6A, 6B:
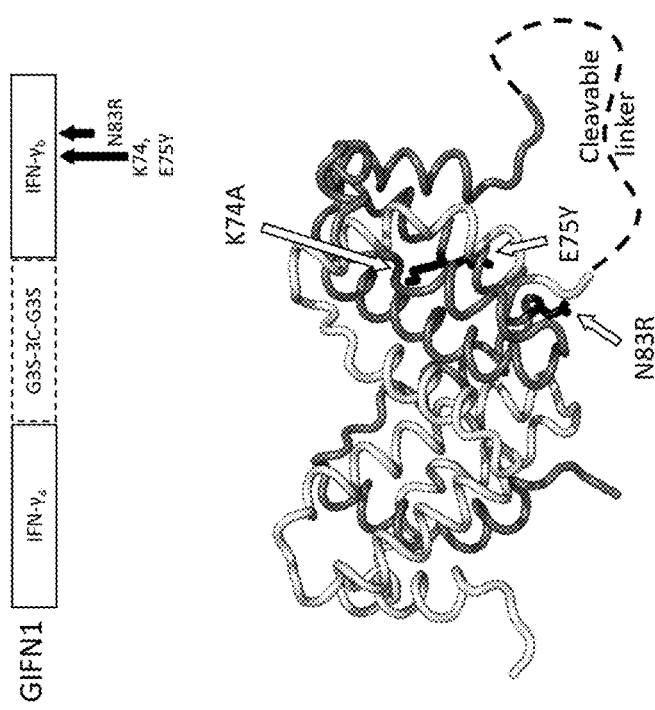
FIGS. 6A-6B depict the structure and amino acid sequence of GIFN1, which is a non-limiting example of an IFN-γ polypeptide variant in accordance with some embodiments of the disclosure. In the amino acid sequence of IFN-γ variant GIFN1 (SEQ ID NO: 2, FIG. 6B), three amino acid substitutions K74A, E75Y, N83R, which were engineered into site IIb of the IFN-γ molecule, are denoted by bold letters. The amino acid sequences of two IFN-γ monomers are linked to each other via a cleavable peptide linker (shown in italic letters).
Figures 7A, 7B:
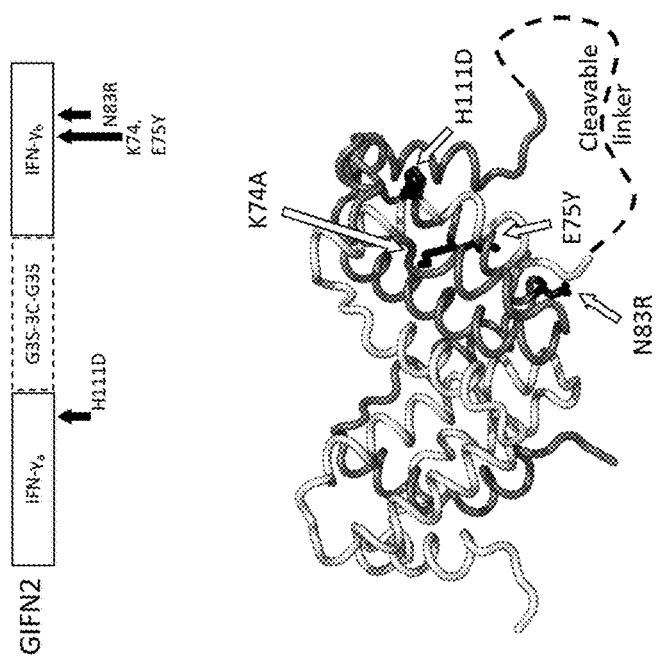
FIGS. 7A-7B depict the structure and amino acid sequence of GIFN2, which is another non-limiting example of an IFN-γ polypeptide variant in accordance with some embodiments of the disclosure. In the amino acid sequence of IFN-γ variant GIFN2 (SEQ ID NO: 3, FIG. 7B), three amino acid substitutions (K74A, E75Y, N83R) were engineered into site IIb (bold letters), and H111D substitution was engineered into site Ib of the IFN-γ molecule (boxed). The amino acid sequences of two IFN-γ monomers are linked to each other via a cleavable peptide linker (italic letters).
Figures 8A, 8B:
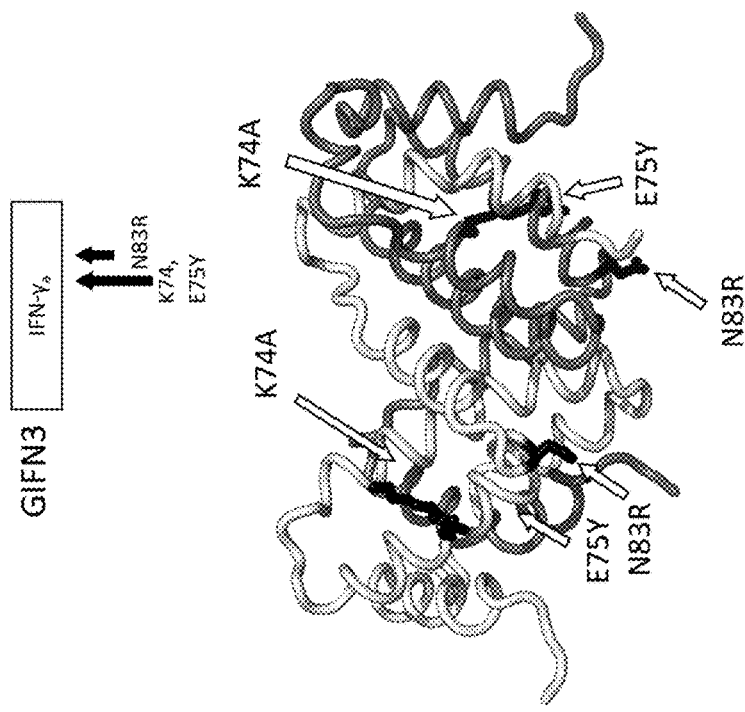
FIG. 8A depicts the homodimeric structure of GIFN3, which is another non-limiting example of an IFN-γ polypeptide variant in accordance with some embodiments of the disclosure.
FIG. 8B depicts the amino acid sequence of the GIFN3 monomer (SEQ ID NO: 4), in which three amino acid substitutions K74A, E75Y, N83R were engineered into sites IIa and IIb of the IFN-γ molecule (shown in bold letters).
Figures 9A, 9B:
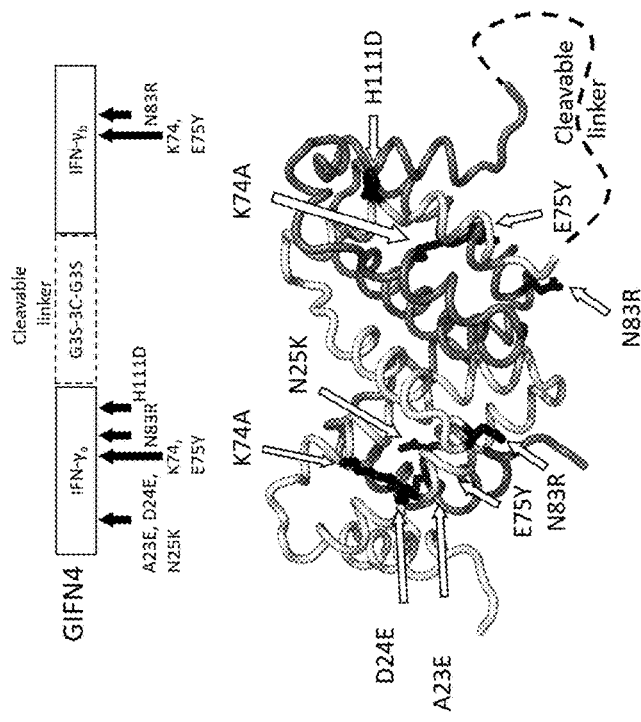
FIGS. 9A-9B depict the structure and amino acid sequence of GIFN4, which is yet another non-limiting example of an IFN-γ polypeptide variant in accordance with some embodiments of the disclosure.

Previous attempts to engineer heterodimeric versions of IFN-γ to query the IFN-γ signaling axis were limited due to the unknown loss of activity caused by the addition of linkers between the two monomers of the dimeric IFN-γ molecule. Structural analysis of the IFN-γ single chain heterodimers against the full signaling complexed revealed the engineered linkers introduced steric alterations preventing IFN-γR2 binding. In the present disclosure, this problem was overcome by engineering a cleavable linker between the two monomers of the dimeric IFN-γ molecule. An example of such a chimeric design was constructed as shown in FIGS. 6A-6B, where the chimeric IFN-γ molecule GIFN1 contains, in the N-terminal to C-terminal direction, a wild-type sequence of IFN-γ, a cleavage linker, and a second IFN-γ sequence with amino acid substitutions K74A, E75Y, and N83R. Using the linker strategy, together with different combinations of site II and site III mutations, it has now become possible to measure IFN-γ signaling and activities for different partial agonists exhibiting a topological control of receptors in the hexameric complex. Another example of such a chimeric design is shown in FIGS. 7A-7B, where the chimeric IFN-γ molecule GIFN2 contains, in the N-terminal to C-terminal direction, a first IFN-γ molecule having the amino acid substitution H111D, a cleavage linker, and a second IFN-γ sequence with amino acid substitutions K74A, E75Y, and N83R. In yet another example of such a design chimeric design, the chimeric IFN-γ molecule GIFN4 contains, in the N-terminal to C-terminal direction, a first IFN-γ sequence having the amino acid substitution A23E, D24E, N25K, and H111D; a cleavage linker, and a second IFN-γ sequence with amino acid substitutions K74A, E75Y, and N83R (FIGS. 9A-9B). The ability to control receptor topology of the mutant IFN-γ molecules was also confirmed by receptor dimerization studies.

Example 4 pSTAT1 Signaling and Antiviral Activity

This Example describes the results of experiments performed to illustrate dose-dependent of phospho-STAT1 signaling in response to the IFN-γ variants described in Examples 2 and 3 above.

Figure 10A:
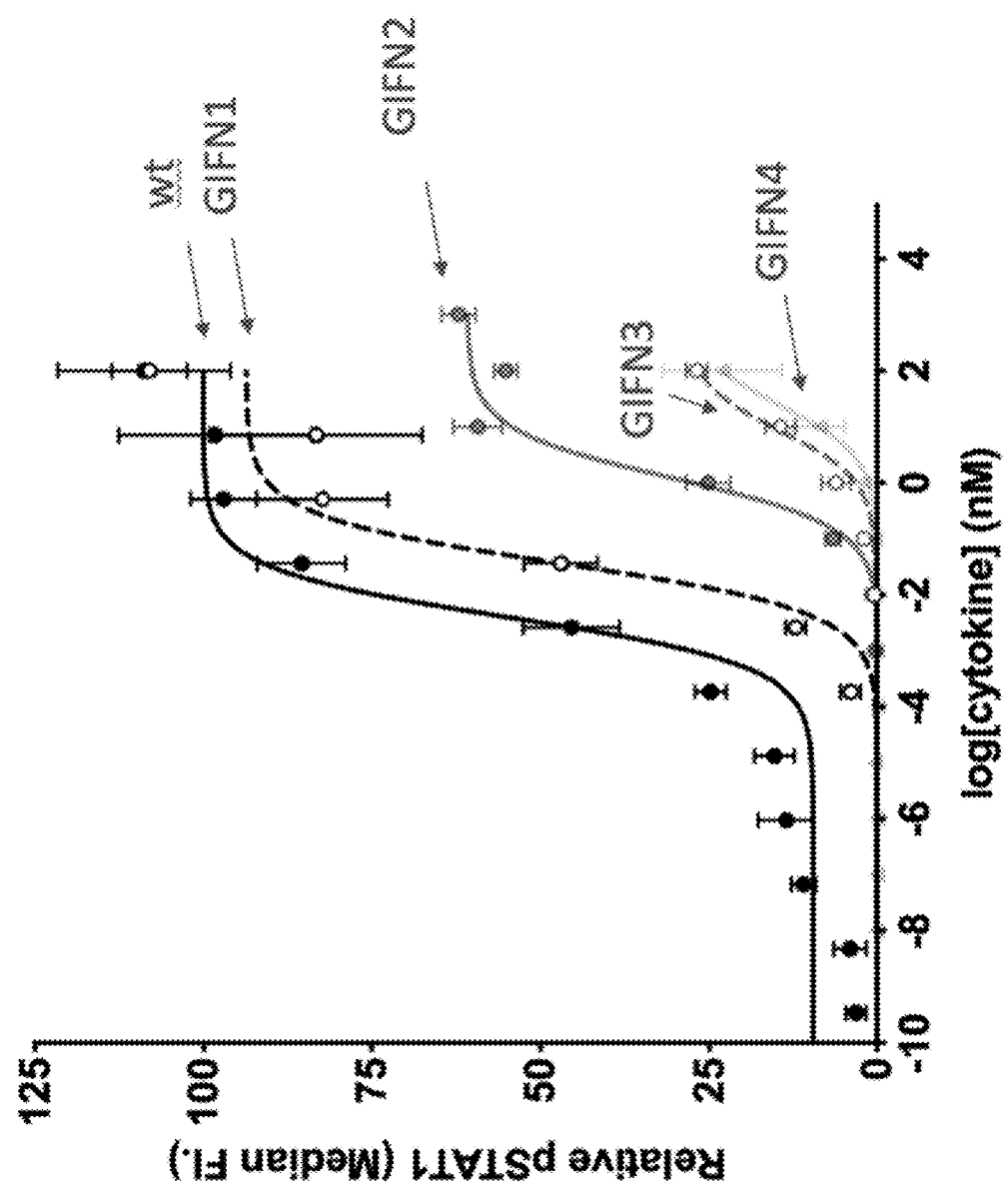
FIGS. 10A-10I graphically summarize the results from experiments performed to illustrate a non-limiting example of a method for modulating IFN-γ-mediated signaling in accordance with some embodiments of the disclosure. As shown, IFN-γ partial agonists produce biased Class I MHC antigen presentation (HLA-ABC) relative to PD-L1 expression by altering phospho-STAT signaling.

In these experiments, Hap1 cells were plated in a 96 well format and treated with either wild-type IFN-γ or partial agonists at varying concentrations for 15 minutes at 37° C. The media was removed and cells were detached with trypsin (Gibco) for 5 minutes at 37° C. Cells were transferred to a deep-well 96 well block containing 10% PFA by volume and incubated for 15 minutes at RT, washed 3 times with PBSA, resuspended with 100% Methanol overnight, and washed 3 times before and after incubating with Alexa Fluor® 488 conjugated anti-pSTAT1 antibody (Cell Signaling). The $EC_{50}$ and $E_{max}$ of signaling was determined by fitting the data to a sigmoidal dose-response (GraphPad PRISM software version 7). As shown in FIG. 10A, the level of phospho-STAT1 signaling in response to the IFN-γ variants and wild-type IFN-γ was found to be in a dose-dependent manner.

Example 5

Stimulation of A549 Cells

This Example describes the results of experiments performed to investigate the levels of PD-L1 expression and MHC-I expression in an A549 lung cancer line in response to the IFN-γ variants described in Examples 2 and 3 above.

In these experiments, A549 cells (ATCC CCL-185) were cultured at 37° C. in 5% CO2 and RPMI 1640 (Thermo Fisher Scientific) containing 10% FBS and 100 U/mL penicillin/streptomycin (GIBCO). Cells were plated into 48 well plates and stimulated for 48 hours with various concentrations of IFN proteins (e.g., with IFN-γ (WT) or IFN-γ variants at 0.1 nM, 0.5 nM, 2.5 nM, 12.5 nM, and 62.5 nM doses (see, FIG. 10B and FIG. 10D, bars from left to right).

After 48 hours, cells stimulated with each IFN-γ polypeptide were harvested using 0.25% Trysin-EDTA (GIBCO) and analyzed by flow cytometry using an LSR II (BD). Dead cells were discriminated using the Live/Dead Aqua Fixable Dead Cell Stain Kit (Invitrogen), non-specific antibody binding was minimized using Human FC Block (BD) and surface staining was performed with PE-Dazzle™ conjugated anti-PD-L1 (clone 29E.2A3, BioLegend) and v450 conjugated anti-HLA-ABC (clone G46-2.6, BD). The Median Fluorescence Intensity (MFI) change was calculated by subtracting the MFI of non-stimulated controls from the MFI of stimulated samples. Statistical comparisons of WT IFN-γ versus its analogs were performed using One-way ANOVA followed by Dunnett's multiple comparisons test in GraphPad Prism v7.04. For quantification of gene expression by qPCR, 600,000 cells were plated in a 6-well format and treated with proteins for 48-hours. RNA was extracted (RNeasy Micro Kit, Qiagen), 1.5 µg was then used for RT-PCR (High Capacity RNA-to-cDNA Kit, Applied Biosystems), and measured by qPCR (PowerSYBR Green PCR Master Mix, Applied Biosystems) on a QuantStudio 3 instrument (Applied Biosystems) per manufacturer's instructions. Primers were purchased from Operon Technologies Inc. for 18S (fwd 5'-GTAACCCGTTGAACCC-CATT-3' SEQ ID NO: 7, rev 5'-CCATC-CAATCGGTAGTAGCG-3' SEQ ID NO: 8), HLA-A (fwd 5'-CCAGGTAGGCTCTCAACTG-3' SEQ ID NO: 9, rev 5'-CCAGGTAGGCTCTCAACTG-3' SEQ ID NO: 10), HLA-B (fwd 5'-AACCGTCCTCCTGCTGCTCTC-3' SEQ ID NO: 11, rev 5'-CTGTGTGTTCCGGTCCCAATAC-3' SEQ ID NO: 12), PD-L1 (fwd 5'-TGGCATTTGCT-GAACGCATTT-3' SEQ ID NO: 13, rev 5'-TGCAGCCAGGTCTAATTGTTTT-3' SEQ ID NO: 14).

Figure 10C:
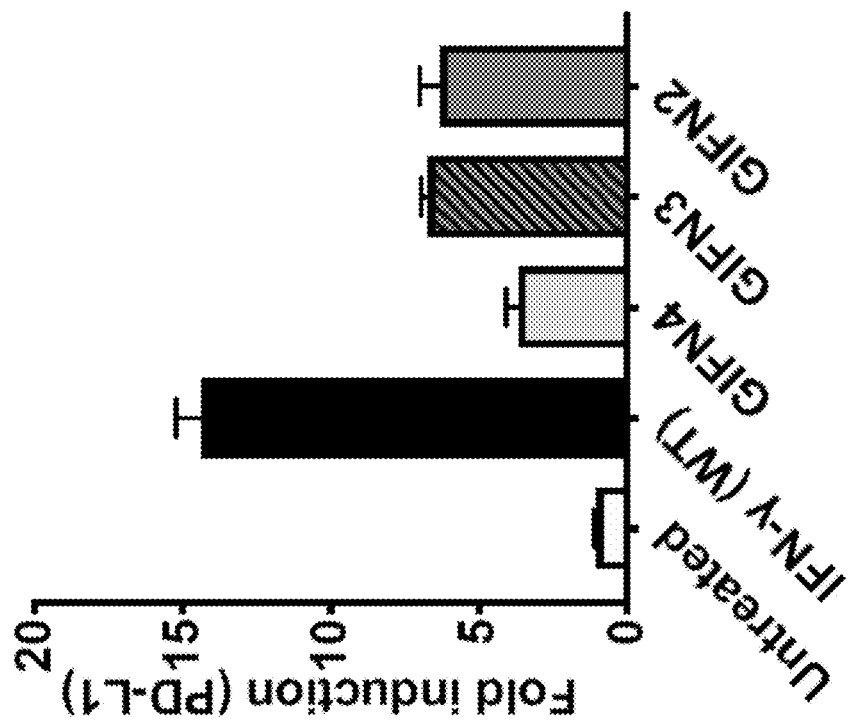
Figure 10B:
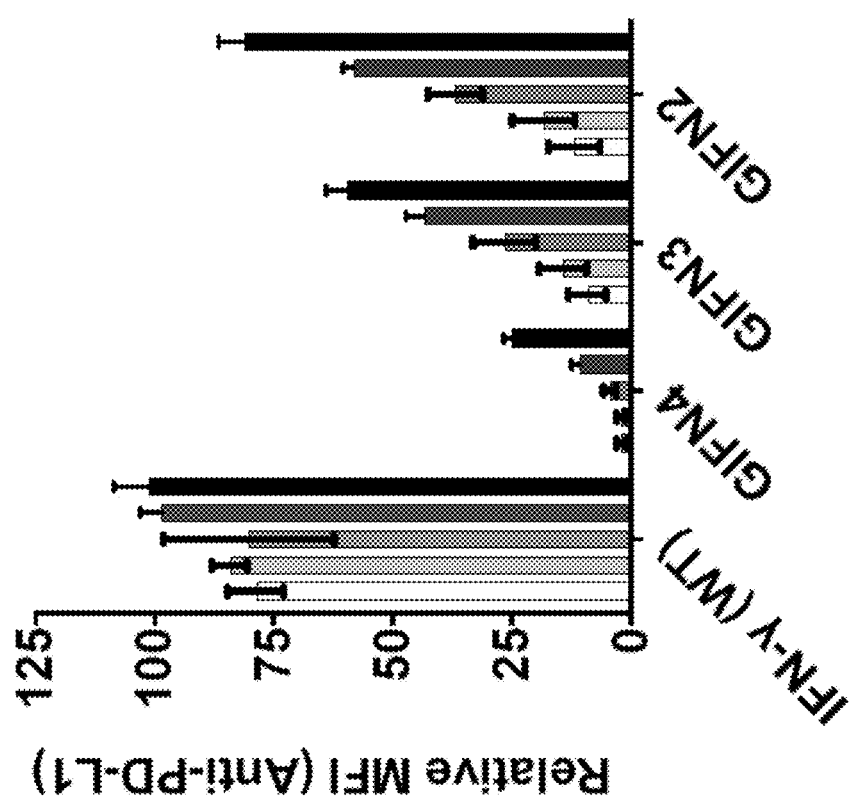
Figure 10E:
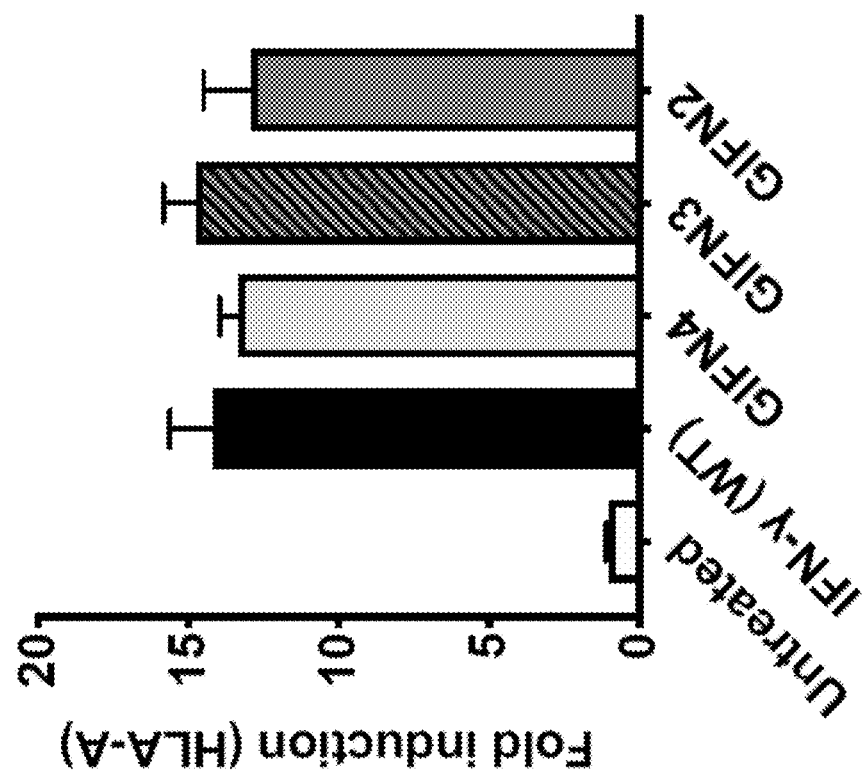
Figure 10D:
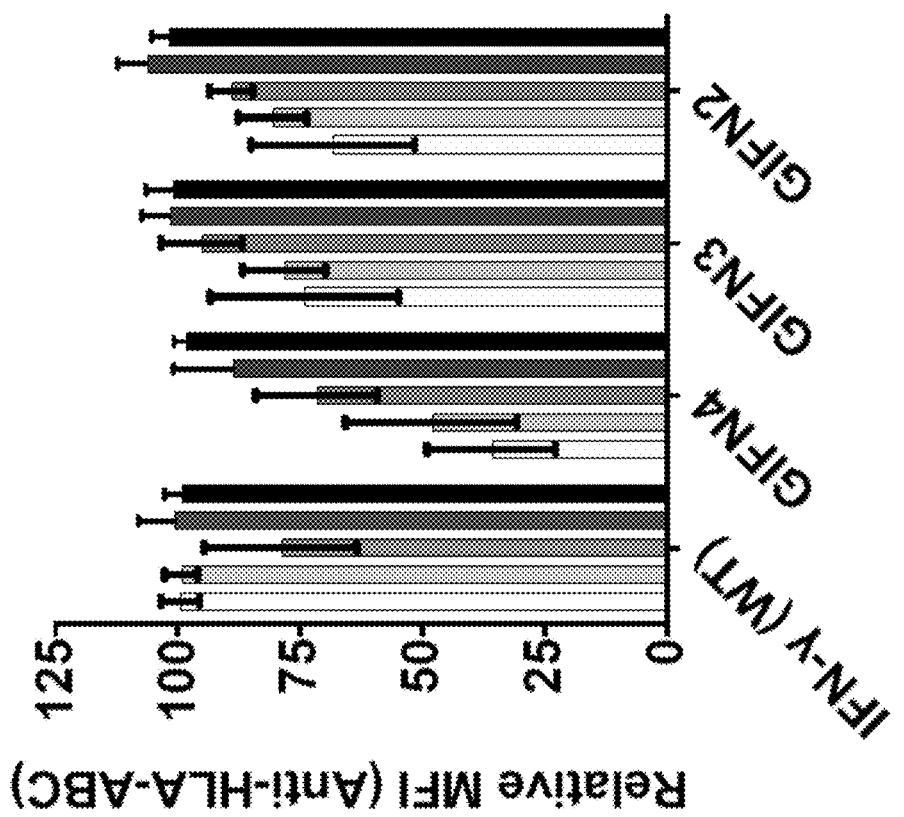

As shown in FIG. 10A-10E, it was observed that the IFN-γ partial agonists described in Examples 2-3 above produced biased Class I MHC antigen presentation (HLA-ABC) relative to PD-L1 expression. In FIG. 10B, A549 cells were treat with IFN-γ (WT) or IFN-γ variants at 0.1 nM, 0.5 nM, 2.5 nM, 12.5 nM, and 62.5 nM doses (bars from left to right). After 48 hours, the A549 cells were stained for PD-L1 expression and analyzed. In FIG. 10C, the expression of PD-L1 gene was measured by qPCR by treating A549 cells for 48 hours with 62.5 nM of each protein. In FIG. 10D, experiments were performed similarly to those described in FIG. 10B with the exception that Class I MHC was measured by FACS technique. In FIG. 10E, HLA-A gene expression was measured by qPCR by treating A549 cells for 48 hours with 62.5 nM of protein. As discussed above, while existing IFN-γ treatment would be a promising anti-cancer adjuvant, one major limiting factor is that while existing IFN-γ treatment of cancerous cells upregulates class I MHC antigen presentation, PD-L1 expression is also upregulated dampening the potential anticancer benefits. In these experiments, it was found that the expression of PD-L1 and class I MHC require different signaling thresholds to achieve full expression. Remarkably, the IFN-γ partial agonists of the present disclosure, when used at different concentrations, were observed to result in reduced levels of PD-L1 upregulation, while retaining potent capacity to upregulate MHC class I expression in A549 cells with the greatest bias exhibited by the variant GIFN4, as demonstrated by modulated MHC I:PD-L1 ratios relative to a reference ratio observed in control A549 cells treated with wild-type IFN-γ (see, FIG. 10H).

Taken together, the experiments described in this Example demonstrates that while all the partial agonists described above efficiently upregulate class I MHC expression in A549 cells, PD-L1 expression in these cells by the partial agonists is limited with the greatest bias exhibited by the variant GIFN4.

Example 6

Stimulation of Dendritic Cells

This Example describes the results of experiments performed to investigate the levels of PD-L1 expression and MHC-I expression in dendritic cells in response to the IFN-γ variants described in Examples 2 and 3 above.

Figure 10G:
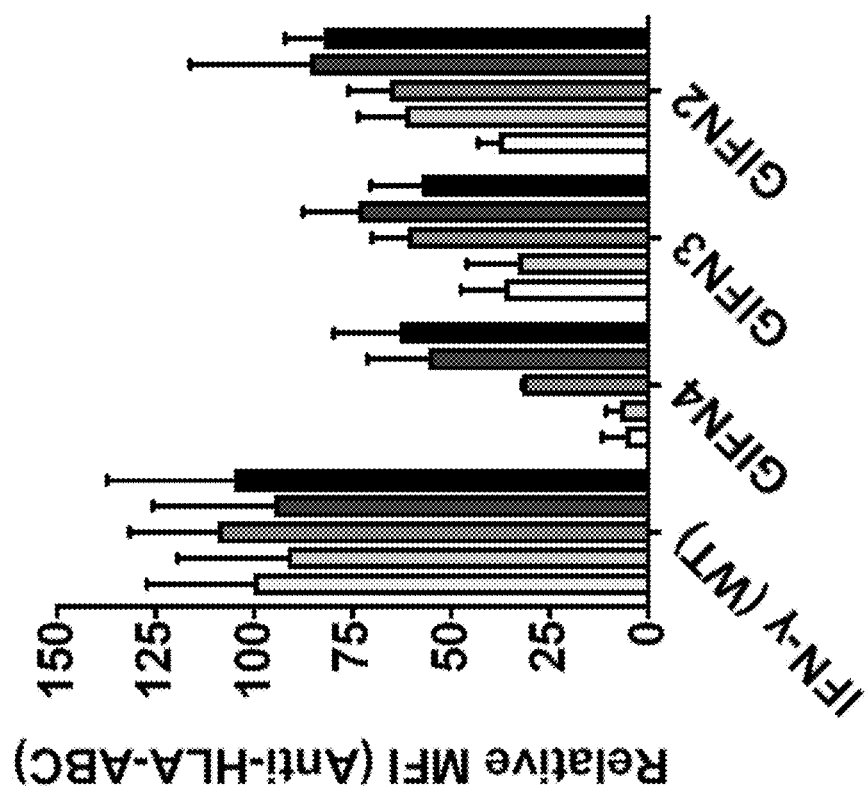
Figure 10F:
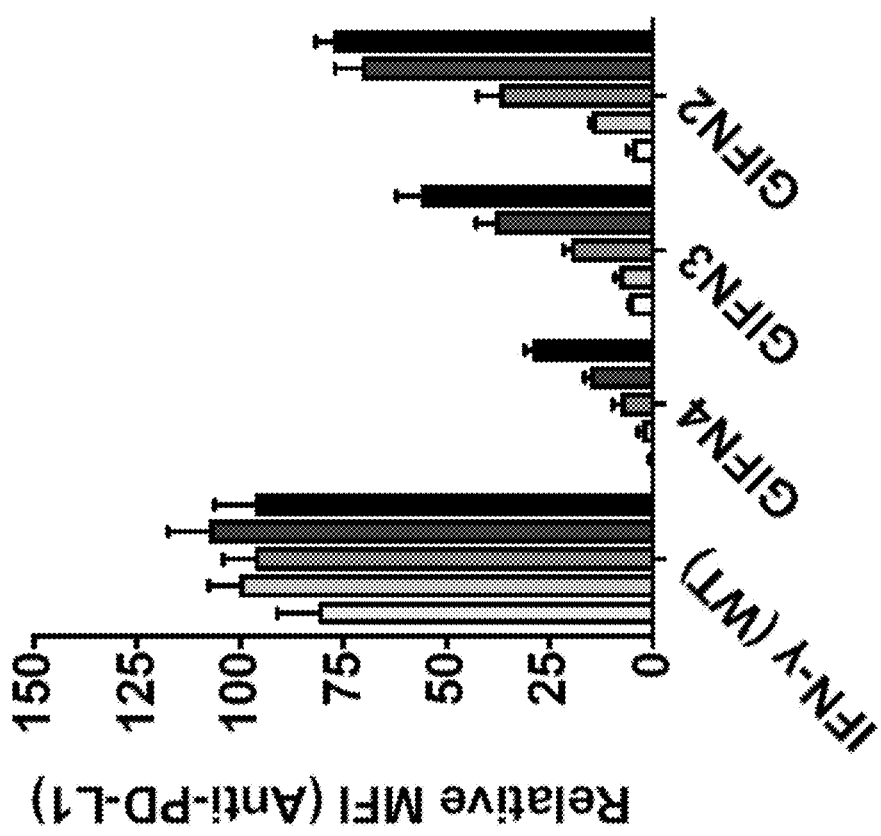
Figures 10H, 10I:
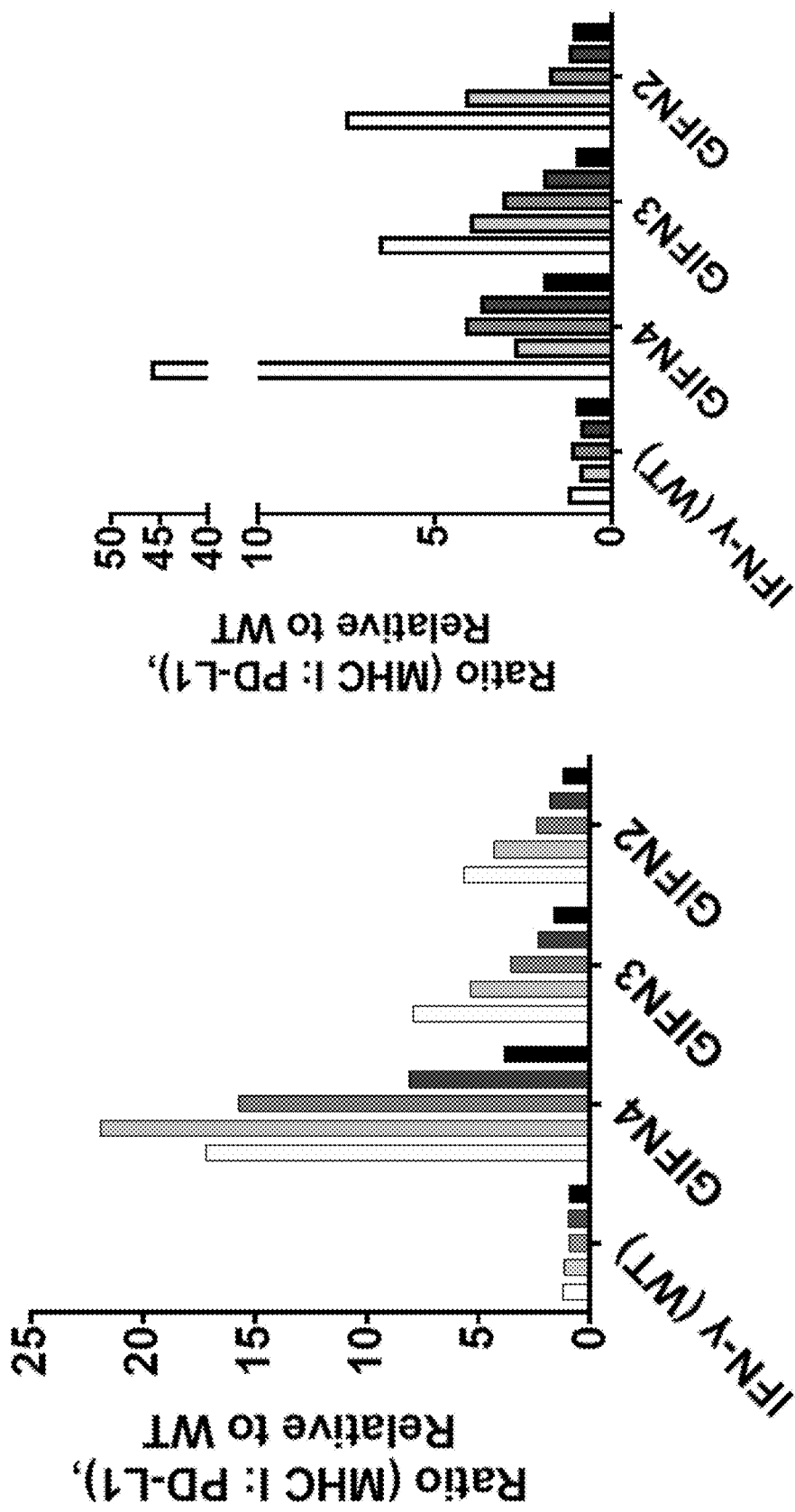

In these experiments, dendritic cells (DCs) were first purified from human blood as follows. Human blood DCs were enriched from blood in leukoreduction system chambers by Ficoll-Hypaque density gradient centrifugation, followed by magnetic enrichment with the EasySep Human Myeloid DC Enrichment kit (19061; StemCell Technologies). Enriched cells were stained with DAPI and lineage markers CD19 PE-Cy5 (Beckman Coulter); CD56 FITC, CD3 Alexa700 (BioLegend); CD11c PE-Cy7, HLA-DR v500, CD14 APC-H7 (BD); and CD304 PE (MACs Miltenyi Biotec). Dendritic cells were sorted on a BD FACsAria II as HLA-DR$^+$CD11c$^+$ cells which were negative for all other lineage markers. Purified DCs were subsequently stimulated for 48 hours with various concentrations of IFN proteins (e.g., with IFN-γ (WT) or IFN-γ variants at 0.1 nM, 0.5 nM, 2.5 nM, 12.5 nM, and 62.5 nM doses (see, FIG. 10F and FIG. 10G, bars from left to right). After 48 hours, dendritic cells stimulated with each IFN-γ polypeptide were analyzed by flow cytometry using an LSR II (BD). Dead cells were discriminated using the Live/Dead Aqua Fixable Dead Cell Stain Kit (Invitrogen), non-specific antibody binding was minimized using Human FC Block (BD) and surface staining was performed with PE-Dazzle conjugated anti-PD-L1 (clone 29E.2A3, Biolgend) and v450 conjugated anti-HLA-ABC (clone G46-2.6, BD) using the same procedures as described in Example 5 above. As shown in FIG. 10F-10G, it was observed that the IFN-γ partial agonists described in Examples 2-3 above produced biased Class I MHC antigen presentation (HLA-ABC) relative to PD-L1 expression in dendritic cells. Remarkably, these IFN-γ partial agonists, when used at different concentrations were observed to result in reduced levels of PD-L1 upregulation, while retaining potent capacity to upregulate MHC class I expression in dendritic cells with the greatest bias exhibited by the variant GIFN4, as demonstrated by modulated MHC I:PD-L1 ratios relative to a reference ratio observed in control dendritic cells treated with wild-type IFN-γ (see, FIG. 10I).

Taken together, the experiments described in this Example demonstrates that while all the partial agonists described above efficiently upregulate class I MHC expression in dendritic cells, PD-L1 expression in these cells by the partial agonists is limited with the greatest bias exhibited by the variant GIFN4.

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

What is claimed is:

1. A recombinant polypeptide comprising a first amino acid sequence and a second amino acid sequence:
   (a) the first amino acid sequence having at least 95% identity to an interferon-gamma (IFN-γ) polypeptide having the amino acid sequence of SEQ ID NO: 1; and further comprising three amino acid substitutions K74A, E75Y, and N83R; and
   (b) the second amino acid sequence having at least 95% identity to a gamma-interferon polypeptide having the amino acid sequence of SEQ ID NO: 1,
   wherein the second amino acid sequence is operably linked to the first amino acid sequence, and
   wherein the recombinant polypeptide is an IFN-γ agonist.

2. The polypeptide of claim 1, wherein the first amino acid sequence has 100% sequence identity to the amino acid sequence of SEQ ID NO: 1, except for the amino acid substitutions K74A, E75Y, and N83R.

3. The polypeptide of claim 1, wherein the first amino acid sequence further comprises one or more additional amino acid substitutions at positions corresponding to amino acid residues selected from the group consisting of A23, D24, N25, H111 of SEQ ID NO: 1, and any combination thereof.

4. The polypeptide of claim 1, wherein the second amino acid sequence comprises at least one amino acid substitution at a position corresponding to an amino acid residue selected from the group consisting of K74, E75, N83, D2, P3, K6, Q64, Q67, K68, E71, T72, D76, N78, V79, K80, S84, K86, R89, and D90 of SEQ ID NO: 1, and any combination thereof.

5. The polypeptide of claim 4, wherein the second amino acid sequence comprises three amino acid substitutions at positions corresponding to K74, E75, and N83 of SEQ ID NO: 1.

6. The recombinant polypeptide of claim 5, wherein:
   (a) the amino acid substitution at position corresponding to K74 of SEQ ID NO: 1 is Lys-to-Ala substitution (K74A);
   (b) the amino acid substitution at position corresponding to E75 of SEQ ID NO: 1 is Glu-to-Tyr substitution (E75Y); and
   (c) the amino acid substitution at position corresponding to N83 of SEQ ID NO: 1 is Asn-to-Arg substitution (N83R).

7. The polypeptide of claim 4, wherein the second amino acid sequence further comprises one or more additional amino acid substitutions at positions corresponding to amino acid residues selected from the group consisting of A23, D24, N25, H111 of SEQ ID NO: 1, and any combination thereof.

8. The polypeptide of claim 1, wherein the second amino acid sequence is operably linked to the first amino acid sequence via a peptide linker sequence.

9. The polypeptide of claim 8, comprising, in the N-terminal to C-terminal direction:
   a) (i) a second polypeptide segment comprising a second amino acid sequence with 100% sequence identity to SEQ ID NO: 1; (ii) a cleavable peptide linker sequence; and (iii) a first polypeptide segment comprising the amino acid sequence of SEQ ID NO: 1 with amino acid substitutions K74A, E75Y, and N83R;
   b) (i) a second polypeptide segment comprising the amino acid sequence of SEQ ID NO: 1 with the amino acid substitution H111D; (ii) a cleavable peptide linker sequence; and (iii) a first polypeptide segment comprising the amino acid sequence of SEQ ID NO: 1 with the amino acid substitutions K74A, E75Y, and N83R; or
   c) (i) a second polypeptide segment comprising the amino acid sequence of SEQ ID NO: 1 with the amino acid substitutions A23E, D24E, N25K, K74A, E75Y, N83R, and H111D; (ii) a cleavable peptide linker sequence; and (iii) a first polypeptide segment comprising the amino acid sequence of SEQ ID NO: 1 with the amino acid substitutions K74A, E75Y, and N83R.

10. The polypeptide of claim 1, wherein the polypeptide comprises an amino acid sequence selected from the group consisting of SEQ ID NO: 1, SEQ ID NO: 2, SEQ ID NO: 3, and SEQ ID NO: 4.

11. The polypeptide of claim 1, wherein at least one of the amino acid substitutions confers reduced binding affinity of the polypeptide to interferon-gamma receptor subunit 1 (IFN-γR1) and/or interferon-gamma receptor subunit 2 (IFN-γR2), compared to the respective binding affinity of a reference polypeptide lacking the at least one amino acid substitution.

12. The polypeptide of claim 11, wherein the ratio of IFN-γR2 binding affinity to IFN-γR1 binding affinity of the polypeptide is about 1:500 to about 1:2, as determined by a solid-phase receptor binding assay.

13. A composition comprising a pharmaceutical acceptable excipient and one or more of the following:
   a) a polypeptide according to claim 1;
   b) a nucleic acid molecule encoding the polypeptide of (a); and
   c) a recombinant cell comprising the nucleic acid molecule of (b).

14. A recombinant polypeptide comprising an amino acid sequence having at least 95% identity to an interferon-gamma (IFN-γ) polypeptide having the amino acid sequence of SEQ ID NO: 1, wherein the recombinant polypeptide comprises three amino acid substitutions at positions corresponding to K74, E75, and N83 of SEQ ID NO: 1, and wherein the recombinant polypeptide is an IFN-γ agonist.

15. The recombinant polypeptide of claim 14, wherein:
   (a) the amino acid substitution at position corresponding to K74 of SEQ ID NO: 1 is Lys-to-Ala substitution (K74A);
   (b) the amino acid substitution at position corresponding to E75 of SEQ ID NO: 1 is Glu-to-Tyr substitution (E75Y); and
   (c) the amino acid substitution at position corresponding to N83 of SEQ ID NO: 1 is Asn-to-Arg substitution (N83R).

16. A method for modulating IFN-γ-mediated signaling in a subject, the method 1 comprising administering to the subject an effective amount of a polypeptide according to claim 1.

17. The method of claim 16, wherein the method is for the treatment of a health disease in the subject.

18. The method of claim 17, wherein the subject has or is suspected of having a health disease associated with IFN-γ-mediated signaling.

19. The method of claim 18, wherein the health disease is a cancer, an immune disease, or a chronic infection.

20. The method of claim 16, wherein the administered polypeptide:
   a) has reduced capacity to upregulate expression of Programmed death-ligand 1 (PD-L1) in the subject, as compared to a reference polypeptide lacking the at least one amino acid substitution;
   b) retains its capacity to upregulate expression of one or more of MHC Class I molecules;
   c) has reduced capacity to upregulate expression of PD-L1 while substantially retaining its capacity to upregulate expression of one or more MHC Class I molecules in the subject; and/or
   d) enhances antitumor immunity in a tumor microenvironment.

21. The method of claim 16, wherein the administration of the polypeptide does not inhibit T-cell activity in the subject.

* * * * *